United States Patent
Buehler et al.

(10) Patent No.: US 11,643,444 B2
(45) Date of Patent: May 9, 2023

(54) SILK NANOFIBRILS AND USES THEREOF

(71) Applicants: Trustees of Tufts College, Medford, MA (US); Massachusetts Institute of Technology, Cambridge, MA (US)

(72) Inventors: Markus J. Buehler, Boxford, MA (US); David L. Kaplan, Concord, MA (US); Shengjie Ling, Allston, MA (US); Kai Jin, Cambridge, MA (US)

(73) Assignees: TRUSTEES OF TUFTS COLLEGE, Medford, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 343 days.

(21) Appl. No.: 16/098,954

(22) PCT Filed: Mar. 31, 2017

(86) PCT No.: PCT/US2017/025632
§ 371 (c)(1),
(2) Date: Nov. 5, 2018

(87) PCT Pub. No.: WO2017/192227
PCT Pub. Date: Nov. 9, 2017

(65) Prior Publication Data
US 2020/0181213 A1   Jun. 11, 2020

Related U.S. Application Data

(60) Provisional application No. 62/331,899, filed on May 4, 2016.

(51) Int. Cl.
| | |
|---|---|
| C07K 14/435 | (2006.01) |
| C12N 5/077 | (2010.01) |
| B01D 61/14 | (2006.01) |
| B01D 71/74 | (2006.01) |
| D01B 7/00 | (2006.01) |
| D01C 3/02 | (2006.01) |

(52) U.S. Cl.
CPC ...... *C07K 14/43586* (2013.01); *B01D 61/145* (2013.01); *B01D 71/74* (2013.01); *C12N 5/0656* (2013.01); *D01B 7/00* (2013.01); *D01C 3/02* (2013.01)

(58) Field of Classification Search
None
See application file for complete search history.

(56) References Cited

U.S. PATENT DOCUMENTS

| | | | |
|---|---|---|---|
| 5,245,012 A | 9/1993 | Lombari | |
| 7,842,780 B2 | 11/2010 | Kaplan | |
| 2007/0082197 A1* | 4/2007 | Ko | D04H 1/43825 |
| | | | 428/367 |
| 2007/0214520 A1* | 9/2007 | Scheibel | A61L 27/227 |
| | | | 800/288 |
| 2010/0178304 A1 | 7/2010 | Wang | |
| 2010/0279112 A1 | 11/2010 | Kaplan | |
| 2011/0171239 A1 | 7/2011 | Kaplan | |
| 2015/0148823 A1* | 5/2015 | Mortarino | A61L 31/148 |
| | | | 606/151 |
| 2015/0165092 A1 | 6/2015 | Kaplan | |
| 2015/0183841 A1 | 7/2015 | Lo | |
| 2015/0202351 A1 | 7/2015 | Kaplan | |

FOREIGN PATENT DOCUMENTS

| | | |
|---|---|---|
| CN | 104532365 | 4/2015 |
| WO | 1997008315 | 3/1997 |
| WO | 2004062697 | 7/2004 |
| WO | 2007098951 | 7/2007 |
| WO | 2008150861 | 12/2008 |
| WO | 2011005381 | 1/2011 |
| WO | 2015077556 | 5/2015 |

OTHER PUBLICATIONS

Acharya, C., et al. "Performance evaluation of a silk protein-based matrix for the enzymatic conversion of tyrosine to L-DOPA." Biotechnology Journal: Healthcare Nutrition Technology 3.2 (2008): 226-233.

Bayraktar, O., et al. "Silk fibroin as a novel coating material for controlled release of theophylline." European Journal of Pharmaceutics and Biophamnaceutics 60.3 (2005): 373-381.

Demura, M. et al. "Immobilization of glucose oxidase with Bombyx mori silk fibroin by only stretching treatment and its application to glucose sensor." Biotechnology and bioengineering 33.5 (1989): 598-603.

Hersel, U., et al "RGD modified polymers: biomaterials for stimulated cell adhesion and beyond." Biomaterials 24.24 (2003): 4385-4415.

Hofmann, S., et al. "Silk fibroin as an organic polymer for controlled drug delivery." Journal of Controlled Release 111.1-2(2006): 219-227.

Hu, X., et al. "Regulation of silk material structure by temperature-controlled water vapor annealing." Biomacromolecules 12.5 (2011): 1686-1696.

Jin, H.-J., et al. "Water-stable silk films with reduced β-sheet content." Advanced Functional Materials 15.8 (2005): 1241-1247.

Lu, S., et al. "Stabilization of enzymes in silk films." Biomacromolecules 10.5 (2009): 1032-1042.

Miyairi, S. et al. "Properties of β-Glucosidase Immobilized in Serichin Membrane." Journal offermentation technology 56.4 (1978): 303-308.

Schaffner, P., et al. "Structure and function of RGD peptides involved in bone biology." Cellular and Molecular Life Sciences CMLS 60.1 (2003): 119-132.

(Continued)

*Primary Examiner* — Teresa E Knight
(74) *Attorney, Agent, or Firm* — GTC Law Group PC & Affiliates

(57) ABSTRACT

The present invention, in some aspects, provides compositions including a solution comprising a plurality of exfoliated silk microfibrils and/or exfoliated silk nanofibrils, wherein the micro- or nano-fibrils are characterized as having a substantially nematic structure, as well as methods for making and using the same.

20 Claims, 45 Drawing Sheets

(56) References Cited

OTHER PUBLICATIONS

Akthakul, A. et al. "Antifouling polymer membranes with subnanometer size selectivity." Macromolecules 37.20 (2004): 7663-7668.
Braeken, L. et al. "Flux decline in nanofiltration due to adsorption of dissolved organic compounds: model prediction of time dependency." The Journal of Physical Chemistry B 110.6 (2006): 2957-2962.
Deng, C. et al. "Ultrathin self-assembled anionic polymer membranes for superfast size-selective separation." Nanoscale 5.22 (2013): 11028-11034.
Foo, C. Wong Po, et al. "Role of pH and charge on silk protein assembly in insects and spiders." Applied Physics A 82.2 (2006): 223-233.
Cao, S. J., et al. "SWCNT-intercalated GO ultrathin films for ultrafast separation of molecules." Journal of Materials Chemistry A 3.12 (2015): 6649-6654.
Giesa, T. et al. "Nanoconfinement and the Strength of Biopolymers." Annual review of biophysics 42 (2013): 651-673.
He, J., et al. "Diffusion and filtration properties of self-assembled gold nanocrystal membranes." Nano letters 11.6 (2011): 2430-2435.
Huang, Hubiao, et al. "Ultrafast viscous water flow through nanostrand-channelled graphene oxide membranes." Nature communications 4 (2013): 2979.
International Search Report and Written Opinion for application PCT/US2017/025632, dated Jul. 3, 2017, 9 pages.
Karan, Santanu, et al. "Ultrathin free-standing membranes from metal hydroxide nanostrands." Journal of membrane science 448 (2013): 270-291.
Keten, Sinan, et al. "Nanoconfinement controls stiffness, strength and mechanical toughness of β-sheet crystals in silk." Nature materials 9.4 (2010): 359.
Koh, Leng-Duei, et al. "Structures, mechanical properties and applications of silk fibroin materials." Progress in Polymer Science 46 (2015): 86-110.
Krieg, Elisha, et al. "A recyclable supramolecular membrane for size-selective separation of nanoparticles." Nature nanotechnology 6.3 (2011): 141.
Lee, Yong Man, et al. "Nanomesh-Structured Ultrathin Membranes Harnessing the Unidirectional Alignment of Viruses an a Graphene-Oxide Film." Advanced Materials26.23 (2014): 3899-3904.
Liang, Hai-Wei, et al. "Carbonaceous nanofiber membranes for selective filtration and separation of nanoparticles." Advanced Materials 22.42 (2010): 4691-4695.
Lin, N. et al. "Correlation between hierarchical structure of crystal networks and macroscopic performance of mesoscopic soft materials and engineering principles." Chemical Society Reviews 44.21 (2015): 7881-7915.
Ling, S., et al. "Directed growth of silk nanofibrils on graphene and their hybrid nanocomposites." ACS Macro Letters 3.2 (2014): 146-152.
Ling, S., et al. "Modulating materials by orthogonally oriented β-strands: Composites of amyloid and silk fibroin fibrils." Advanced Materials 26.26 (2014): 4569-4574.
Ling, S., et al. "Synchrotron FTIR microspectroscopy of single natural silk fibers." Biomacromolecules 12.9 (2011): 3344-3349.
Lu, Yunyi, et al. "Nanofiltration membranes based on rigid star amphiphiles." Chemistry of materials 19.13 (2007): 3194-3204.
Mondia, J. P., et al. "Rapid nanoimprinting of doped silk films for enhanced fluorescent emission." Advanced Materials22.41 (2010): 4596-4599.
Nova, Andrea, et al. "Molecular and nanostructural mechanisms of deformation, strength and toughness of spider silk fibrils." Nano letters 10.7 (2010): 2626-2634.
Omenetto, F. G. et al. "New opportunities for an ancient material." Science 329.5991 (2010): 528-531.
Peng, X. S., et al. "Mesoporous Separation Membranes of Polymer-Coated Copper Hydroxide Nanostrands." Advanced Functional Materials 17.11 (2007): 1849-1855.
Peng, X., et al. "Ultrafast permeation of water through protein-based membranes." Nature nanotechnology 4.6 (2009): 353.
Rockwood, D. N., et al. "Materials fabrication from Bombyx mori silk fibroin." Nature protocols 6.10(2011): 1612.
Shannon, M. A., et al. (2008). Science and technology for water purification in the coming decades, Nature, 452 (7185), 301-310.
Sun, L. et al. "Laminar MoS 2 membranes for molecule separation." Chemical communications 49.91 (2013): 10718-10720.
Sun, Luwei, et al. "Ultrafast molecule separation through layered WS2 nanosheet membranes." ACS nano 8.6 (2014): 6304-6311.
Tansil, N. C., et al. "Intrinsically colored and luminescent silk." Advanced Materials 23.12 (2011): 1463-1466.
Termonia, Yves. "Molecular modeling of spider silk elasticity." Macromolecules 27.25 (1994): 7378-7381.
Van Beek, J. D., et al. "Solid-state NMR determination of the secondary structure of Samia cynthia ricini silk." Nature405.6790 (2000): 1077.
Vandezande, P. et al. "Solvent resistant nanofiltration: separating on a molecular level." Chemical Society Reviews 37.2 (2008): 365-405.
Vankelecom, Ivo, et al. "Nanofiltration membrane materials and preparation." pp. 34-65. Nanofiltration: Principles and Applications, Elsevier: New York, 2005.
Wang, Q. et al. "Ultrafiltration Membranes Composed of Highly Cross-Linked Cationic Polymer Gel: the Network Structure and Superior Separation Performance." Advanced Materials 23.17 (2011): 2004-2008.
Zhang, Q., et al. "Ultrathin freestanding nanoporous membranes prepared from polystyrene nanoparticles." Journal ol Materials Chemistry 21.6 (2011): 1684-1688.
Zhang, Q., et al. "Sub-10 nm Wide Cellulose Nanofibers for Ultrathin Nanoporous Membranes with High Organic Permeation." Advanced Functional Materials 26.5 (2016): 792-800.

\* cited by examiner

BRILLIANT YELLOW

RODANMINE B

DIRECT RED 81

FLUORESCENT BRIGHTER 28

CONGO RED

SILK NANOFIBRILS AND USES THEREOF

CROSS-REFERENCE TO RELATED APPLICATIONS

This application represents the national stage entry of PCT/US2017/025632, filed Mar. 31, 2017, which claims benefit of U.S. Provisional Patent Application 62/331,899 filed May 4, 2016. The contents of this application are hereby incorporated by reference as set forth in their entirety herein.

GOVERNMENT FUNDING STATEMENT

This invention was made with government support under grant number EB014976 awarded by the National Institutes of Health. The government has certain rights in the invention.

BACKGROUND

Direct extraction of nano-scale building blocks from natural materials has been actively pursued as a method to retain the exquisite structure and superior physical properties of natural nanomaterials. A variety of methods have been developed to extract cellulose and chitin nanomaterials. However, direct extraction of silk microfbrils and nanofibrils from natural silk fibers remains a challenge due to the high-crystallinity and complex hierarchical structure. To date, only a chemical method (formic acid/$CaCl_2$ dissolution) and a physical method (ultrasonication) have been reported but both with intrinsic limitations. Formic acid/$CaCl_2$ dissolution generates silk nanofibril bundles or aggregates and these silk nanofibrils are only stable for a short time (less than 6 hours) due the dissolution imposed by the formic acid. For the ultrasonic method, silk fibers are only exfoliated to generate silk nanofibril mats and lack reprocessing, thus limiting for the regeneration of materials. More importantly, both methods do not exfoliate silk fibers on the single silk nanofibril scale which is crucial when defining the mechanical properties of silks and is helpful as a starting point for the regeneration of new materials.

Animal silks, produced by spiders and silkworms, have attracted the intense attention of scientists and engineers for more than a century, not only because of their marvelous mechanical properties, but also due to their diverse applications in textiles, optics, and biomedicine. In addition to in-depth studies of the physical properties and functions of natural silk fibers, experimental attempts have been pursued to mimic the natural process of producing robust regenerated silk fibers (RSFs) to emulate the properties of natural silk fibers. Wet spinning techniques, ejection of the spinning dope into a coagulation bath (often containing alcohols or salts), are the most common approach to generate RSFs. However, these methods are complicated, generally include dissolution, dialysis, concentration, spinning and post-treatment processes, and all of the steps are time-consuming, energy-intensive and require relatively large quantities of solvent. In contrast, spiders and silkworms construct webs and cocoons by directly reeling (similar to 3D printing processes) a pre-assembled nematic silk protein dope (as with printing inks). All of these processes are conducted under physiological and ambient conditions without any additional immobilization and post-processing steps. The main structural silk fibroin is synthesized at the epithelial wall of posterior silk gland (the tail of gland) with a concentration around 12 wt %. Next, the fibroin moves to the wider middle division (sac or ampulla) with an increase in concentration (~25 wt %) and assembles to a micelle-like configuration with anisotropic liquid crystalline properties. The liquid crystallinity allows the molecules to flow in a pre-aligned manner and to further align along the flow axis during the passage through the spinning duct. Finally, silk fiber formation occurs under shear stress and dehydration conditions during the pulling out of the fiber from the spigot.

Several reported dry-spinning technologies have shown advantages for mimicking this fantastic natural spinning process, including ease of operation, and relatively low cost, but these methods still require complex post-processing treatments to generate useful RSFs. This drawback deeply hinders the application of these methods, and more importantly, all of these attempts (including wet- and dry-spinning) only focus on reproducing the mechanical properties of natural silks, and less focus on retaining the hierarchical structures of silks, a key feature in the properties of the natural protein fibers. Accordingly, previously known methods of trying to mimic the natural process of silk spinning have proven unsatisfactory for several reasons.

SUMMARY

The present invention provides, among other things, new methods and compositions providing exfoliated and/or regenerated silk micro- and nano-fibrils which retain the hierarchical architecture of native silk fibers, while enjoying increased biocompatibility and biodegradability and requiring no post-treatments. These unexpected new methods and compositions allow for use these regenerated or exfoliated silk fibrils to be used for many of the current applications of silk fibers while providing a previously unavailable physical properties, including but not limited to, ultra-low temperature toughness, unique fracture modes, excellent dyeing and finishing capacity, and advantageous tensile properties.

The present invention, in some aspects, provides compositions including a solution comprising a plurality of exfoliated silk microfibrils, wherein the microfibers are characterized as having a substantially nematic structure.

In some embodiments, the present invention provides compositions including a plurality of exfoliated silk microfibrils. In some embodiments, composition is or comprises a sensor or implant. In some embodiments, provided compositions further include a substrate.

Aspects of the present invention may provide silk microfibrils with any of a variety of tailorable physical characteristics. For example, in some embodiments, provided silk microfibrils have a diameter between 5 and 50 μm, inclusive. In some embodiments, provided silk microfibrils have a length between 5 μm and 50 mm, inclusive.

In some embodiments, the present invention also provides compositions including a solution comprising a plurality of exfoliated silk nanofibrils, wherein the nanofibrils are characterized as having a substantially nematic structure. In some embodiments, the silk nanofibrils have a diameter between 2 and 200 nm, inclusive. In some embodiments, the silk nanofibrils have a length between 50 and 2,000 nm, inclusive.

In some embodiments, the present invention also provides compositions including a plurality of exfoliated silk nanofibrils. In some embodiments, the composition is or comprises a sensor, ultrafiltration membrane, adsorbant agent, flocculating agent, or implant. In some embodiments, the composition further includes a substrate.

In accordance with various embodiments, provided compositions include micro- or nano-fibrils comprising hierarchical structures similar to or even substantially the same as native silk fibers. For example, in some embodiments, provided compositions comprise microfibrils having a helical or spiral structure.

In some embodiments, provided compositions may further include one or more cells. In some embodiments, for example, the one or more cells may be selected from the group consisting of fibroblasts, stem cells, immune cells, nervous system cells, adipose tissue-derived cells, and blood cells.

According to various embodiments, provided compositions include silk micro- or nano-fibrils that approximate one or more of the desirable physical characteristics of native silk fibers. For example, in some embodiments, provided regenerated silk fibers made by micro- or nano-fibrils individually have an elongation at break that is substantially the same as a native silk fiber. In some embodiments, such provided regenerated silk fibers exhibit a modulus that is even higher than native silk fibers.

Additionally, in some embodiments, provided compositions further include at least one additive. In some embodiments, the at least one additive is or comprises a dye, a growth factor, an anti-inflammatory agent, an anti-microbial agent, quantum dots, conductive polymers, or an inorganic material. In some embodiments, the inorganic material is or comprises a metal or ceramic material. In some embodiments, the at least one additive is or comprises carbon nanotubes. In some embodiments, the silk micro- or nano-fibrils comprise a coating.

In accordance with various embodiments, provided methods include exposing native silk fibers to one or more polar organic solvents for an extended period of time (e.g., at least 8 hours). In some embodiments, the present invention also provides methods of making exfoliated silk microfibrils including the step of exposing a degummed native silk fiber to a polar organic solvent for a period of time to produce a solution comprising exfoliated silk microfibrils comprising a nematic structure.

The present invention also provides, in some embodiments, methods including the steps of exposing a degummed native silk fiber to a polar organic solvent for a period of time to produce exfoliated silk microfibrils comprising a nematic structure, removing the organic solvent to produce a silk microfibril material, dispersing the silk microfibril material in an aqueous solution, and agitating the silk microfibril material to form a silk nanofibril dispersion. In some embodiments, the agitating comprises at least one of sonication, high pressure homogenization, comminuting, cryomilling, and combinations thereof. In some embodiments, provided methods further include removing undissolved silk fibers from the dispersed silk microfibril material prior to the agitation step. In some embodiments, the removing is accomplished by one or both of centrifugation and filtration.

In some embodiments, the exposing step continues for at least 24 hours. In some embodiments, the exposing step continues for at least 1 week. In some embodiments, the exposing step continues for at least 10 days. In some embodiments, the exposing step continues for at least 1 month.

In some embodiments, provided methods further include extruding the exfoliated silk micro- or nano-fibrils to produce a regenerated silk fiber comprising a plurality of aligned silk micro- or nano-fibrils.

In some embodiments, provided methods further include removing the organic solvent to produce a silk micro- or nano-fibril material, dispersing the silk micro- or nano-fibril material in an aqueous solution to form a silk micro- or nano-fibril dispersion.

In some embodiments, the polar organic solvent is selected from the group consisting of hexafluoro-2-propanol, lithium bromide, calcium chloride, ethanol, formic acid, 1-ethyl-3-methylimidazolium acetate, triethylammonium phosphate (TeaH2PO4), triethylammonium lactate, (TeaLa), triethylammonium triflate, and triethylammonium mesylate.

In some embodiments, provided methods include exposing native silk fibers to at least one polar organic solvent at a temperature at or above normal room temperature (i.e., approximately 37° C.). In some embodiments, the exposing step occurs at a temperature between 40° C. and 60° C., inclusive.

In accordance with several embodiments, the use of temperatures at or above normal room temperature may result in the evaporation of some or much of the polar organic solvent during the exposing step. As such, in some embodiments, it can be helpful to perform provided methods in a system capable of capturing any evaporated polar organic solvent. In some embodiments, such collection may be helpful in the maintaining the appropriate conditions for the exposing step itself (or other steps in some embodiments of provided methods), where as in some embodiments, such collection may be due, at least in part to safety or other reasons. Regardless, in some embodiments, the exposing step occurs in a closed environment (e.g., using an airtight container).

According to any of a variety of embodiments, provided methods allow for the use of a wide range of silk fiber to polar solvent ratios. In some embodiments, the ratio of silk fiber to polar organic solvent is between about 1:10 and 1:100 by weight, inclusive.

One advantage of certain provided methods is that the micro- and/or nano-fibers produced thereby do not require any post-processing treatments in order to provide useful silk micro- and/or nano-fibrils, unlike previously known methods. In some embodiments, the silk microfibrils are not subjected to any post-processing treatment. In some embodiments, the post-processing treatment is selected from the group consisting of lyophilization, critical point drying, and heat drying.

Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The Figures described below, that together make up the Drawing, are for illustration purposes only, not for limitation.

Figure 19:
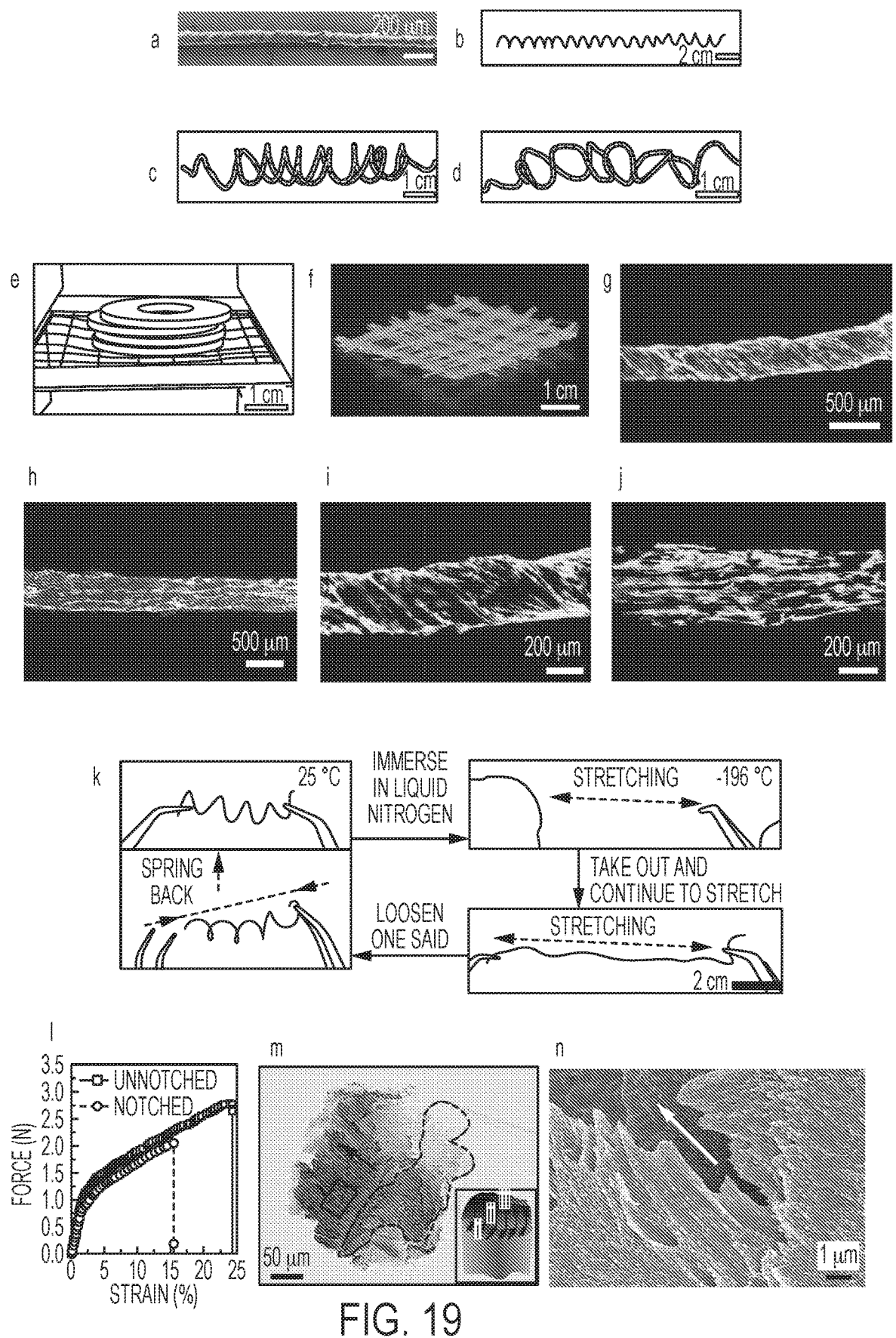

FIG. 19 shows exemplary polymorphic hierarchical RSFs produced by biomimetic spinning and their unique physical properties. (a-d) Polymorphic architectures of RSFs prepared from biomimetic spinning. (a) SEM image of a yarn-like spiral RSF, produced by rotating the collector in a plane direction that perpendicular to the fiber axis. (b) Photograph of a free-standing gourd vine like helix RSF. (c, d) Photographs of colored luminescent RSFs under UV light with parallel- (c) and cross-double helical (d) construction. The red and yellow color of RSFs is by adding Rhodamine B and Rhodamine 123, respectively. (e. f) Photographs of RSF-based 2D and 3D structures, fabricated from the biomimetic spinning process. (g-j) Three-dimensional cell patterns generated on yarn-like spiral and as-spun RSFs. Fluorescent images show the preferential alignment of HDFs (green) along the axes of the (g) and (i) yarn-like spiral and (h) and (j) as-spun RSFs (red). (k) Mechanical performance of RSF under ultra-low temperature. The RSFs retained flexibility after immersion in liquid nitrogen. (l) Load-strain curves of notched and unnotched RSFs. (m) Cross-sectional SEM image of notched RSFs after tensile fracture, which reveals three distinct regions (i-iii), as shown in the insert. The regions i, ii and iii are a notch, crack stable growth area, and crack unstable growth area, respectively. (n) Locally amplified SEM image from white solid frame region of (m). The white row shows the tensile direction. The image shows nanofibrils pulled out along the drawing direction.

Figure 20:
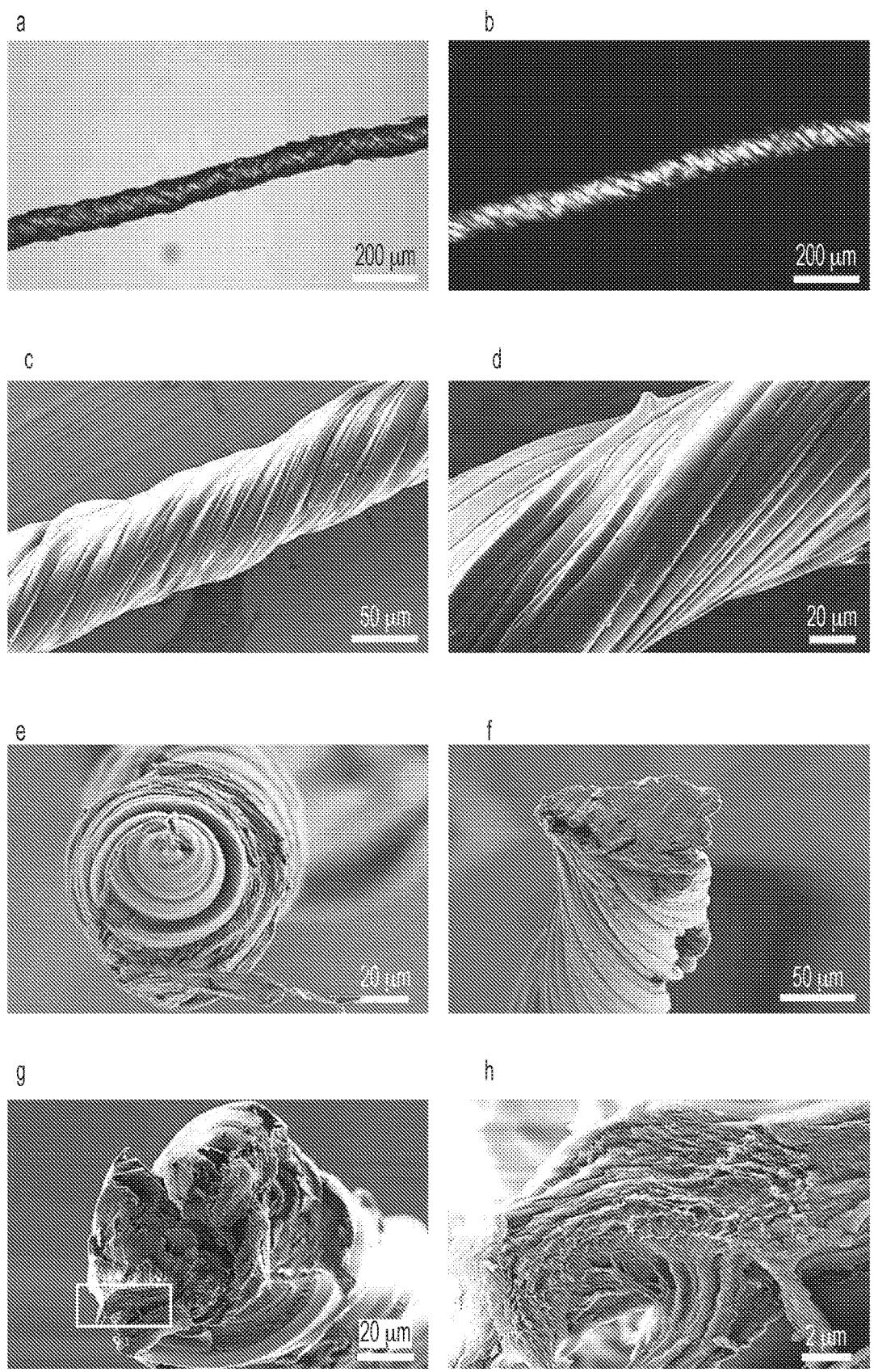

FIG. 20 shows SEM images of an exemplary yarn-like spiral RSF. (a) Microscopy image of yarn-like spiral RSF, (b) Polarized light microscopy of yarn-like spiral RSF, (c, d) Surface (c, d) and cross-sectional (e, f) SEM images of two types of yarn-like spiral RSFs with different pitches. (g) Cross-sectional SEM image of yarn-like RSF after tensile fracture. (h) the locally amplified SEM image from white solid frame region of (g). The image (g) showed clear nanofibril structure in the RSF cross-section.

Figure 21:
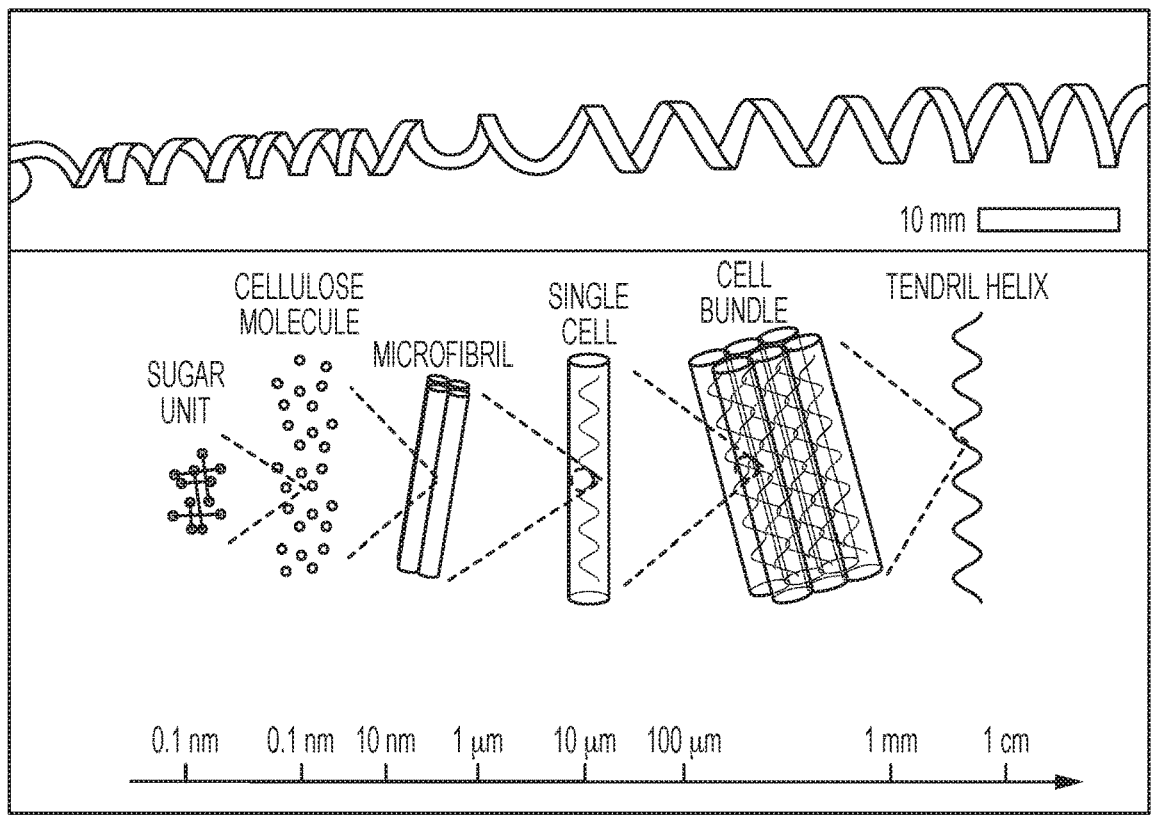
Figure 21:
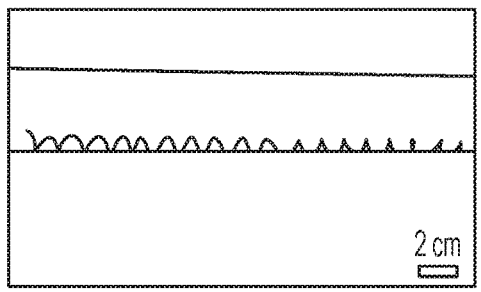
Figure 21:
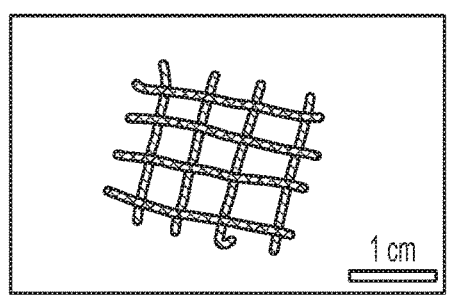
Figure 21:
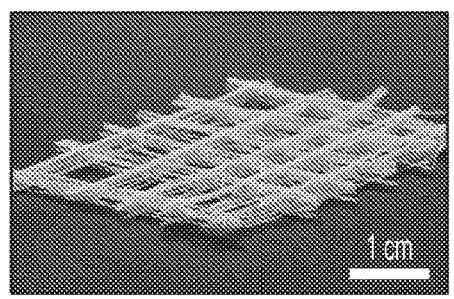

FIG. 21 shows (a) Hierarchical structures of helical gourd vine. The top and bottom images are the photograph of gourd vine and the schematic of the hierarchical structure of gourd vine, respectively. (b) Photograph of helical RSF, which showed the gourd vine-like structure. (c) Photograph of fluorescence-colored 2D RSF grid under UV light. The RSF fiber in warp and weft direction were spun by SMF dope containing Rhodamine B and Rhodamine 123, respectively. (d) Photograph of the free-standing 3D grid.

Figure 22:
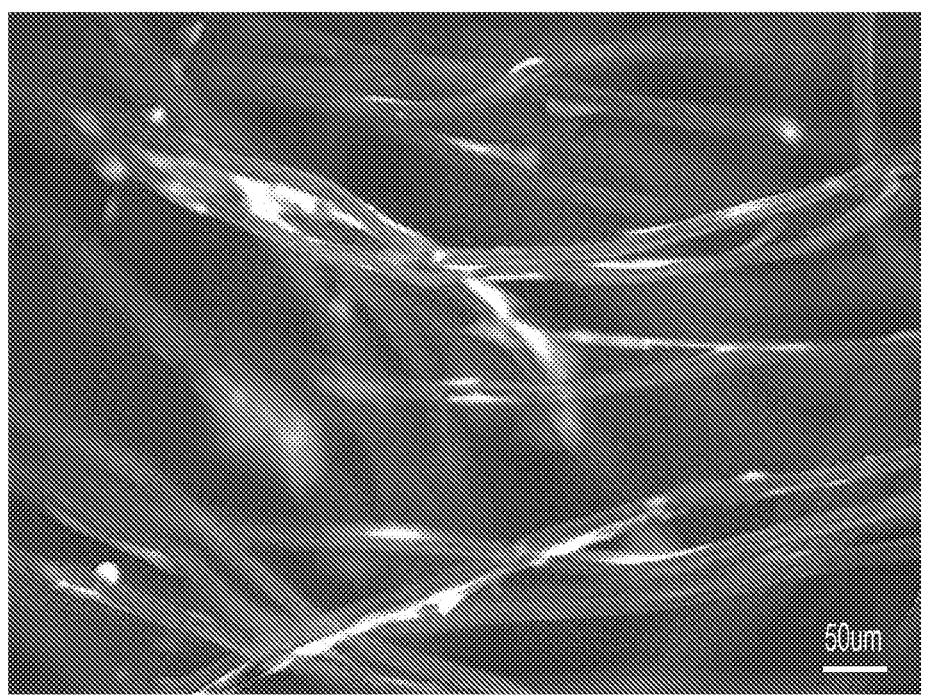

FIG. 22 shows human dermal fibroblasts (green) growth on exemplary randomly arranged degummed silk fibers (red) from *B. mori* silkworm.

Figure 23:
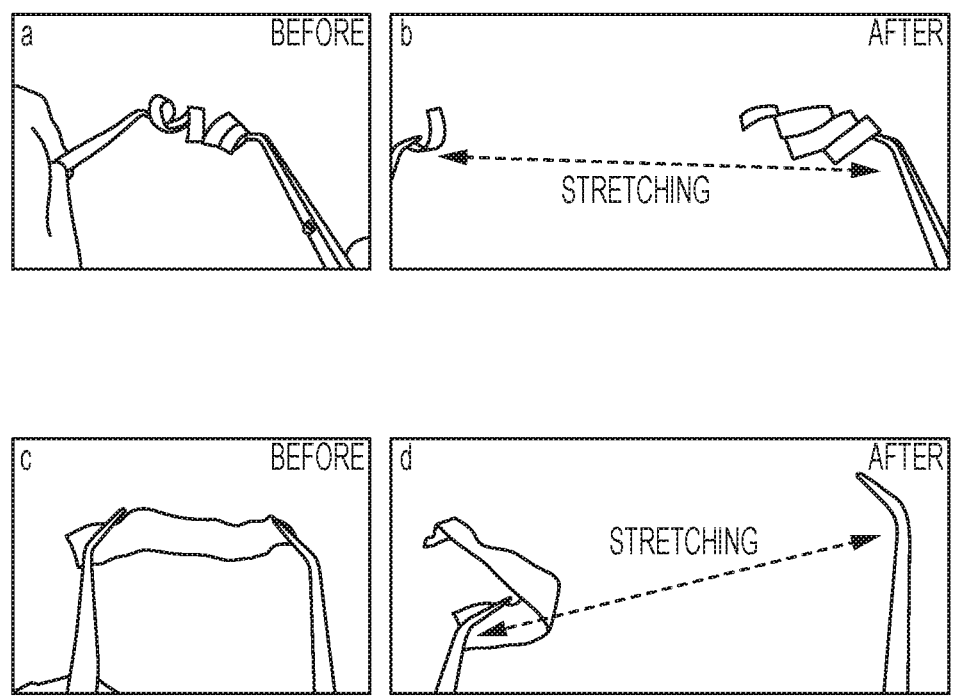

FIG. 23 shows (a) Cellulose paper before immersion in liquid nitrogen. (b) Cellulose paper undergoing stretching after immersion in liquid nitrogen. (c) Nitrile rubber film before immersion in liquid nitrogen. (d) Nitrile rubber film undergoing stretching after immersion in liquid nitrogen. These images indicate that the two materials are brittle at ultralow temperatures.

Figure 24:
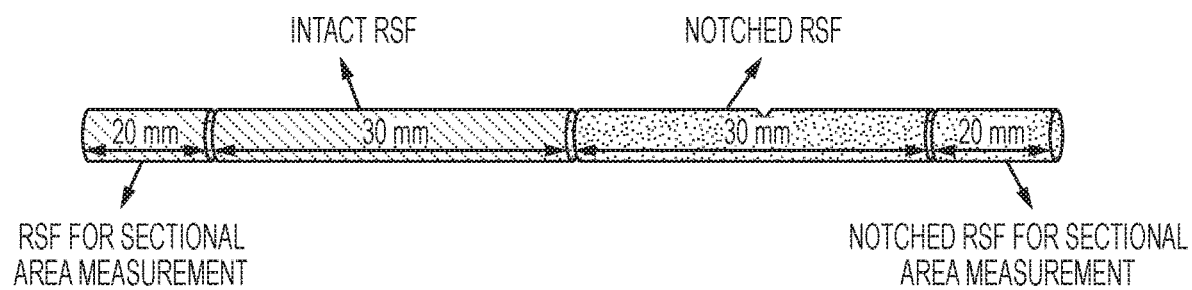
Figure 24:
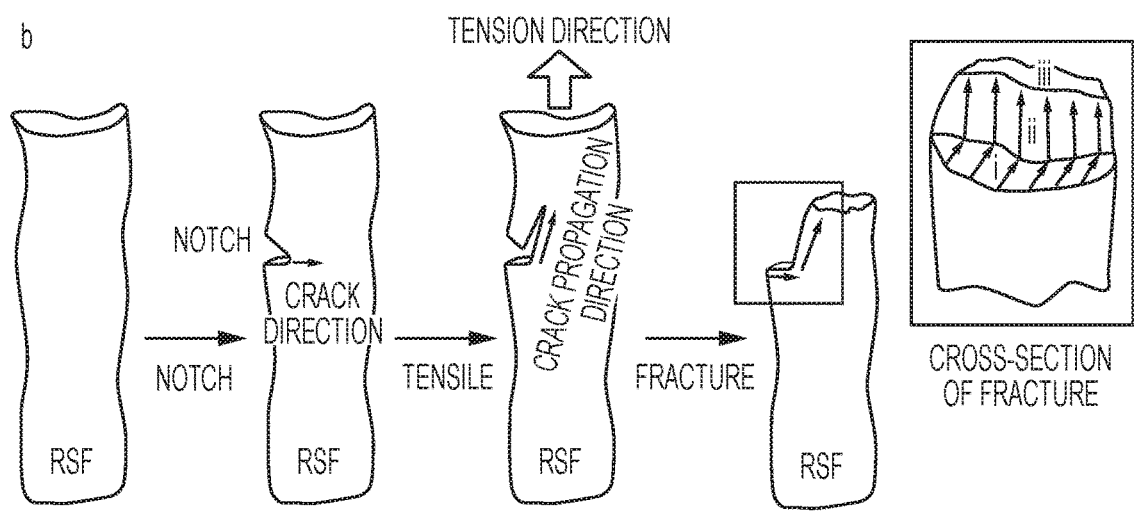

FIG. 24 shows (a) The arrangement of samples for different tests. The Figures and arrows indicate the length of the RSF used. To compare the mechanical properties of notched and un-notched RSFs, two adjacent segments were used. As shown in (A), the right RSF segment was notched with a sharp scalpel from the edge with a depth of 50-100 µm. The notch is in the middle of fiber axis direction. Left RSF segments, without notching, were used for comparison. (b) Ductile fracture mechanisms of RSF. Unlike the brittle materials where the crack propagation direction was perpendicular to the direction of the fiber axis, the crack propagation direction was same as for the native silk fibers and shows three fracture regions. The region i, ii and iii are a notch, crack stable growth area, and crack unstable growth area, respectively.

Figure 25:
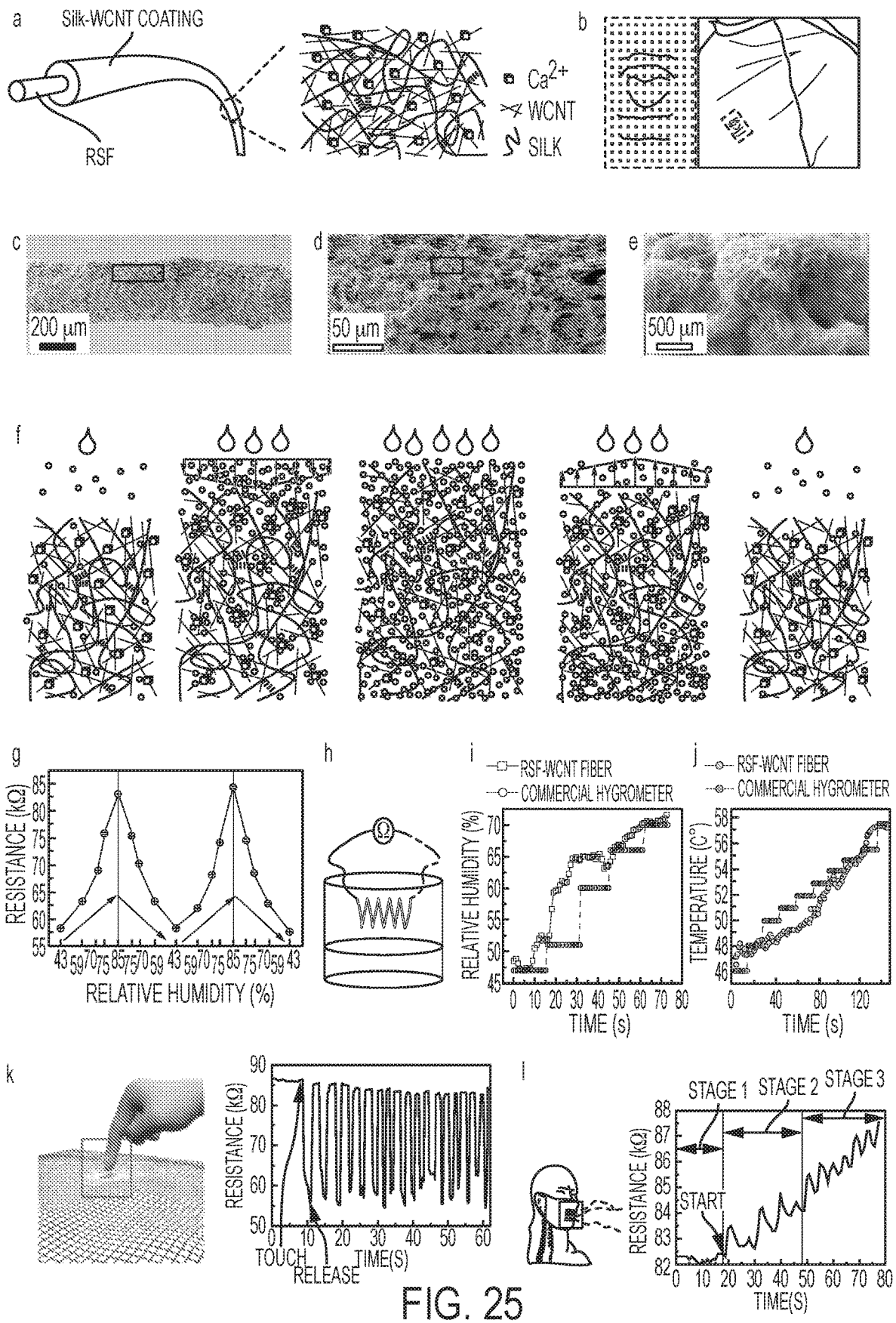

FIG. 25 shows examples of functional RSFs by dip-coating a conductive layer. (a) Illustration of the constitution of conductive core-shell RSFs. The core and coat layer are composed of RSF and silk/WMCNT/$Ca^{2+}$ hybrid composites, respectively. (b) A conductive RSF is weaved into a cloth. These photographs show conductive RSFs are robust and can be weaved to different patterns. (c-e) SEM images of conductive RSF surfaces at different magnifications. The coating layer shows a porous structure, which increased specific surface area and conducive to absorbing more water. The closely stacked WMCNTs, as a conductive composite, observed on the coating layer. (f) Schematic of humidity response mechanism of conductive RSFs. (g) The relationship between relative humidity and resistance. (h) Schematic of experimental setups for monitoring humidity and temperature responses of conductive RSFs. (i) Time-resolved resistance vs RH results of RSF sensor and commercial RH sensor. (j) Time-resolved resistance vs temperature results of RSF sensor and commercial temperature sensor. In order to avoid RH effects on resistance, the RH is kept at 20% during the measurements. (k, l) Resistance response for finger-touching (k) and breathing (l).

Figure 26:
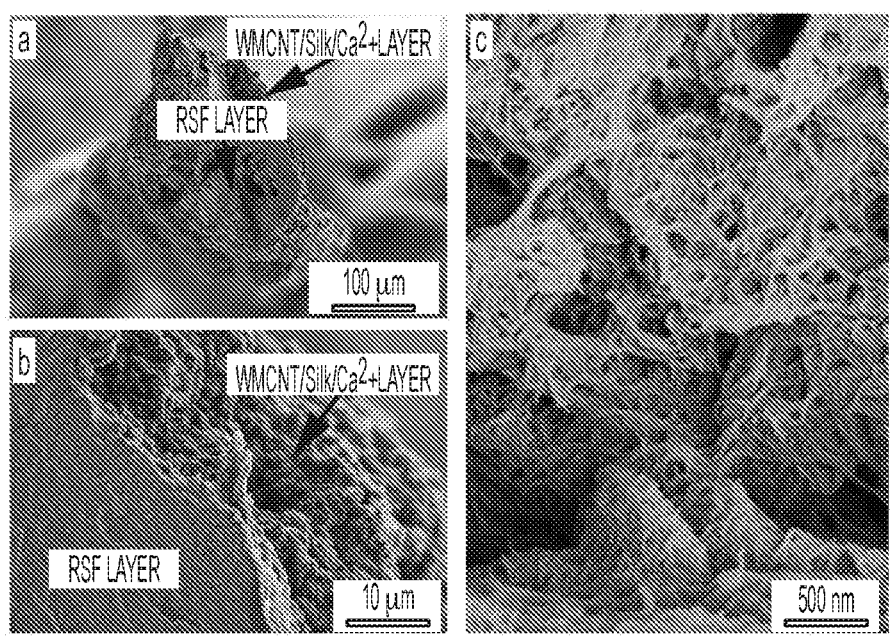

FIG. 26 shows exemplary SEM images of conductive RSFs. (a, b) Cross-sectional SEM image of conductive RSF under small (a) and high (b) magnification. These two images indicate that the WMCNT/silk/$Ca^{2+}$ layers are bonded well with the RSF core. (c) Surface SEM image of conductive WMCNT/silk/$Ca^{2+}$ layer.

Figure 27:
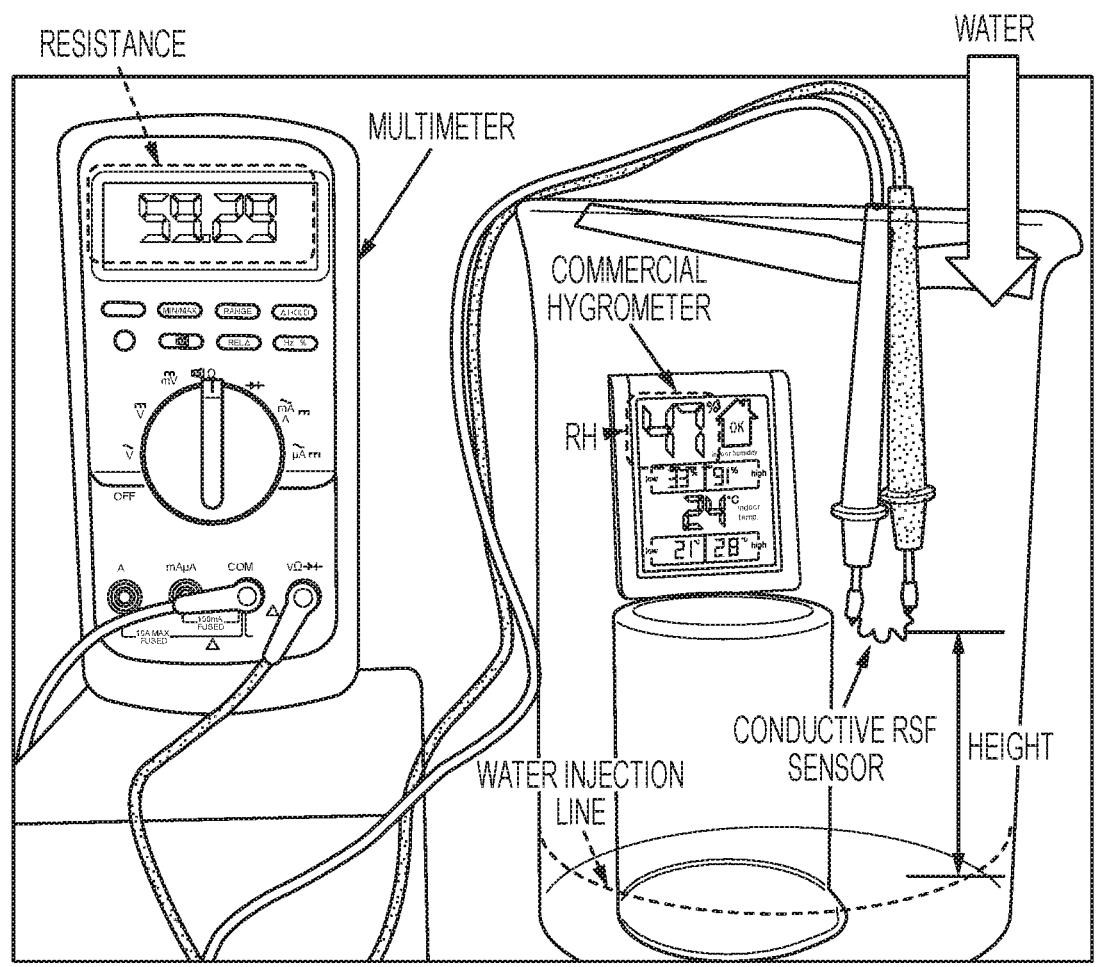

FIG. 27 shows exemplary experimental setups for monitoring humidity and temperature response of conductive RSFs.

Figure 28:
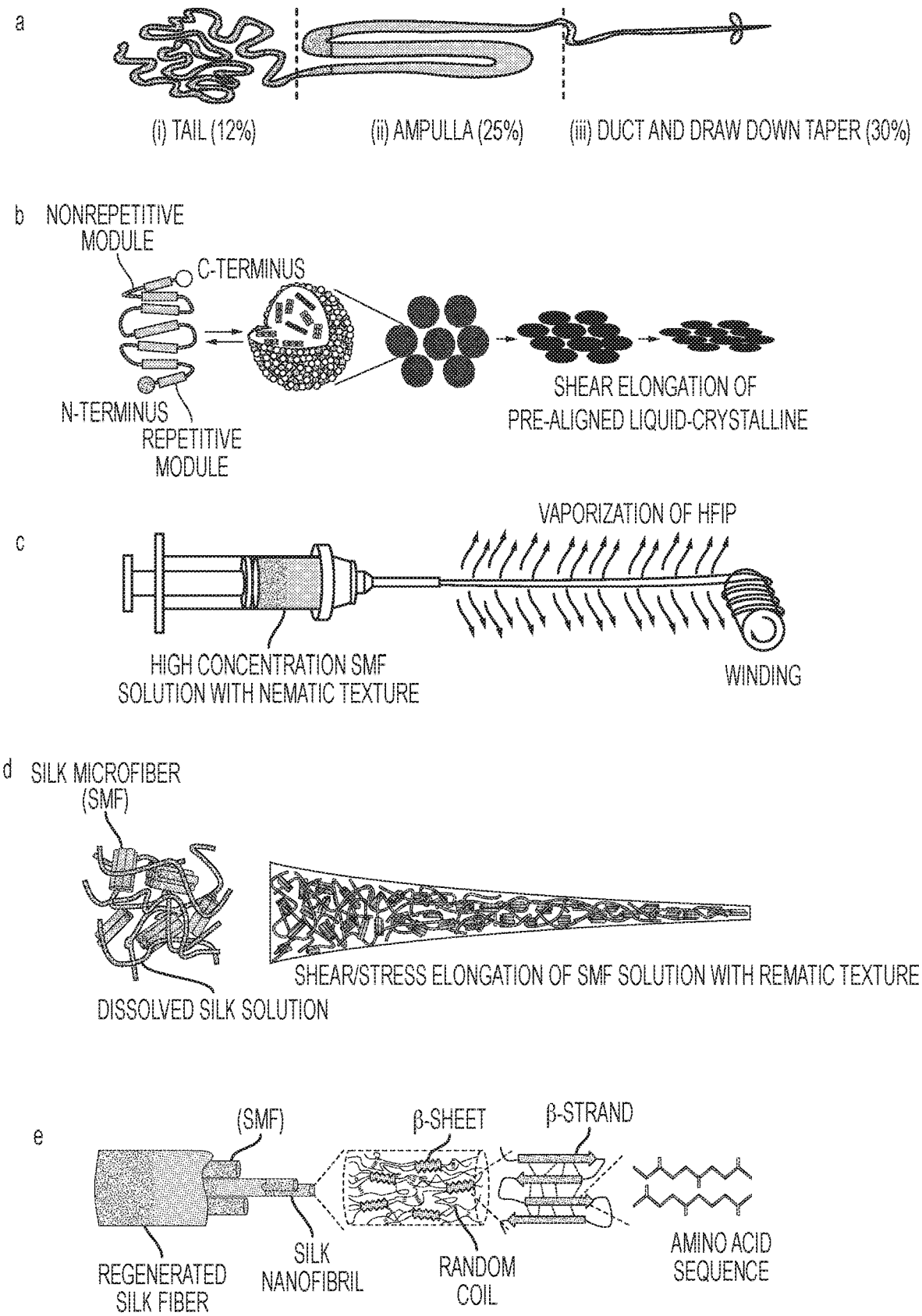

FIG. 28 shows (a) Illustration of a silkworm spinning gland divided into three parts according to the evolution of silk protein during spinning. (b) Schematic model of the natural silk fiber assembly mechanism occurring along the spinning apparatus. The silk proteins are synthesized in the tail and are transferred to ampulla with increased concentration. In this region, the silk proteins are assembled to micelle-like configurations with anisotropic liquid crystalline properties. Finally, silk fiber formation occurs under shear stress and dehydration conditions during pulling out the nematic silk proteins from the spigot. (c) Illustration of an exemplary provided biomimetic spinning process. The nematic silk microfiber solution can be directly assembled into RSFs without additional treatment. (d) Schematic of the SMF evolutionary process during spinning. The SMFs are aligned in the spinning jet (or fiber) axis direction under the shear/stress elongation. (e) Schematic of the hierarchical structure of RSFs. There are at least 5 structural hierarchy levels in RSF.

Figure 29:
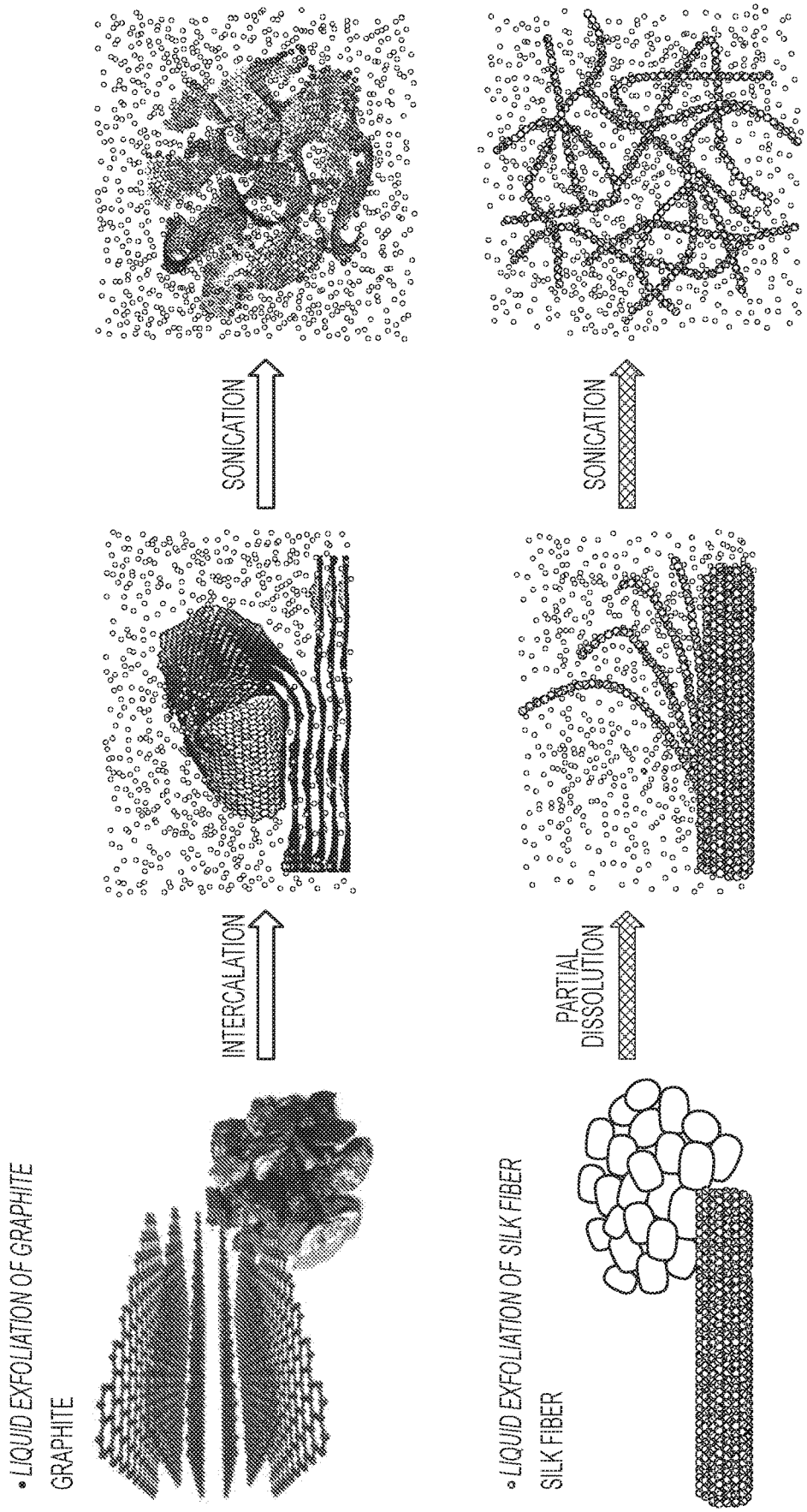

FIG. 29 shows an exemplary schematic representation of certain provided methods for liquid exfoliation of silk fiber. In some embodiments, such methods are inspired, in part, by liquid exfoliation of graphite, which directly exfoliate bulk layered graphite into 2D graphene sheets in the organic solvent without the need for chemical oxidation of the graphite.

Figure 30:
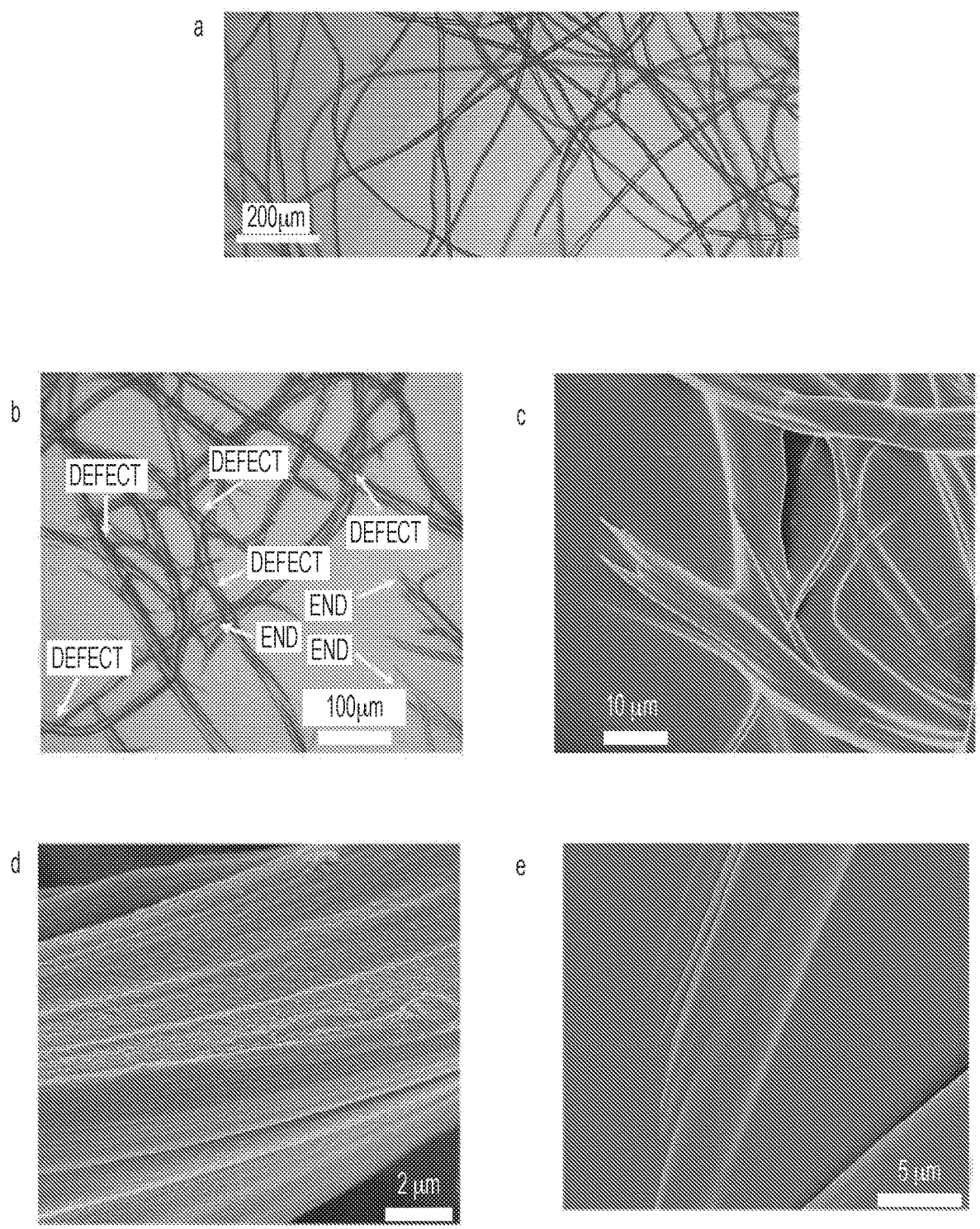

FIG. 30 shows the morphology changes of an exemplary silk fiber during the partial dissolution process. (a) Optical microscopy image of silk fiber after incubated in HFIP (weight ratio 1:30) at 60° C. for 2 hours. The image shows that the silk fibers are still intact, and no cleavage is observed. (b,c) Optical microscopy (b) and scanning electron microscopy (c) image of silk fiber after incubated in HFIP at 60° C. for 8 hours. These images show that silk fibers are split from ends and defects. (d,e) SEM images of SMF surface (d) and end (e). These two images indicate that the ends of SMFs are further split to sub-microfibril structures along the fiber axis direction, whereas other parts of silk microfibrils are still intact.

Figure 31:
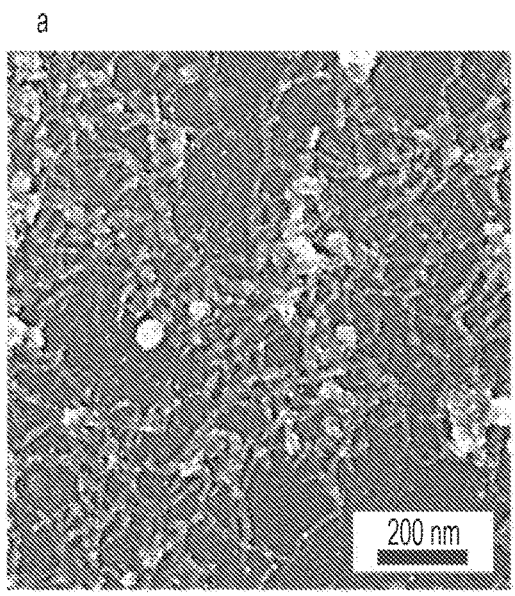
Figure 31:
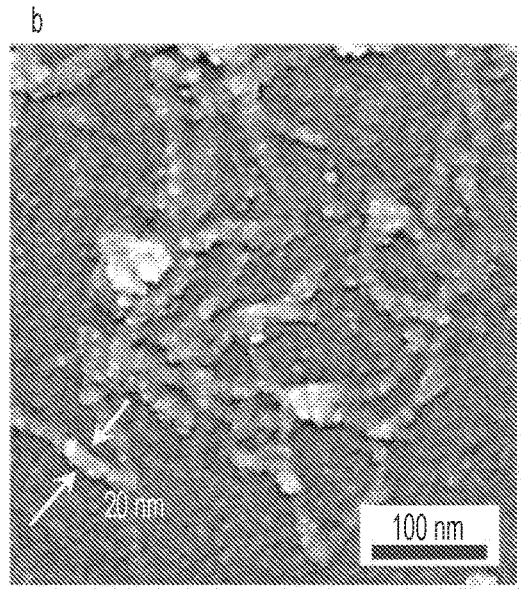
Figure 31:
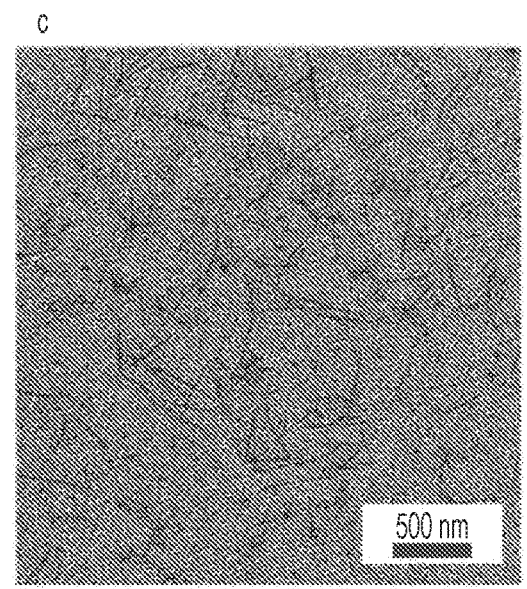
Figure 31:
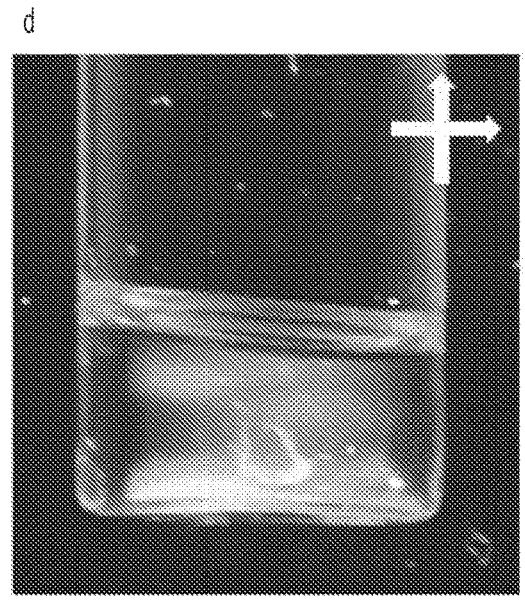
Figure 32:
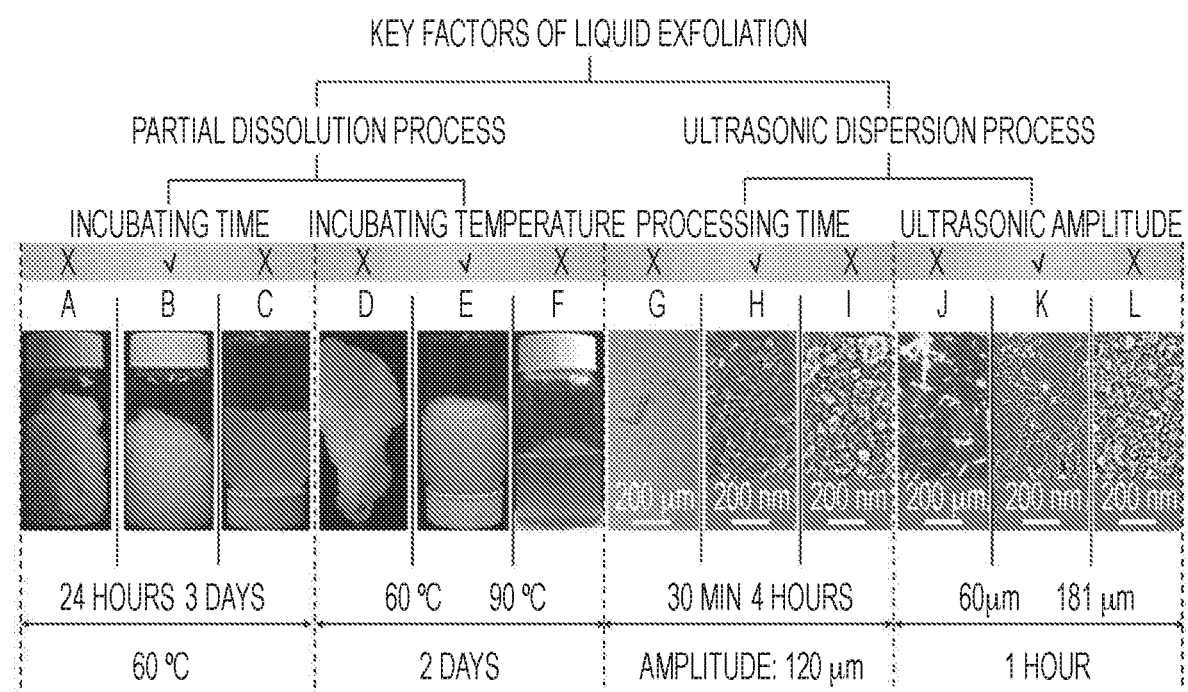

FIG. 31 shows visual appearance and structural characterization of an exemplary exfoliated SNFs. (a-b) SEM images of exfoliated SNFs at different magnifications. (c) Transmission electron microscopy (TEM) image of exfoliated SNFs. (d) Visual appearance of SNF suspension under cross-polarized light. The solution shows strong birefringent under polarized light, indicating the presence of a nematic phase of SNFs FIG. 32 shows exemplary factors affecting liquid exfoliation of silk fibers. There are two main stages in this exfoliation process. The first stage is partial dissolution of silk fibers. In this stage (a-f), the incubation time and temperature are two of the most important factors for successful exfoliation of silk fibers. The optimal incubation time to obtain SMF pulp (b) is from 24 hours to 3 days when the incubation temperature is set as 60° C. If the incubation time is less than 24 hours, the silk fibers are not totally dissolved to SMFs (a). If the incubation time is longer than 3 days, most of the silk fibers are dissolved to silk solution (c). The optimal incubation temperature to harvest SMF pulp is 60-90° C. when the incubation time is set at 2 days (e). The partial dissolution ability of HFIP for silk fibers increases with increasing incubation temperature. If the incubation temperature is too low (37° C. for example, as shown in d), the silk fibers are not totally dissolved to SMFs and can be moved intact from the bottle. On the other hand, if the incubation temperature is too high (90° C. for example, as shown in f), most of the silk fibers are dissolved to silk solution. The second stage is the ultrasonic dispersion process. In this stage (g-l), the ultrasonic process time and amplitude are two of the most important factors to extract SNFs from SMFs. Notably, different ultrasonic devices have different setups, thus have different conditions for optimal exfoliation of SMFs. Here the optimum conditions were basing on a Branson Digital 450 Sonifier. The effective window for exfoliation of SMFs was in the range of 30 min to 4 hours (h) when the amplitude is fixed at 120 μm. If the ultrasonic time is less than 30 min (20 min for example, as shown in g), most of SMFs are still intact. By increasing the ultrasonic process time, more SMFs can be exfoliated, but if the ultrasonic process time is longer than 4 hours the silk fibers are more likely to be exfoliated to nanoparticles (i). In terms of ultrasonic amplitude, the best setting to extract SNFs was 60-181 μm (k) when the ultrasonic time was set at 1 hour. The larger the amplitude applied the more SNFs can be extracted, but similar with the effect of ultrasonic time, more silk nanoparticles will also result (l).

Figure 33:
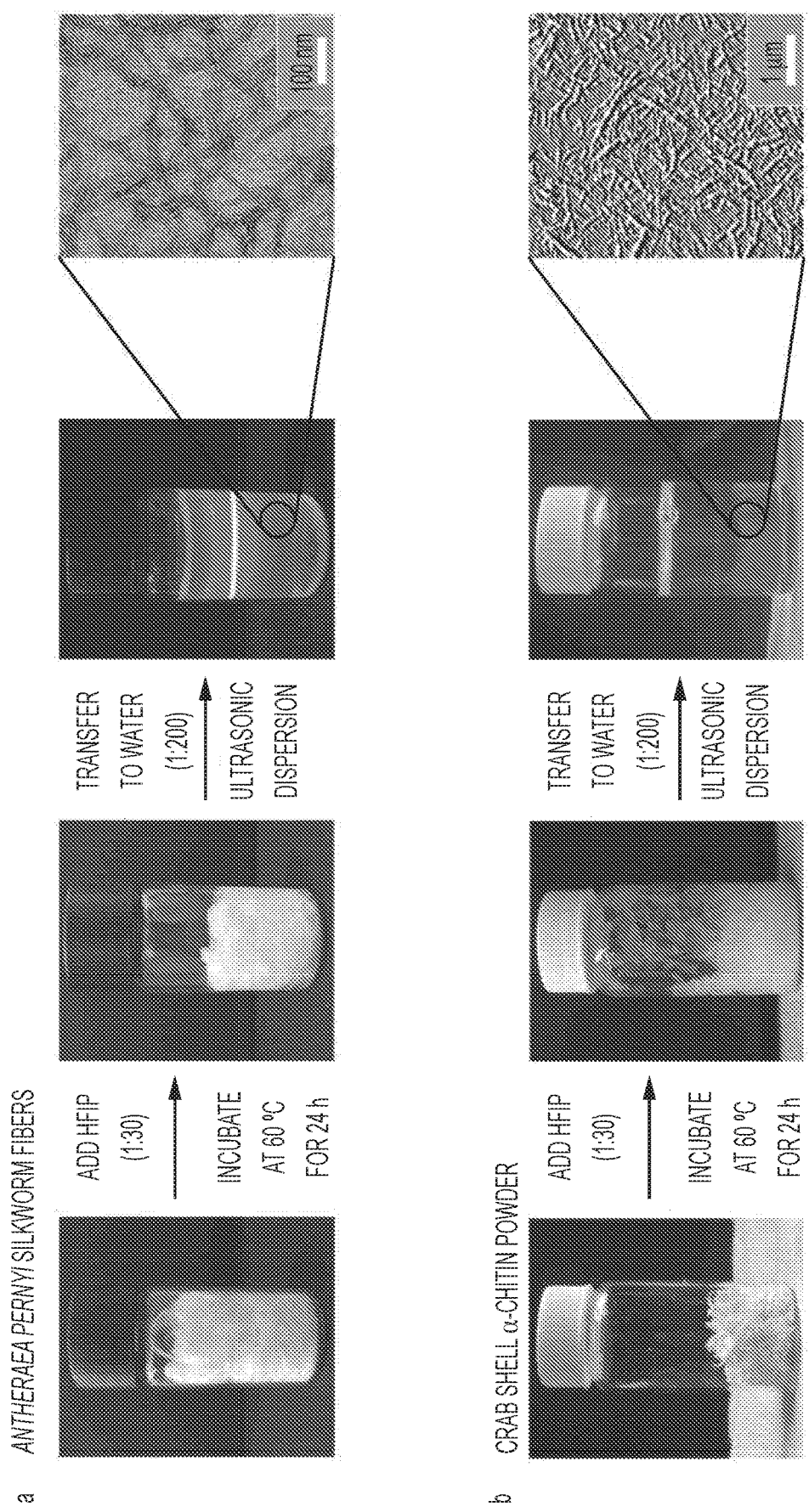

FIG. 33 shows creation of exemplary biological nanofibrils by using HFIP based liquid exfoliation method. (a) *Antheraea pernyi* silk nanofibrils are extracted from the degummed *Antheraea pernyi* silkworm silk fibers by using HFIP based liquid exfoliation method. (b) Chitin nanofibrils are extracted from the Crab shell α-chitin powder through HFIP based liquid exfoliation method.

Figure 34:
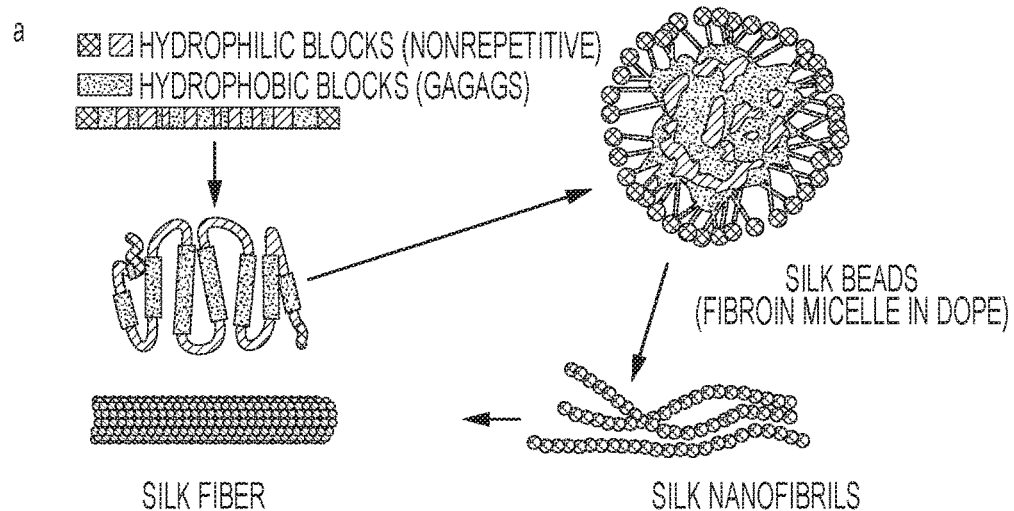
Figure 34:
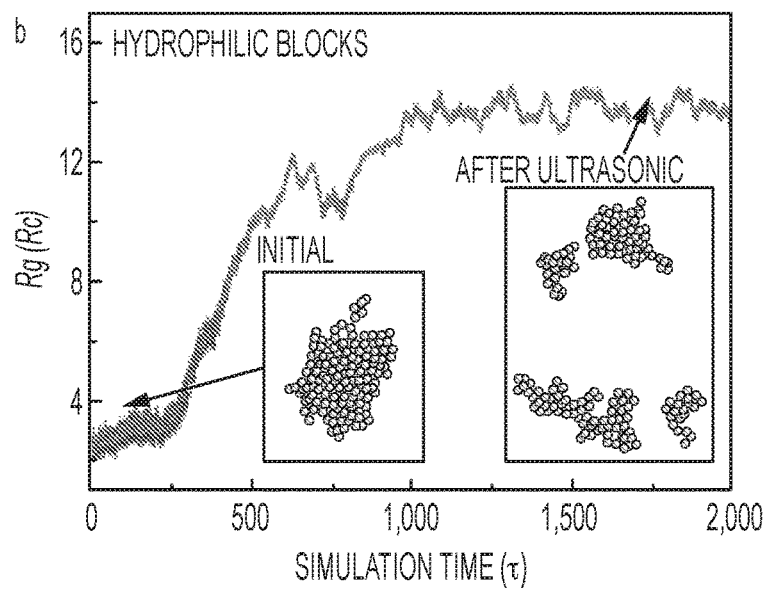
Figure 34:
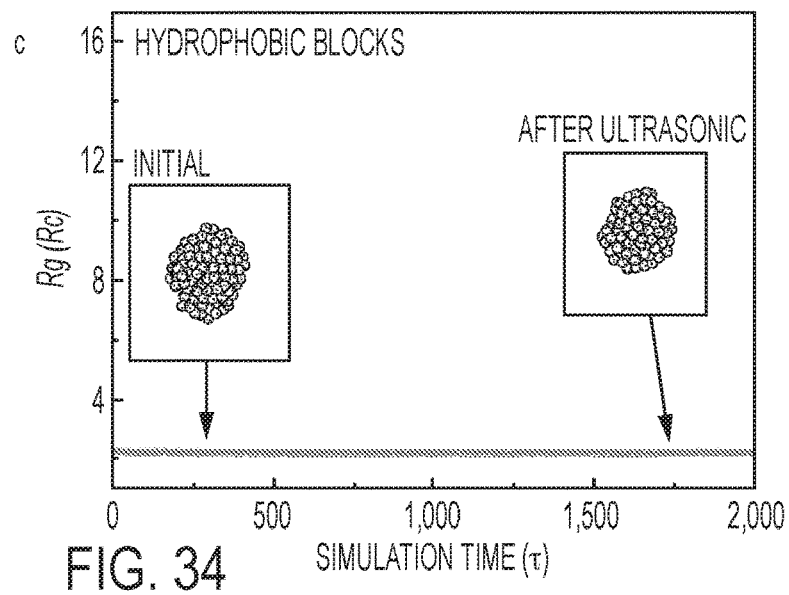

FIG. 34 shows the potential exfoliation mechanism disclosed through DPD simulation. (a) Model of hierarchical self-assembly and structures of *B. mori* silk fibers. (b) The radius of gyration (Rg) of the hydrophilic chains as a function of simulation time. The increase indicates the initial collection of chains falls apart under ultrasonication (insets). (c) The Rg of the hydrophobic chains remains constant with simulation time. Snapshots show that the collection of chains does not fall apart under ultrasonication (insets).

Figure 35:
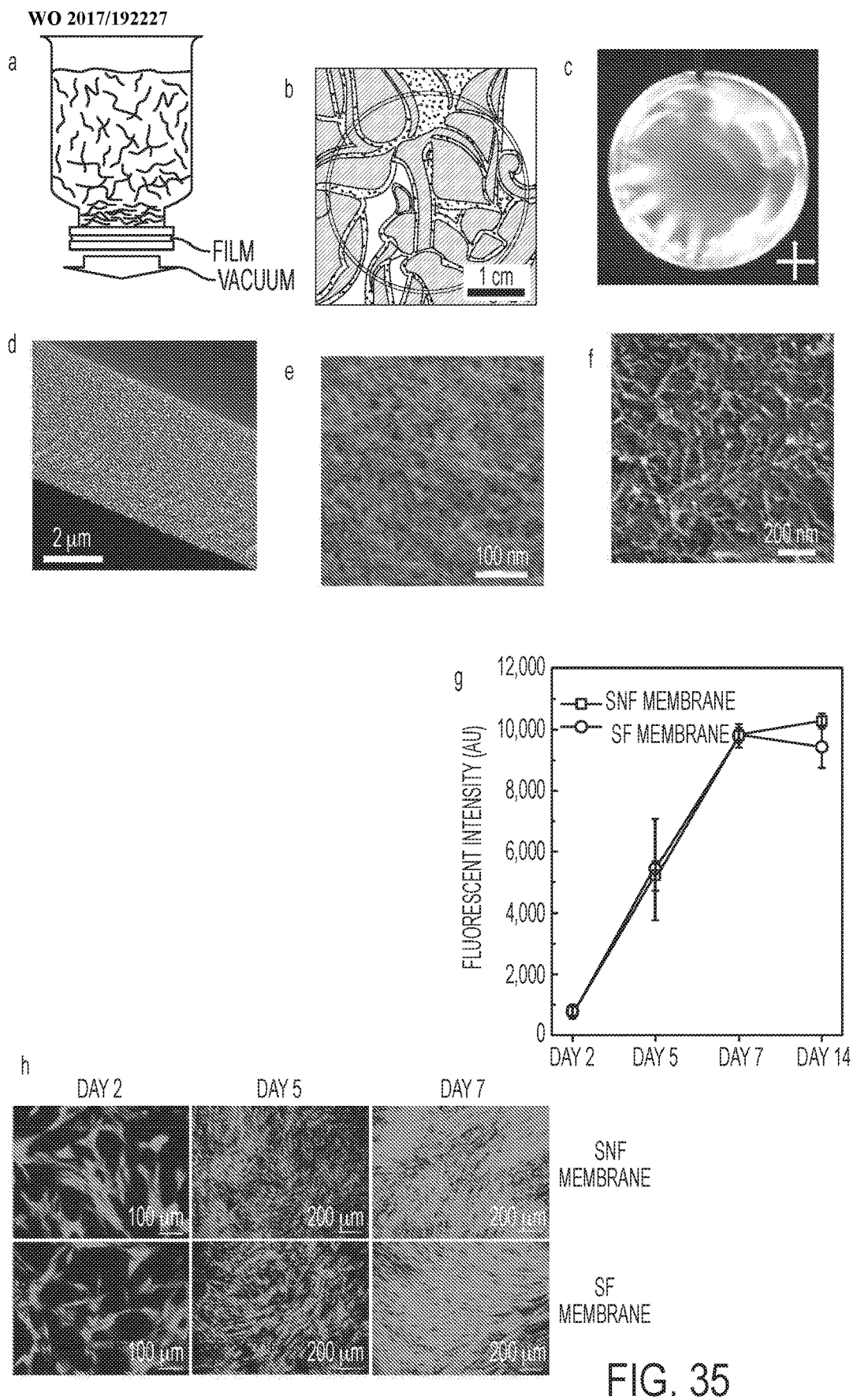

FIG. 35 shows visual appearance, structural characterization and cell response of certain exemplary SNF membranes. (a) Schematic illustration of SNF membrane fabrication via vacuum filtration. (b, c) pictures of the SNF membranes under visual (b) and cross-polarized light (c). In (b), the membrane was layed on a colorful cloth, showing its fully transparency. (d) A cross-sectional SEM image of SNF membrane. (e, f) The top view (e) and cross-sectional (f) SEM of SNF membrane under high magnification. (g, h) Cell responses on SNF membranes and SF membranes (control). (g) Alamar blue (metabolic activity) analysis of HDF proliferation over 14 days. Data are mean±SD, n=4. (h) Fluorescent imaging of live/dead staining of HDFs grown on silk membranes on days 2, 5 and 7.

Figure 36:
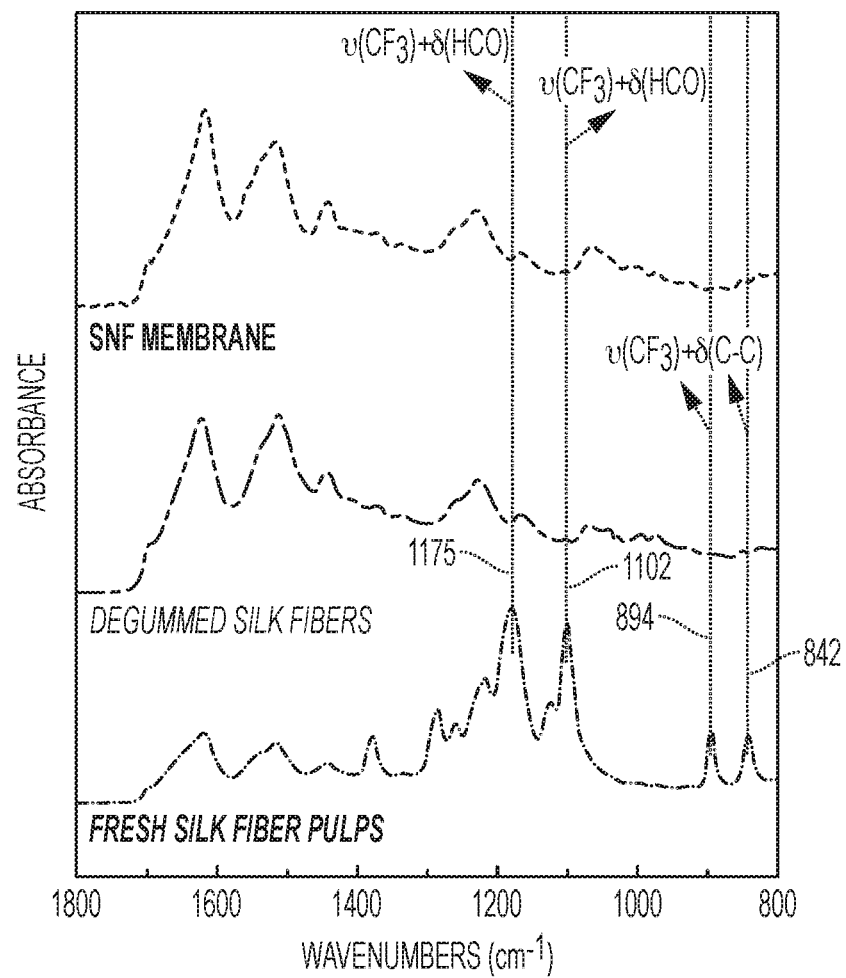

FIG. 36 shows FTIR spectra of exemplary fresh silk fiber pulps (e.g., which is just moved from HFIP after incubating at 60° C. for 24 hours), degummed silk fibers and SNF membrane. Compared with FTIR spectrum of silk fiber pulps, which shows strong HFIP specific peaks at 1175, 1102, 894 and 842 $cm^{-1}$, the FTIR spectrum of SNF membrane is very similar with the degummed silk fibers. No HFIP specific absorption is detected, indicating HFIP is totally removed from the SNF membranes.

Figure 37:
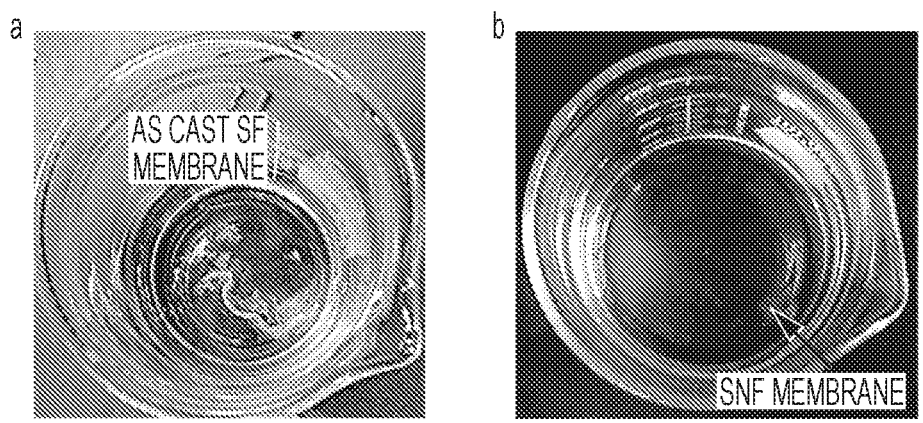

FIG. 37 shows photographs of exemplary SNF and as cast silk fibroin (SF) membranes with a thickness of about 5 μm immersed in water. (a) As cast SF membrane immersed in water for 5 mins at room temperature; (b) SNF membrane immersed in water for 1 week at room temperature. In order to observe the SNF membrane more clearly in water, blue light was used to irradiate the beaker.

Figure 38:
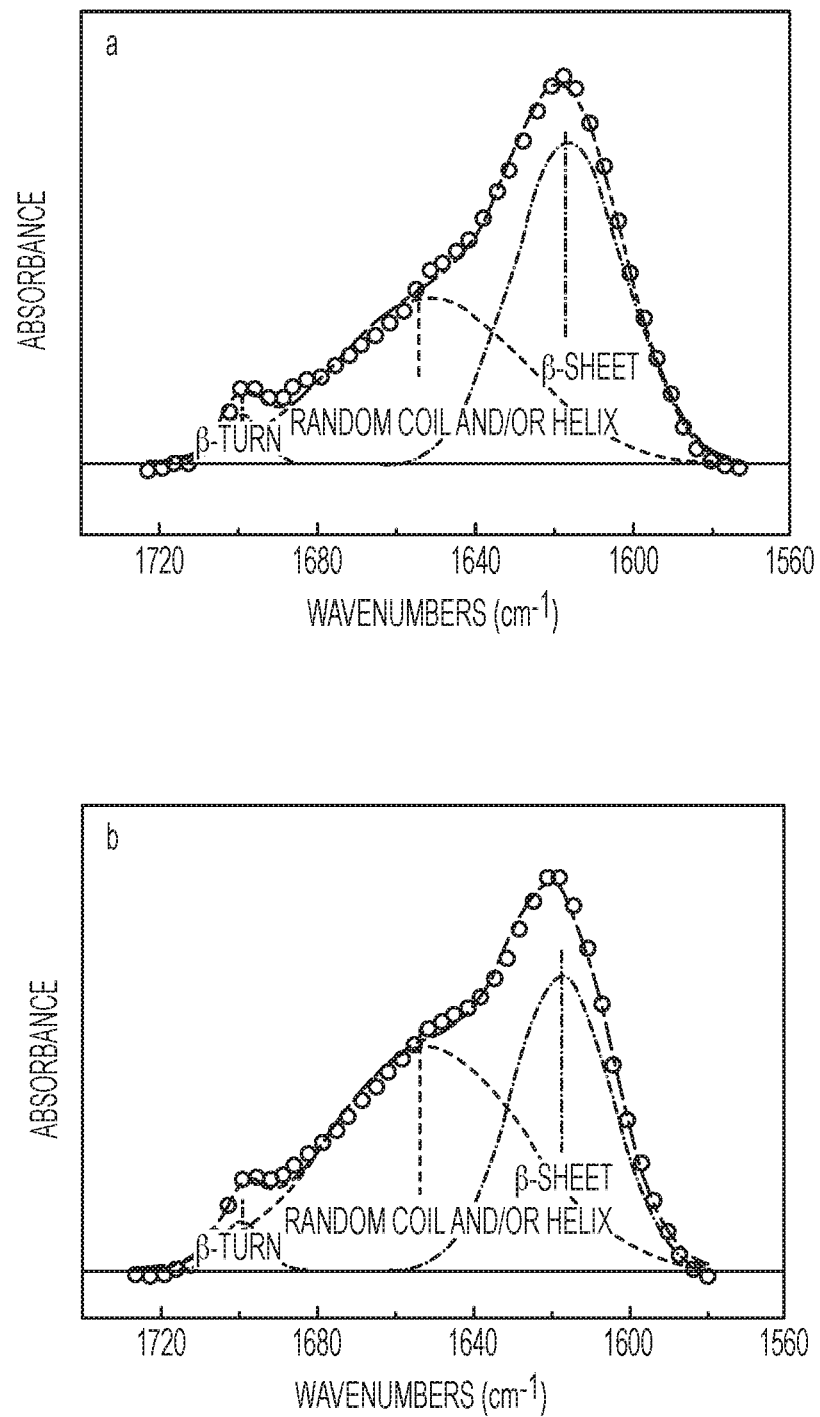

FIG. 38 shows deconvolution of the FTIR amide I band of exemplary SNF membranes and degummed silk fibers. (a) SNF membrane; (b) Degummed silk fibers.

Figure 39:
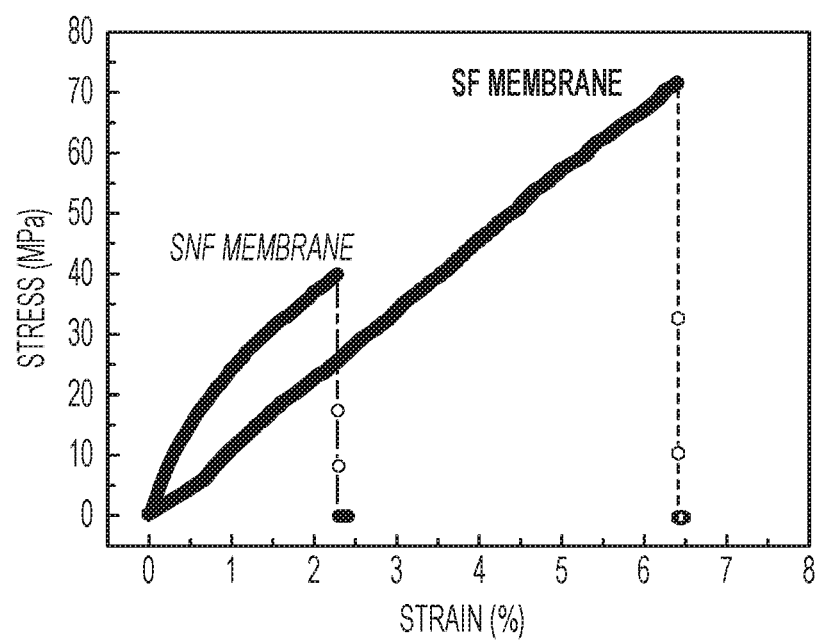

FIG. 39 shows typical tensile stress-strain curves of the exemplary SNF and 70 vol % ethanol treated SF membranes with a thickness about 200 μm at relative humidity of 50%.

Figure 40:
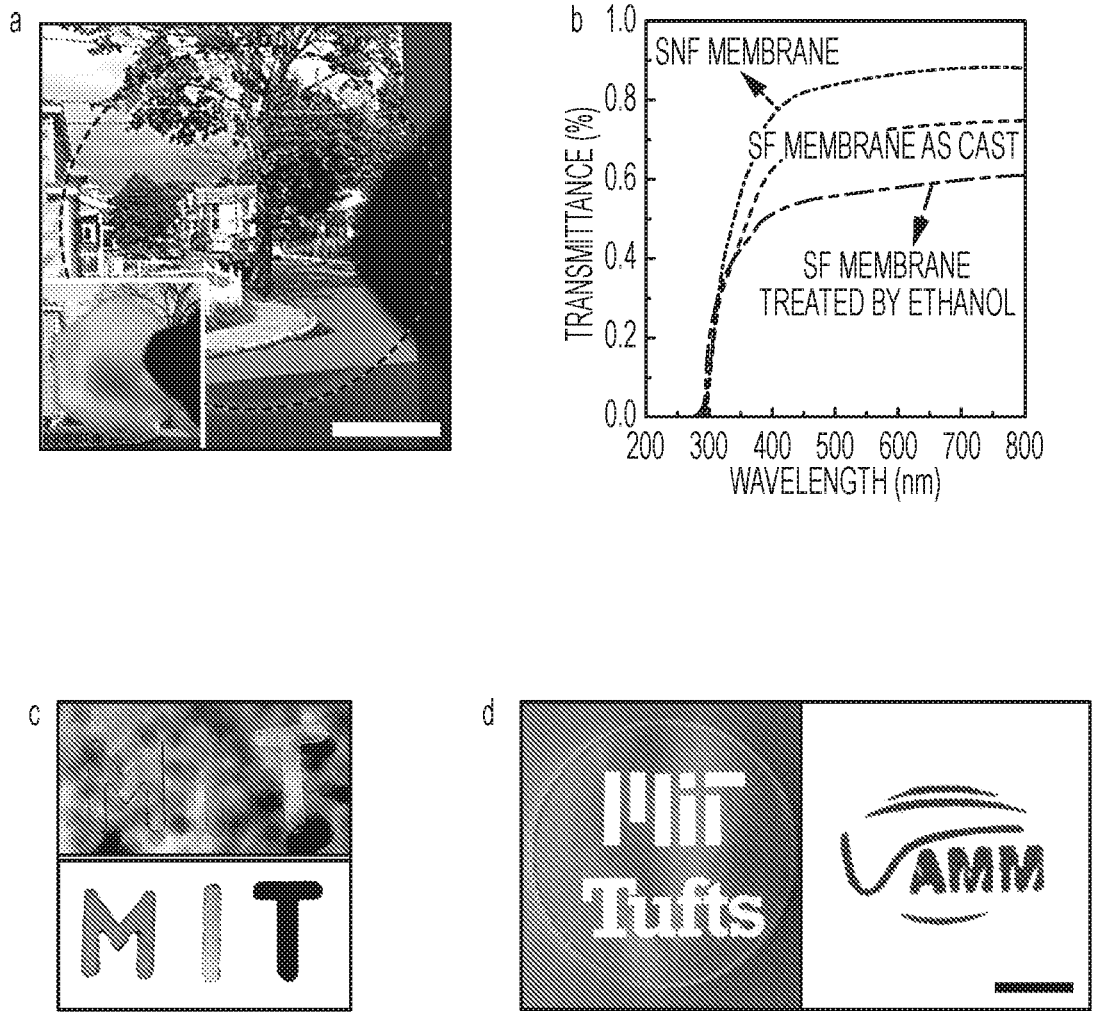

FIG. 40 shows exemplary SNF based optical membranes. (a) A photograph to illustrate the transparency of SNF membrane. The insert is a photograph of a silk fibroin membrane after 70 vol % ethanol treatment. (b) UV-vis transmittance of silk fibroin (SF) and SNF membranes approximately 200 μm thick. (c) The fluorescent "MIT" letters fabricated by SNF membranes under visual (top) and UV light (bottom). Letter "M" and "T" were prepared by SNF/Rhodamine B and SNF/Rhodamine 123 dispersion, respectively; Letter "I" was prepared by SNF dispersion without any fluorescent dyes. (d) Quantum dots patterned SNF membrane under visual (left) and UV light (right). All scale bars are 1 cm, (c) and (d) have same scale size.

Figure 41:
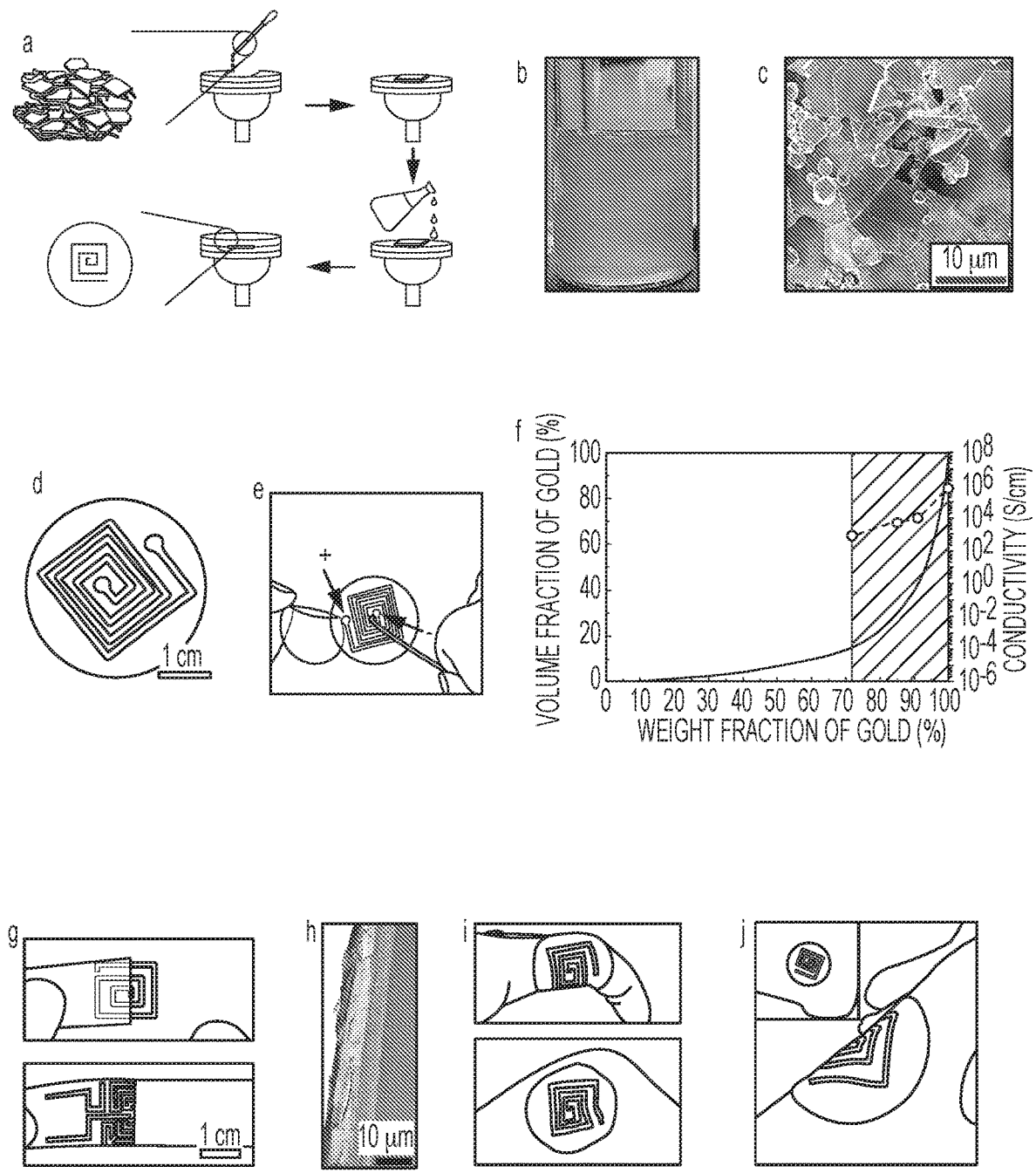

FIG. 41 shows exemplary SNF based flexible electronic devices. (a) Schematic of the pathway followed to design SNF based electronic devices. (b) Picture shows the macroscopic features of the suspension of SNF reduced gold single crystal nanoplatelets. (c) SEM of gold single crystal nanoplatelets. (d) Picture of gold single crystal nanoplatelets (92 wt %) patterned SNF membranes. (e) Picture of the pattern formed by 92 wt % gold single crystal nanoplatelets as conductor. (f) Non-linear relationship between the weight and volume composition of gold in the hybrid membranes and in-plane conductivity versus composition. The striped region highlights the conductive regime. The remaining composition regime has conductivity below 10-8 S cm-1. (g) Comparison of the binding between conductive layer and substrate of SNF membrane based electronic devices (weight ratio of gold nanoplatelets in the conducting layer is 74%) and transfer printed gold/silk membranes. (h) Cross-sectional SEM images of SNF based flexible electronic devices. False color was used to distinguish the gold nanoplatelet layer and SNF substrate. (i) Photographs to show that SNF membrane based electronic device could attach to the finger with glove (top) and skin of chicken wing (bottom) under 85% RH. (j) shows the attached SNF membrane based flexible electronic devices deformed with the deformation of pig ear.

Figure 42:
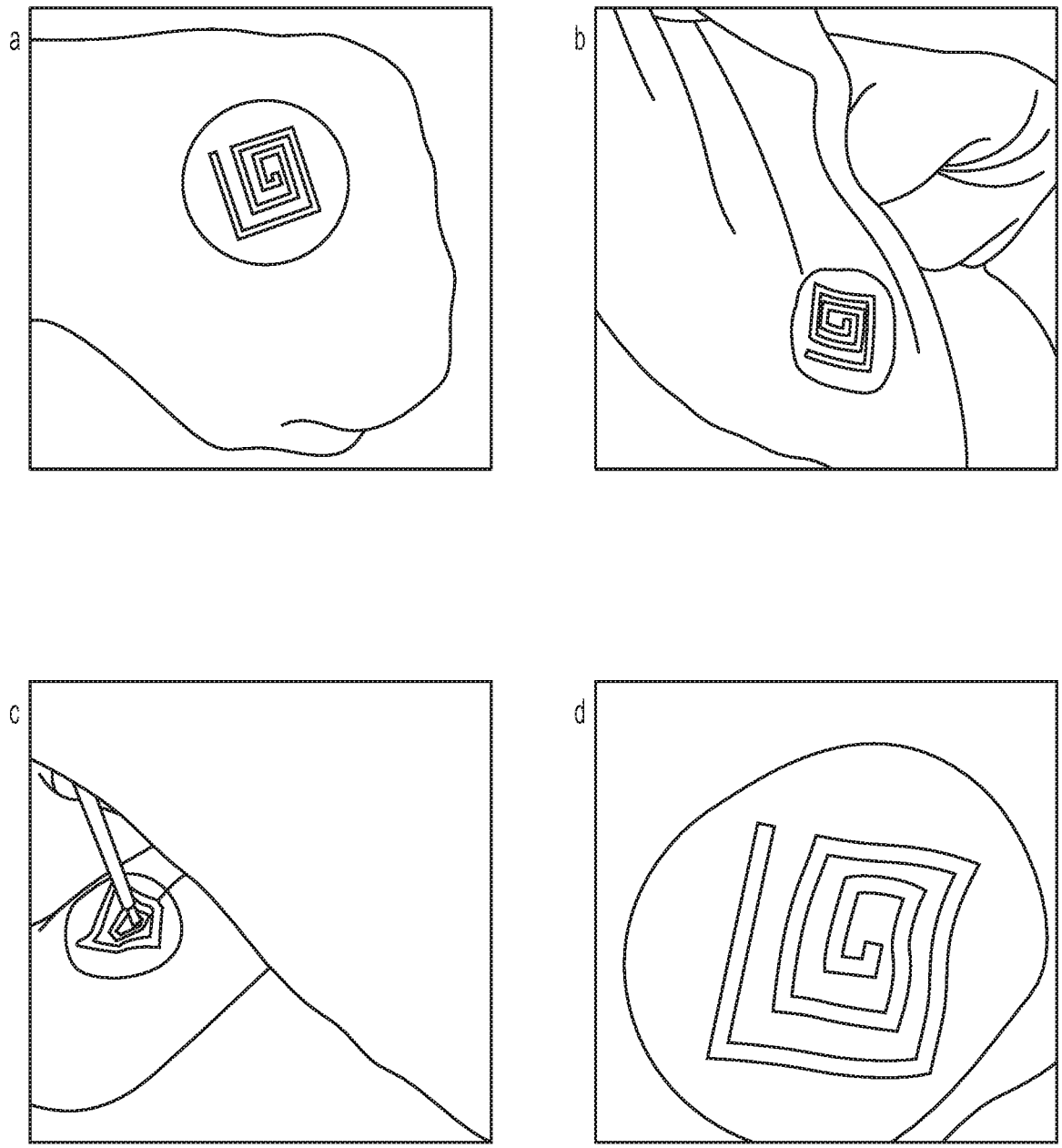

FIG. 42 shows photographs of exemplary SNF based electronic device attached to glove, pork ear skin and chicken wing skin under 85% RH. (a) the membrane was touched on the back of the hand with rubber gloves. (b) the membrane was attached on pig ear skin and deformed with skin in inside direction. (c) the attached membrane was poked by rod. (d) the photograph to show that membrane remains undamaged after poking.

DEFINITIONS

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) all numerical ranges provided herein are understood to include all possible incremental sub-ranges within the outer boundaries of the range. Thus, a range of 30 to 90 units discloses, for example, 35 to 50 units, 45 to 85 units, and 40 to 80 units, etc. In addition, endpoints of any ranges are included. Unless otherwise defined, percentages are wt/wt %.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is manmade in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Associated with: Two events or entities are "associated" with one another, as that term is used herein, if the presence, level and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biocompatible: The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

Biodegradable: As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition", as used herein, may be used to refer to a discrete physical entity that comprises one or more specified components. In general, unless otherwise specified, a composition may be of any form—e.g., gas, gel, liquid, solid, etc.

Encapsulated: The term "encapsulated" is used herein to refer to substances that are completely surrounded by another material.

"Improve," "increase", "inhibit" or "reduce": As used herein, the terms "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components (e.g., with which it was associated when initially produced, whether in nature and/or in an experimental setting). In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Physiological conditions: as used herein, has its art-understood meaning referencing conditions under which cells or organisms live and/or reproduce. In some embodiments, the term refers to conditions of the external or internal milieu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20-40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

DETAILED DESCRIPTION

The present invention, according to various embodiments, is based, in part, on the surprising realization that extended exposure to polar organic solvents results in partial degradation of native silk fibers such that microfibrils produced thereby are able to retain much of the hierarchical structure of native silk fibers, without the need for expensive, complicated, and even harmful post-treatments. As a result, some embodiments of provided methods allow for the preparation of degummed (i.e., substantially sericin depleted) silk microfibrils which include much of the hierarchical structures of native silk fibers (see FIG. 11, panels a and b, and FIG. 28), for example, a nematic structure.

While certain polar organic solvents, such as HFIP, have been used in general with silk previously, such uses were significantly different than those described herein, In part, previously known methods of using HFIP with silk required a variety of dissolution, dialysis, concentrating, lyophilizing, and/or resuspending steps not required in the present invention. In addition, previously understood methods of using HFIP with silk included application of HFIP to powders of silk fibroin, which was made from a silk solution, not to native fibers themselves as with many embodiments of provided methods. Thus, previous methods could not maintain the hierarchical structures of native silk fibers, at least because the native silk fibers used therein had been dissolved into silk fibroin molecules, unlike in several embodiments of provided methods. In addition, many of the previously described uses of HFIP included incubation times much lower than those of many embodiments of provided methods. Many of the previously known methods include one or more steps that would destroy the hierarchical structures exhibited by many embodiments of provided compositions (e.g., a nematic structure).

In accordance with various embodiments, provided methods include exposing native silk fibers to one or more polar organic solvents for an extended period of time (e.g., at least 8 hours). In some embodiments, the present invention also provides methods of making exfoliated silk microfibrils including the step of exposing a degummed native silk fiber to a polar organic solvent for a period of time to produce a solution comprising exfoliated silk microfibrils comprising a nematic structure.

Native Silk Fibers

As used herein, the term "native silk fibers" means silk fibers provided from any silk producing animal, or via genetic engineering techniques able to replicate such structures (either directly or through genetic modification of, for example, bacteria, yeast, plants, and/or animals). Any type of silk fiber can be used according to aspects of the present invention. There are many different types of silk produced by a wide variety of species, including, without limitation: *Antheraea mylitta; Antheraea pernyi; Antheraea yamamai; Galleria mellonella; Bombyx mori; Bombyx mandarina; Galleria mellonella; Nephila clavipes; Nephila senegalensis; Gasteracantha mammosa; Argiope aurantia; Araneus diadematus; Latrodectus geometricus; Araneus bicentenarius; Tetragnatha versicolor; Araneus ventricosus; Dolomedes tenebrosus; Euagrus chisoseus; Plectreurys tristis; Argiope trifasciata*; and *Nephila madagascariensis*. In some embodiments, fibroin is obtained from a solution containing a dissolved silkworm silk or spider silk. The silkworm silk protein is obtained, for example, from *Bombyx mori*, and the spider silk is obtained from *Nephila clavipes*. Other silks include transgenic silks, genetically engineered silks (recombinant silk), such as silks from bacteria, yeast, mammalian cells, transgenic animals, or transgenic plants, and variants thereof. See for example, WO 97/08315 and U.S. Pat. No. 5,245,012, content of both of which is incorporated herein by reference in its entirety. In some embodiments, silk fibers may be provided or derived from other sources such as spiders, other silkworms, bees, synthesized silk-like peptides, and bioengineered variants thereof. In some embodiments, silk fibroin can be extracted from a gland of silkworm or transgenic silkworms. See for example, WO2007/098951, content of which is incorporated herein by reference in its entirety. Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Ala-rich" and "Gly-rich" hydrophobic blocks are typically separated by segments of amino acids with bulky side-groups (e.g., hydrophilic spacers).

Degumming

In some embodiments, provided methods include a step of degumming (i.e., removing all or substantially all of the sericin from a silk material). In some embodiments, provided compositions comprise no sericin or substantially no sericin. For example, in some embodiments, a silk fibroin solution can be prepared by any conventional method known to one skilled in the art. According to various embodiments, the solution is an aqueous solution. By way of non-limiting example, *B. mori* cocoons are boiled for about 30 minutes in an aqueous solution. In some embodiments, the aqueous solution is about 0.02M $Na_2CO_3$, and cocoons are rinsed, for example, with water to extract the sericin proteins and the extracted silk is then dissolved in an aqueous salt solution. Exemplary salts useful for this purpose include, but are not limited to, lithium bromide, lithium thiocyanate, calcium nitrate, and/or other chemicals capable of solubilizing silk. In some embodiments, extracted silk is dissolved in about 9-12 M LiBr solution, and the salt is consequently removed using, for example, dialysis.

In some embodiments, a silk solution may then be concentrated using, for example, dialysis against a hygroscopic polymer, for example, PEG, a polyethylene oxide, amylose or sericin. In some embodiments, PEG is of a molecular weight of 8,000-10,000 g/mol and has a concentration of 25-50%. In some embodiments, any dialysis system can be used. In some embodiments, dialysis may be for a time period sufficient to result in a final concentration of aqueous silk solution between 4-35%, for example, dialysis for 2-12 hours.

Polar Organic Solvents

In accordance with various embodiments, provided methods include the use of one or more polar organic solvent. In accordance with various embodiments, any application appropriate polar organic solvent(s) may be used. By way of non-limiting example, in some embodiments, the polar organic solvent is selected from the group consisting of hexafluoro-2-propanol, lithium bromide, calcium chloride, ethanol, formic acid, 1-ethyl-3-methylimidazolium acetate, triethylammonium phosphate (TeaH2PO4), triethylammonium lactate, (TeaLa), triethylammonium triflate, and triethylammonium mesylate.

As described herein, one unique feature of some embodiments of provided methods is that native silk fibers are exposed to one or more polar organic solvents for an extended period of time (e.g. longer than 8 hours). In some embodiments, the exposing step continues for at least 24 hours (e.g., 25 hours, 36 hours, 48 hours, 60 hours, 72 hours, 84 hours, 96 hours, 108 hours, 120 hours, or more). In some embodiments, the exposing step continues for at least 1 week (e.g., at least two weeks, three weeks, or more). In some embodiments, the exposing step continues for at least 10 days (e.g., at least 11 days, 12 days, 13 days, 14 days, 15 days, 16 days, 17 days, 18 days, 19 days, 20 days, 21 days or more). In some embodiments, the exposing step continues for at least 1 month (e.g, at least 2 months, 3 months, 4 months, 5 months, 6 months, or more). In some embodiments, the exposing step continues for between 8 hours and 21 days; 1 day and 21 days; 2 days, and 21 days; 3 days and 21 days; 7 days and 14 days.

In some embodiments, provided methods include exposing native silk fibers to at least one polar organic solvent at a temperature at or above normal room temperature (i.e., approximately 37° C.). In some embodiments, the exposing step occurs at a temperature at or above 40° C. (e.g., above 50° C., above 55° C., above 60° C.). In some embodiments, the exposing step occurs at a temperature between 40° C. and 60° C., inclusive.

In accordance with several embodiments, the use of temperatures at or above normal room temperature may result in the evaporation of some or much of the polar organic solvent during the exposing step. As such, in some embodiments, it can be helpful to perform provided methods in a system capable of capturing any evaporated polar organic solvent. In some embodiments, such collection may be helpful in the maintaining the appropriate conditions for the exposing step itself (or other steps in some embodiments of provided methods), where as in some embodiments, such collection may be due, at least in part to safety or other reasons. Regardless, in some embodiments, the exposing step occurs in a closed environment (e.g., using an airtight container).

According to any of a variety of embodiments, provided methods allow for the use of a wide range of silk fiber to polar solvent ratios. In some embodiments, the ratio of silk fiber to polar organic solvent is between 1:10 and 1:100 by weight (e.g., 1:20 to 1:100; 1:30 to 1:100; 1:40 to 1:00; 1:50 to 1:100; 1:60 to 1:100, 1:70 to 1:100; 1:80 to 1:100, 1:90 to 1:100; 1:10 to 1:90; 1:10 to 1:80; 1:10 to 1:70; 1:10 to 1:60; 1:10 to 1:50; 1:10 to 1:40; 1:10 to 1:30; 1:10 to 1:20, etc), inclusive. Without wishing to be held to particular theories, it is contemplated that if the ratio of silk to polar organic solvent is too low, the native silk fibers may be completely dissolved (e.g., to individual fibroin molecules), while if the ratio of silk to polar organic solvent is too high, the polar organic solvent may not be able to adequately penetrate the native silk fibers to partially dissolve them as described herein.

Nanofibrils

The present invention also provides, in some embodiments, methods for producing silk nanofibrils. In fact, certain provided methods represent the first known methods for direct extraction of silk nanofibers from native silk fibers on the single nanofiber scale. For example, in some embodiments, provided methods include the steps of exposing a degummed native silk fiber to a polar organic solvent for a period of time to produce exfoliated silk microfibrils comprising a nematic structure, removing the organic solvent to produce a silk microfibril material, dispersing the silk microfibril material in an aqueous solution, and agitating the silk microfibril material to form a silk nanofibril dispersion.

Agitation

In accordance with various embodiments, some provided methods allow for the production of silk nanofibrils through, at least in part, agitation of provided silk microfibril materials. As will be appreciated by those of skill in the art, a variety of agitation methods are useful in accordance with particular embodiments. For example, in some embodiments, agitating may be or comprise at least one of sonication (e.g., ultrasonication), high pressure homogenization, comminuting, cryomilling/cryocrushing, and combinations thereof.

In some embodiments, provided methods further include removing undissolved silk fibers from the dispersed silk microfibril material prior to the agitation step. In some embodiments, the removing is accomplished by one or both of centrifugation and filtration. Without wishing to be held to a particular theory, it is contemplated that the presence of larger fibers (e.g., 1 cm or longer) may result in aggregation of the undissolved fibers and inhibit, or even prevent, proper agitation to produce silk nanofibrils.

Additional Processes

In some embodiments, provided methods further include extruding the exfoliated silk micro- or nano-fibrils to produce a regenerated silk fiber comprising a plurality of aligned silk micro- or nano-fibrils. According to various embodiments, an application-appropriate method(s) for extrusion may be used. For example, in some embodiments, extrusion may be or comprise one or more of electrospinning, microfluidic extrusion (e.g., 3d printing), wet-spinning, dry-spinning, and/or direct winding. In some embodiments, provided exfoliated micro- or nano-fibrils and/or regenerated silk fibers may be used to produce mats, hydrogels, fibers, scaffolds, membranes/films (e.g., filtration membranes or transparent substrate membranes), implants, sensors, and/or adsorbing materials.

In some embodiments, provided methods further include removing the organic solvent to produce a silk micro- or nano-fibril material, dispersing the silk micro- or nano-fibril material in an aqueous solution to form a silk micro- or nano-fibril dispersion. In some embodiments, such provided silk micro- or nano-dispersions may be used for or in gels (e.g., hydrogels), microparticles, drug carriers, and/or as templates for inorganic crystal growth.

Depending on the application, in some embodiments, a conformational change can be induced in the silk micro- or nano-fibril (e.g., fibroin) in a provided composition to control the solubility of the silk fibroin composition/article. In some embodiments, the conformational change can induce the silk fibroin to become at least partially insoluble. Without wishing to be bound by a particular theory, it is contemplated that the induced conformational change alters the crystallinity of the silk fibroin, e.g., Silk II beta (β)-sheet crystallinity. The conformational change can be induced by any methods known in the art, including, but not limited to, alcohol immersion (e.g., ethanol, methanol), water annealing, shear stress, ultrasound (e.g., by sonication), pH reduction (e.g., pH titration and/or exposure to an electric field) and any combinations thereof. For example, the conformational change can be induced by one or more methods, including but not limited to, controlled slow drying (Lu et al., Biomacromolecules 2009, 10, 1032); water annealing (Jin et al., 15 Adv. Funct. Mats. 2005, 15, 1241; Hu et al., Biomacromolecules 2011, 12, 1686); stretching (Demma & Asakura, Biotech & Bioengin. 1989, 33, 598); compressing; solvent immersion, including methanol (Hofinann et al., J Control Release. 2006, 111, 219), ethanol (Miyairi et al., J. Fermen. Tech. 1978, 56, 303), glutaraldehyde (Acharya et al., Biotechnol J. 2008, 3, 226), and 1-ethyl-3-(3-dimethyl aminopropyl) carbodiimide (EDC) (Bayraktar et al., Eur J Pharm Biopharm. 2005, 60, 373); pH adjustment, e.g., pH titration and/or exposure to an electric field (see, e.g., U.S. Patent App. No. US2011/0171239); heat treatment; shear stress (see, e.g., International App. No.: WO 2011/005381), ultrasound, e.g., sonication (see, e.g., U.S. Patent Application Publication No. U.S. 2010/0178304 and International App. No. WO2008/150861); and any combinations thereof. Contents of all of the references listed above are incorporated herein by reference in their entireties. In some embodiments, provided methods and compositions may include β-sheet formation. In some embodiments, provided composition include no or substantially no β-sheet.

In some embodiments, the provided compositions/articles can be treated by annealing. As used herein, the process of annealing involves inducing formation of β-sheet secondary structure in the silk fibroin of provided micro- or nanofibrils. This can be due to increased non-covalent interactions of silk fibroin. Such non-covalent interactions can include intra-molecular interactions, inter-molecular interactions, or both. Typically, non-covalent interactions are mediated by hydrogen bonds, which lead to increased β sheet formation. Upon reaching a certain critical level of β sheet secondary structure, silk fibroin is rendered insoluble, e.g., in an aqueous environment. This phenomenon is generally referred to as crystallinity and the status of such silk fibroin is referred to as Silk II. Thus, "annealing" involves a conformation change of silk fibroin to β-sheet dominated (silk II) conformation, such that silk fibroin is crystalized and thus insoluble. Without wishing to be bound by a theory, it is believed that this conformational change is due to hydrogen-bonding and/or hydrophobic interactions mediated structural shift of silk fibroin to a higher β sheet content.

After the treatment to induce the conformational change, provided compositions may comprise a silk II β-sheet crystallinity content of at least about 30%, at least about 40%, at least about 50%, at least about 60%, at least about 70%, but not more than about 80%. In some embodiments, provided compositions comprise β-sheet crystallinity of at least 30%, e.g., 35%, 40%, 45%, 50%, 55%, 60%, 65%, 70%, 75%, 70%, but not more than about 80%. In some embodiments, provided compositions comprise β-sheet crystallinity of less than 80%. In some embodiments, provided compositions comprise β-sheet crystallinity of more than 30%. In some embodiments, provided compositions comprise β-sheet crystallinity of between 30-80% (e.g., between 40-60%).

One advantage of certain provided methods is that the micro- and/or nano-fibers produced thereby do not require any post-processing treatments in order to provide useful silk micro- and/or nano-fibrils, unlike previously known methods. In some embodiments, the silk microfibrils and/or nanofibrils are not subjected to any post-processing treatment. In some embodiments, the post-processing treatment is selected from the group consisting of lyophilization, critical point drying, and heat drying.

In some embodiments, provided silk compositions described herein, and methods of making and/or using them may be performed in the absence of any organic solvent. Thus, in some embodiments, provided compositions and methods are particularly amenable to the incorporation of labile molecules, such as bioactive agents or therapeutics, and can, in certain embodiments, be used to produce controlled release biomaterials. In some embodiments, such methods are performed in water only.

Exemplary Compositions

As describe in part above, the present invention, in some aspects, provides compositions including a solution comprising a plurality of exfoliated silk microfibrils, wherein the microfibers are characterized as having a substantially nematic structure. In some embodiments, the present invention provides compositions including a plurality of exfoliated silk microfibrils comprising a nematic structure (e.g., not in solution).

Aspects of the present invention may provide silk microfibrils with any of a variety of tailorable physical characteristics. In some embodiments, provided microfibrils may have a diameter between 1 and 100 µm (e.g., between about 2 and 100 µm; 5 and 100 µm; 10 and 100 µm; 20 and 100 µm; 30 and 100 µm; 40 and 100 µm; 50 and 100 µm; 60 and 100 µm; 70 and 100 µm; 80 and 100 µm; 90 and 100 µm; 5 to 90 µm; 10 to 90 µm; 5 to 80 µm; 10 to 80 µm; 5 to 70 µm; 10 to 70 µm; 5 to 60 µm; 10 to 60 µm; 10 to 50 µm, etc), inclusive. For example, in some embodiments, provided silk microfibrils have a diameter between 5 and 50 µm, inclusive. In some embodiment, provided silk microfibrils have a diameter of at least 1 µm. In some embodiment, provided silk microfibrils have a diameter of at least 10 µm. In some embodiment, provided silk microfibrils have a diameter of at most 100 µm. In some embodiment, provided silk microfibrils have a diameter of at most 50 µm.

In some embodiments, provided microfibrils may have a length between 1 µm and 100 mm (e.g., between about 10 µm and 100 mm; 100 µm and 100 mm; 1 mm and 100 mm; 1 µm and 10 mm; 1 µm and 1 mm; 10 µm to 1 mm; 100 µm to 1 mm, 1 µm to 10 µm, etc), inclusive. In some embodiments, provided silk microfibers have a length between 5 µm and 50 mm, inclusive. In some embodiments, provided silk microfibrils have a length of at least 1 µm. In some embodiments, provided silk microfibrils have a length of at least 10 µm. In some embodiments, provided silk microfibrils have a length of at least 100 µm. In some embodiments, provided silk microfibrils have a length of at least 1 mm. In some embodiments, provided silk microfibrils have a length of at most 100 mm. In some embodiments, provided silk microfibrils have a length of at most 10 mm. In some embodiments, provided silk microfibrils have a length of at most 1 mm.

In some embodiments, the present invention also provides compositions including a solution comprising a plurality of exfoliated silk nanofibrils, wherein the nanofibrils are characterized as having a substantially nematic structure. In some embodiments, the present invention provides compositions including a plurality of exfoliated nanofibrils comprising a nematic structure (e.g., not in solution).

In some embodiments, the silk nanofibrils have a diameter between 2 and 200 nm (e.g., between about 2 and 150 nm; 2 and 100 nm; 2 and 50 nm; 2 and 40 nm; 2 and 30 nm; 2 and 20 nm; 5 to 200 nm; 10 to 200 nm; 10 to 150 nm; 10 to 100 nm; 10 to 50 nm, etc), inclusive. In some embodiments, provided silk nanofibrils have a diameter of at least 2 nm. In some embodiments, provided silk nanofibrils have a diameter of at least 10 nm. In some embodiments, provided silk nanofibrils have a diameter of at least 50 nm. In some embodiments, provided silk nanofibrils have a diameter of at least 100 nm. In some embodiments, provided silk nanofibrils have a diameter of at most 200 nm. In some embodiments, provided silk nanofibrils have a diameter of at most 150 nm. In some embodiments, provided silk nanofibrils have a diameter of at most 100 nm. In some embodiments, provided silk nanofibrils have a diameter of at most 50 nm. In some embodiments, provided silk nanofibrils have a diameter of at most 20 nm.

In some embodiments, the silk nanofibrils have a length between 50 and 2,000 nm (e.g., between about 50 and 1,500 nm; 50 and 1,000 nm; 50 and 500 nm; 100 and 2,000 nm; 100 and 1,500 nm; 100 and 1,000 nm, 100 and 500 nm, 500 to 2,000 nm; 500 to 1,500 nm; 500 to 1,000 nm, etc), inclusive. In some embodiments, provided silk nanofibrils have a length of at least 50 nm. In some embodiments, provided silk nanofibrils have a length of at least 100 nm. In some embodiments, provided silk nanofibrils have a length of at least 200 nm. In some embodiments, provided silk nanofibrils have a length of at least 500 nm. In some embodiments, provided silk nanofibrils have a length of at least 1,000 nm. In some embodiments, provided silk nanofibrils have a length of at most 2,000 nm. In some embodiments, provided silk nanofibrils have a length of at most 1,500 nm. In some embodiments, provided silk nanofibrils have a length of at most 1,000 nm. In some embodiments, provided silk nanofibrils have a length of at most 500 nm.

In some embodiments, the present invention provides compositions including a plurality of exfoliated silk microfibrils and/or exfoliated nanofibrils which may be formed into, or added as a component of, for example, one or more articles. In some embodiments, a provided composition may be or comprise an article comprising a sensor, ultrafiltration membrane, adsorbent agent, flocculating agent, and/or implant. In some embodiments, provided compositions (e.g., articles) may be or comprise a wearable sensor. By way of non-limiting example, in some embodiments, provided compositions may be useful as sensors for food monitoring, oxygen monitoring, humidity monitoring, heart rate monitoring, and/or as temperature sensors. In some embodiments, provided compositions may be useful in electrical and/or optical devices, for example, in luminescent fibers with addition of dyes and/or in conductive fibers with in a core-shell structure (see Example 2).

In some embodiments, provided compositions/articles may be porous. For example, in some embodiments, provided compositions/articles can have a porosity of at least about 10%, at least about 20%, at least about 30%, at least about 40%, at least about 50%, at least about 60%, at least about 70%, at least about 80%, at least about 90%. As used herein, the term "porosity" is a measure of void spaces in a material and is a fraction of volume of voids over the total volume, as a percentage between 0 and 100% (or between 0 and 1). Determination of porosity is well known to a skilled artisan, e.g., using standardized techniques, such as mercury porosimetry and gas adsorption, e.g., nitrogen adsorption. As used herein, the term "porosity" is a measure of void spaces in a material and is a fraction of volume of voids over the total volume, as a percentage between 0 and 100% (or between 0 and 1). Determination of porosity is well known to a skilled artisan, e.g., using standardized techniques, such as mercury porosimetry and gas adsorption, e.g., nitrogen adsorption. In some embodiments, provided compositions/articles are non-porous or substantially non-porous.

According to various embodiments, provided porous compositions/articles can have any pore size. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section.

In some embodiments, the pores of provided porous compositions/articles can have a size distribution ranging from about 50 nm to about 1000 nm, from about 250 nm to about 500 nm, from about 500 nm to about 250 nm, from about 1 nm to about 200 nm, from about 10 nm to about 150 nm, or from about 50 nm to about 100 nm. In some embodiments, provided compositions/articles can be swellable when hydrated. The sizes of the pores can then change depending on the water content in the composition/article. In some embodiment, pores may be filled with a fluid such as water or air.

Methods for forming pores in compositions are known in the art and include, but are not limited, porogen-leaching methods, freeze-drying methods, and/or gas forming method. Exemplary methods for forming pores in a provided composition/article are described, for example, in U.S. Pat. App. Pub. No. US 2010/0279112 and No. US 2010/0279112; U.S. Pat. No. 7,842,780; and WO2004062697, contents of all of which are incorporated herein by reference in their entireties.

In accordance with various embodiments, provided compositions include micro- or nano-fibrils comprising hierarchical structures similar to or even substantially the same as native silk fibers. For example, in some embodiments, provided compositions comprise microfibrils having a helical or spiral structure.

In some embodiments, provided compositions comprising exfoliated microfibrils and/or exfoliated nanofibrils further include a substrate. Any application-appropriate substrate may be used in accordance with certain embodiments. For example, in some embodiments a substrate may be or comprise a conductive substance such as a wire, a slide, a film, microparticles, nanoparticles, a piece of equipment (e.g., a cell phone, printer cartridge, etc), an implant, a sensor, and combinations thereof.

In some embodiments, provided compositions comprising exfoliated microfibrils and/or exfoliated nanofibrils may further include one or more cells. In some embodiments, for example, the one or more cells may be selected from the group consisting of fibroblasts, stem cells, immune cells, nervous system cells, adipose tissue-derived cells, and blood cells.

According to various embodiments, provided compositions include silk micro- or nano-fibrils that approximate one or more of the desirable physical characteristics of native silk fibers. For example, in some embodiments, provided silk micro- or nano-fibers individually have an elongation at break, low temperature toughness, fracture mode, and/or one or more tensile properties that is/are substantially the same as a native silk fiber.

In accordance with various embodiments, provided compositions exhibit one or more advantageous properties. In some embodiments, provided compositions provide exfoliated microfibrils and/or nanofibrils with a high tensile strength (e.g., wherein a microfibril or nanofibril is able to support at least 10 times its own weight without break, for example at least 15, 20, 25, or 29 times its weight). In some embodiments, provided compositions provide exfoliated microfibrils and/or nanofibrils exhibit a high average modulus (e.g., greater than 8 GPa, for example, greater than 10, 11, 12, 13, 14, 15, 16, 17, 18, or 19 GPa).

Additives

Additionally, in some embodiments, provided compositions further include at least one additive. In some embodiments, provided compositions comprise two or more additives (e.g., 3, 4, 5, 6, 7, 8, 9, 10 or more).

Without wishing to be bound by a particular theory, according to various embodiments, an additive can provide one or more desirable properties, e.g., strength, flexibility, ease of processing and handling, biocompatibility, bioresorability, surface morphology, release rates and/or kinetics of one or more active additives present in the composition, and the like. An additive can be covalently or non-covalently linked with provided silk micro- and/or nano-fibrils and can be integrated homogenously or heterogeneously within the silk composition.

Without limitation, according to various embodiments, an additive can be selected from small organic or inorganic molecules; saccharides; oligosaccharides; polysaccharides; polymers; proteins; peptides; peptide analogs and derivatives; peptidomimetics; nucleic acids; nucleic acid analogs; and the like. In some embodiments, additives are or comprise immunogens; antigens; an extract made from biological materials such as bacteria, plants, fungi, or animal cells; animal tissues; naturally occurring or synthetic compositions; and any combinations thereof. Furthermore, the additive can be in any physical form. For example, the additive can be in the form of a particle, a fiber, a film, a gel, a mesh, a mat, a non-woven mat, a powder, a liquid, or any combinations thereof. In some embodiments, the additive is or comprises a particle (e.g., a microparticle or nanoparticle).

In some embodiments, an additive is a biocompatible polymer. Exemplary biocompatible polymers include, but are not limited to, a poly-lactic acid (PLA), poly-glycolic acid (PGA), poly-lactide-co-glycolide (PLGA), polyesters, poly(ortho ester), poly(phosphazine), poly(phosphate ester), polycaprolactone, gelatin, collagen, fibronectin, keratin, polyaspartic acid, alginate, chitosan, chitin, hyaluronic acid, pectin, polyhydroxyalkanoates, dextrans, and polyanhydrides, polyethylene oxide (PEO), poly(ethylene glycol) (PEG), triblock copolymers, polylysine, alginate, polyaspartic acid, any derivatives thereof and any combinations thereof.

In some embodiments, the at least one additive is or comprises a dye, a growth factor, an anti-inflammatory agent, an anti-microbial agent, quantum dots, luminescent materials, conductive polymers, and/or at least one inorganic material. In some embodiments, an inorganic material is or comprises a metal or ceramic material. In some embodiments, a metal is or comprises gold and/or silver. In some embodiments, a ceramic material may be or comprise hydroxyapatite, calcium carbonate, and/or silicon. In some embodiments, the at least one additive is or comprises carbon nanotubes. In some embodiments, the silk micro- or nano-fibrils comprise a coating (e.g., a single layer coating or multi-layered coating).

In some embodiments, an additive is a biologically active agent. The term "biologically active agent" as used herein refers to any molecule which exerts at least one biological effect in vivo. For example, a biologically active agent can be a therapeutic agent to treat or prevent a disease state or condition in a subject. Biologically active agents include, without limitation, organic molecules, inorganic materials, proteins, peptides, nucleic acids (e.g., genes, gene fragments, gene regulatory sequences, and antisense molecules), nucleoproteins, polysaccharides, glycoproteins, and lipoproteins. Classes of biologically active compounds that can be incorporated into the composition described herein include, without limitation, anticancer agents, antibiotics, analgesics, anti-inflammatory agents, immunosuppressants, enzyme inhibitors, antihistamines, anti-convulsants, hormones, muscle relaxants, antispasmodics, ophthalmic agents, prostaglandins, anti-depressants, anti-psychotic substances, trophic factors, osteoinductive proteins, growth factors, and vaccines.

In some embodiments, examples of additives include, but are not limited to: cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard 2003 Cell Mol Life Sci. January; 60(1):119-32; Hersel U. et al. 2003 Biomaterials. November; 24(24):4385-415); biologically active ligands; and substances that enhance or exclude particular varieties of cellular or tissue ingrowth. Other examples of additive agents that enhance proliferation or differentiation include, but are not limited to, osteoinductive substances, such as bone morphogenic proteins (BMP); cytokines, growth factors such as epidermal growth factor (EGF), platelet-derived growth factor (PDGF), insulin-like growth factor (IGF-I and II) TGF-β1, and the like.

In some embodiments, the total amount of additives in a provided composition can be from about 0.01 wt % to about 99 wt %, from about 0.01 wt % to about 70 wt %, from about 5 wt % to about 60 wt %, from about 10 wt % to about 50 wt %, from about 15 wt % to about 45 wt %, or from about 20 wt % to about 40 wt %, of the total silk composition. In some embodiments, ratio of silk fibroin to additive in the composition can range from about 1000:1 (w/w) to about 1:1000 (w/w), from about 500:1 (w/w) to about 1:500 (w/w), from about 250:1 (w/w) to about 1:250 (w/w), from about 200:1 (w/w) to about 1:200 (w/w), from about 25:1 (w/w) to about 1:25 (w/w), from about 20:1 (w/w) to about 1:20 (w/w), from about 10:1 (w/w) to about 1:10 (w/w), or from about 5:1 (w/w) to about 1:5 (w/w).

According to various embodiments, additive(s) may be distributed within provided compositions/articles homogeneously (e.g., substantially homogenously) or non-homogenously.

EXAMPLES

Figure 1:
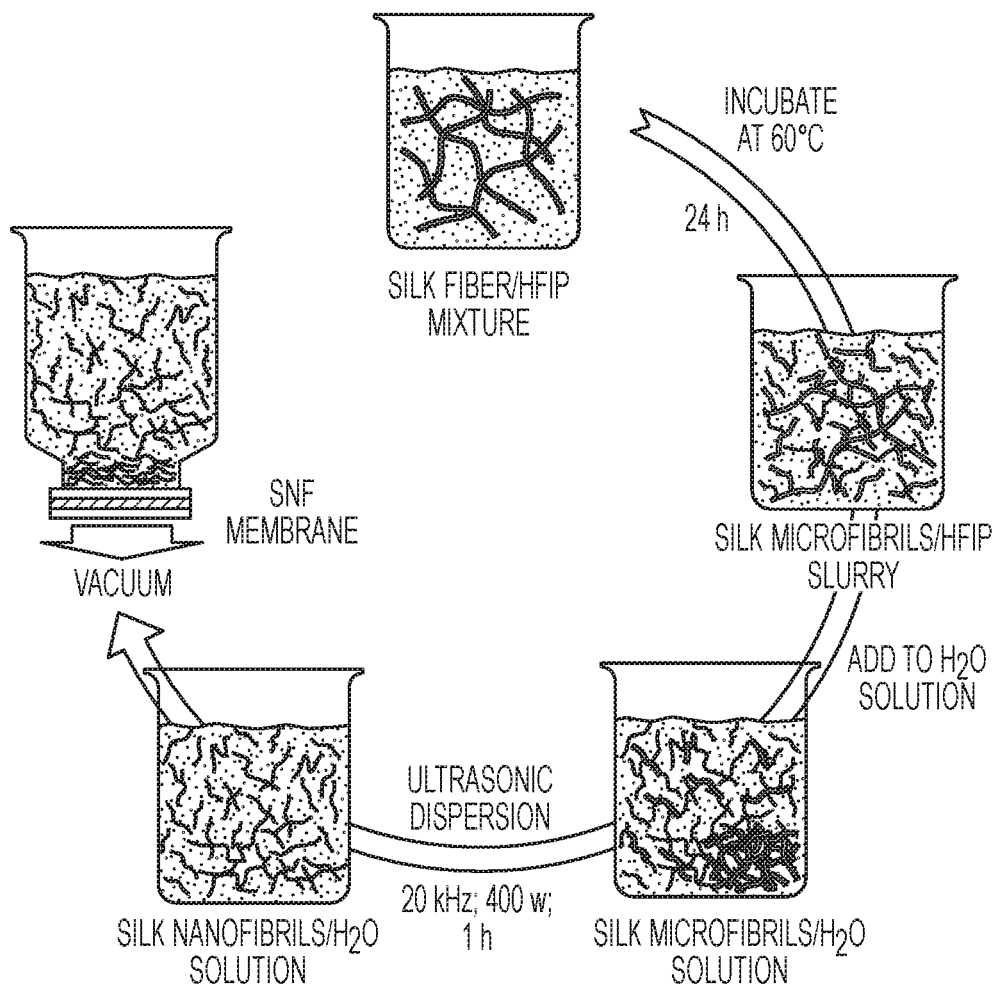
FIG. 1 shows a schematic of an exemplary process used to design ultrathin SNF membranes. In step 1, silk fiber in immersed in HFIP with a weight ratio of 1:30 and incubated at 60° C. for 24 h to obtain silk fiber/SMF slurries. In step 2, the dried silk fiber slurries transferred to $H_2O$ solution and precipitates removed. In step 3, SMF dispersion treated by ultrasound to extract SNFs. In step 4, SNF dispersion assembled to ultrathin SNF membranes via vacuum filtration.

Example 1—Preparation and Characterization of Filtration Membrane Made from Provided Silk Nanofibrils Materials and Methods The Example offers, among other things, data regarding the use of certain embodiments for the production of silk nanofibril (SNF)-based filtration membranes. Provided methods in this Example were able to facilitate and support the preparation and characterization of SNFs membranes. A flow diagram of the overall methods used in this Example is found in FIG. 1. Unless otherwise stated, the methods and processes used in this Example were as follows:

Sodium bicarbonate, $NaHCO_3$ (ACS reagent, ≥99.7%, Sigma-Aldrich, USA); 1,1,1,3,3,3-Hexafluoro-2-propanol, HFIP (≥99%, Sigma-Aldrich, USA); Copper (II) chloride, CuCl2 (Sigma-Aldrich, USA); L-tryptophan (Sigma-Aldrich, USA); Cytochrome c (Cytochrome c from equine heart, Sigma-Aldrich, USA); Bull serum albumin (lyophilized powder, ≥95%, Sigma-Aldrich, USA); Gold nanoparticles (5 nm diameter, OD 1, stabilized suspension in citrate buffer, Sigma-Aldrich, USA); CdSeS/ZnS quantum dots (COOH functionalized, 6 nm diameter, 1 mg mL−1 in $H_2O$, Sigma-Aldrich, USA); Alcian Blue 8GX (powder, Sigma-Aldrich, USA); Brilliant Blue G (pure powder, Sigma-Aldrich, USA), 8-Aminonaphthalene-1,3,6-trisulfonic acid disodium salt, ANTS (Bioreagent, ≥95%, Sigma-Aldrich, USA); Orange G (dye content ≥60%, Sigma-Aldrich, USA); Eosin B (cerfied by the biogical stain commission, dye content 90%, Sigma-Aldrich, USA); Brilliant Yellow (dye content 70%, Sigma-Aldrich, USA); Direct Red 81 (dye content 50%, Sigma-Aldrich, USA); Fluorescent Brightener 28 (Sigma-Aldrich, USA); Rhodamine B (powder, ≥95%, Sigma-Aldrich, USA); Congo Red (dye content ≥85%, Sigma-Aldrich, USA).

Exfoliation of Silk Nanofibrils

Figure 2:
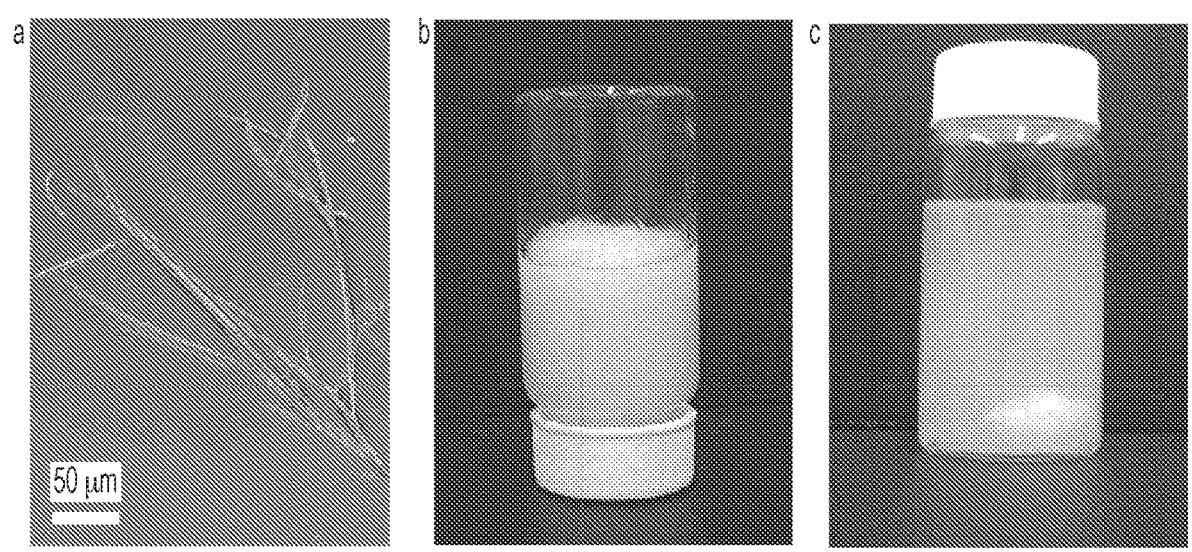
FIG. 2 shows visual appearance and characterizations of exemplary provided SMF and SMF solutions. (a) SEM image of SMFs. (b) photograph of SMF pulp blend. (c) photograph of SMFs/water mixture.

Silk Nanofibrils (SNFs) solution was obtained by dissolving degummed silk fibers in HFIP solution. *Bombyx mori* (*B. mori*) silkworm cocoons were degummed by boiling in two 30 min changes of 0.5% (w/w) $NaHCO_3$. Then the degummed silk fibers were washed with distilled water and allowed to air-dry at room temperature. The degummed silk fibers were then immersed in HFIP solution with a weight ratio of 1:30, and sufficiently agitated to make sure that all fibers were immersed. Then, the silk fiber/HFIP mixture were sealed in airtight containers and were incubated at 60° C. for 24 hrs to partially dissolve the silk fibers to silk microfibrils (SMFs). (FIG. 2) After incubation, the resultant SMFs pulp was dried in a fume hood to evaporate the HFIP for 4 hours. Following the drying, the SMFs were added to water with weight ratio of 1:200 under continuous stirring or agitation, followed by removal of any undissolved material. Finally, the silk/water mixture (see FIG. 2, panel c) was sonicated at 120 μm amplitude and 20 kHz frequency with interval of 10 s. After 1 hr, the exfoliated SNFs dispersion was harvested by centrifugation at 10,000 rpm for 20 min.

Silk Nanofibrils Membrane Fabrication

Figure 3:
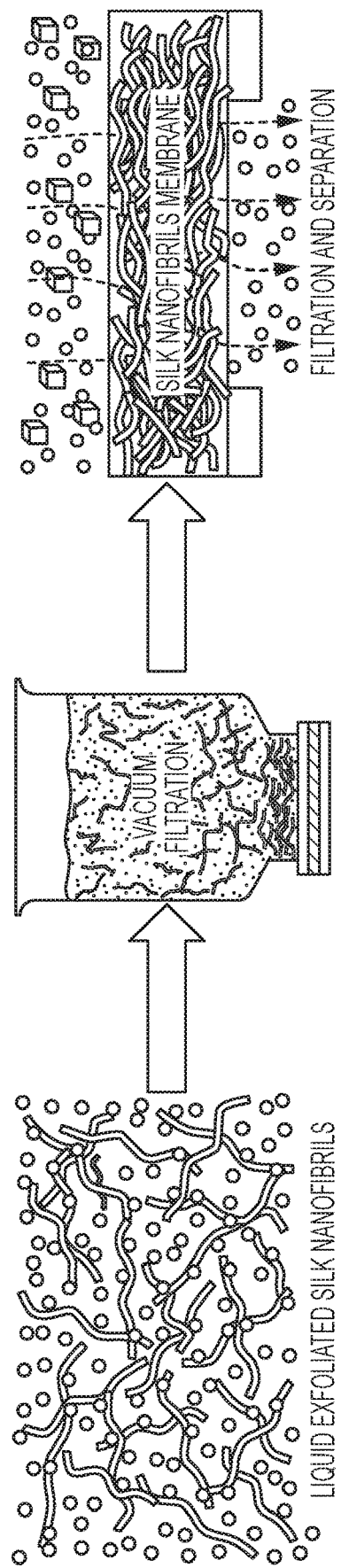
FIG. 3 shows a schematic of an exemplary provided process to prepare SNF membranes using SNF solutions.

The SNF membranes were fabricated by vacuum-filtrating the SNF dispersions through a Sigma-Aldrich vacuum filtration assembly and polycarbonate filtration membranes (pore size, 200 nm; diameter 47 mm; Sigma-Aldrich, see FIG. 3). The thickness of membrane was tunable by adjusting the concentration and volume of the SNFs dispersed during vacuum filtration.

Silk Nanofibrils and Silk Nanofibrils Membrane Characterization

The morphology and structure of SNFs and SNF membranes were characterized by scanning electron microscope (SEM) and Fourier transform infrared spectroscopy (FTIR). All SEM observations were carried out using a Zeiss Ultra Plus field emission scanning electron microscope (in Harvard University Center for Nanoscale Systems) at an acceleration voltage of 5 kV. To prevent electrical charging, all the specimens were deposited with a 2-nm-thick Pd/Pt layer before observation. FTIR measurements were carried out by a Jasco FTIR-6200 (Jasco Instruments, Easton, Md.) spectrometer with ATR model. For each measurement, 64 interferograms were co-added and Fourier-transformed employed a Genzel-Happ apodization function to yield spectra with a nominal resolution of 4 $cm^{-1}$.

Separation Performance Measurements

The separation performances were performed on a vacuum filtration device (Sigma-Aldrich glass vacuum filtration assembly device, membrane diameter of 47 mm, inner diameter of funnel top 35 mm). Water (100 mL) was filtered across the membrane to measure the pure water flux (J, L $m^{-2}$ $h^{-1}$ $bar^{-1}$) that is calculated by J=V/(Atp), where V is the volume of the water filtered (L), A is the effective membrane filtration area ($m^2$), t is the filtration time (h), and p is the suction pressure across the membrane (bar). The filtration area of our filter holder is 9.62 $cm^2$ and the porosity of the PC membrane is 10%. Then, the effective surface area in our case is 0.962 $cm^2$. Dyes, proteins, and gold nanoparticles were used to evaluate the membrane rejection with the feed (20 mL) filtered across the membrane under 1 bar of applied pressure. Permeation was characterized by UV-vis spectrophotometer (SpectraMax M2, Molecular Devices, CA). The rejection (R, %) is calculated by $$R = \left(1 - \frac{Cp}{Cf}\right) \times 100\%$$

where $C_f$ and $C_p$ are the concentrations of compound in the feed and permeate, respectively.

Results

Figure 4:
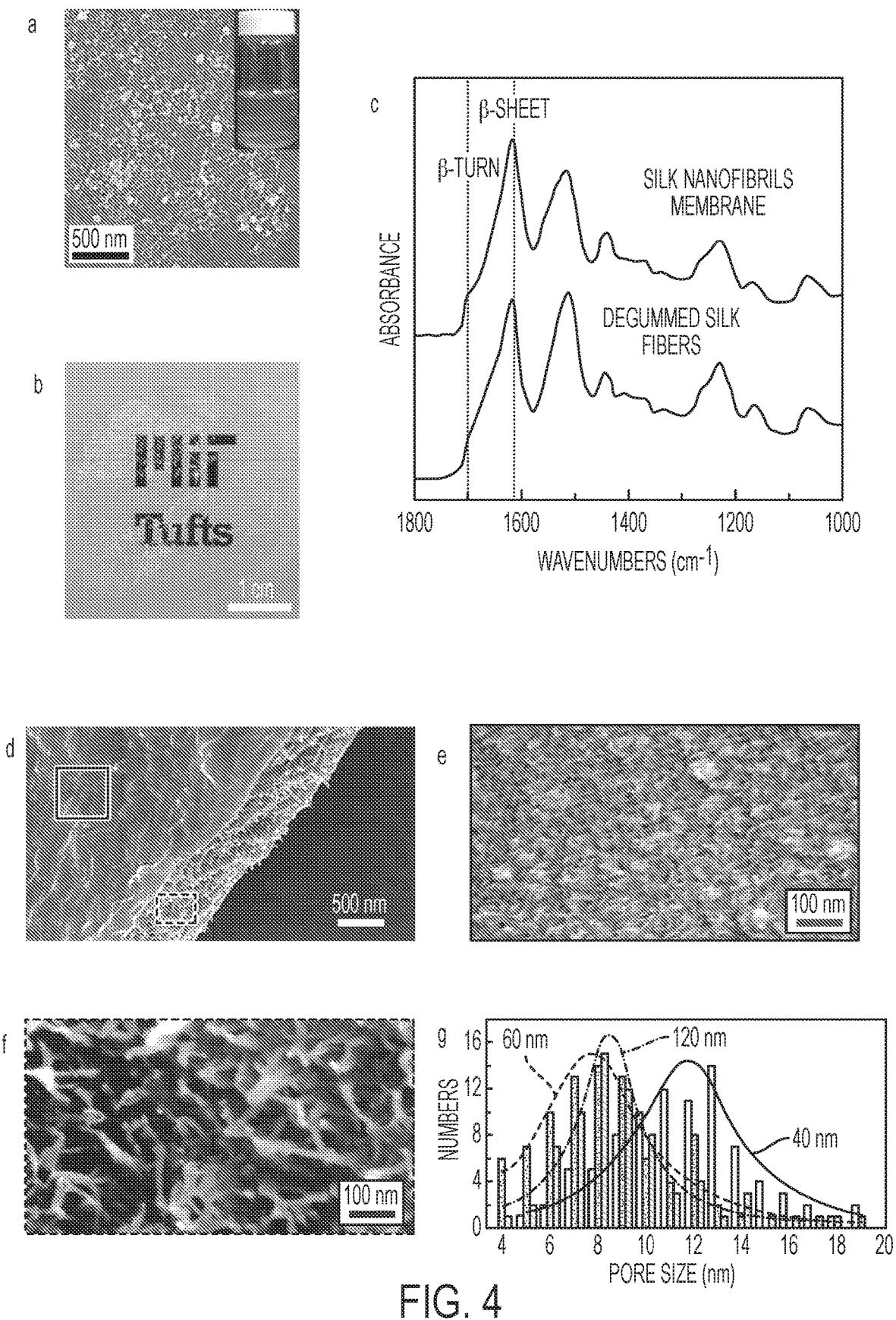
FIG. 4 shows visual appearance and structural characterization of exemplary SNF dispersions and membranes. (a) SEM image of exfoliated SNFs. The insert is a photograph of SNF dispersion at room temperature for 1 month. (b) picture of a free-standing SNF membrane with a thickness about 520 nm under visual light with structural color. (c) FTIR spectra of SNF membrane and degummed silk fibers. (d-f) SEM images of SNF membranes with a thickness of 520 nm. (e-f) Images of top view and cross-sectional SEM images of membranes, respectively. (g) Pore size distribution of the SNF membranes with thicknesses of 40, 60, and 120 nm.
Figure 5:
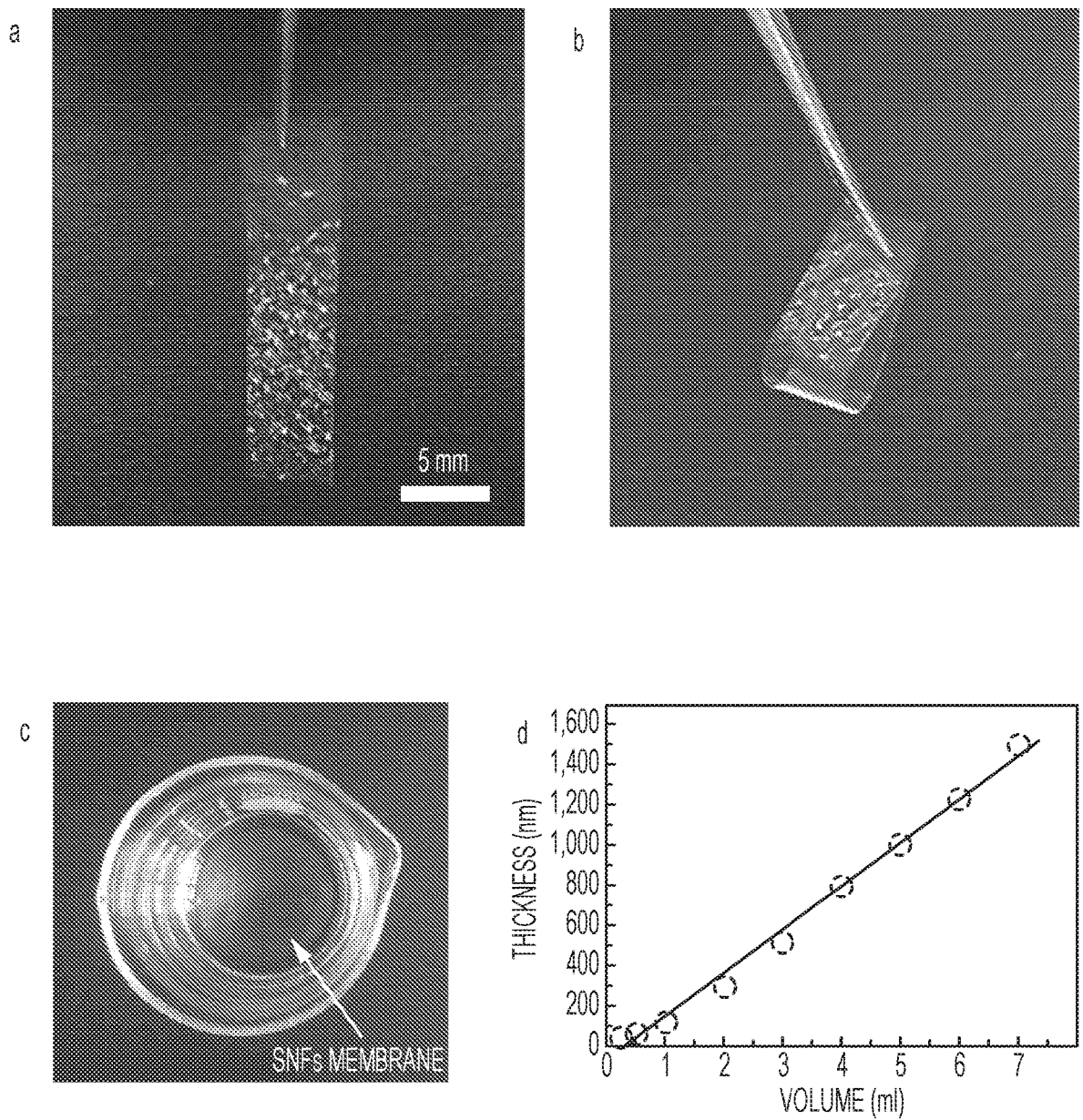
FIG. 5 shows photographs of exemplary SNF membranes and the relationship between the volume of SNF solution and the membrane thickness. (a-b) Photographs of SNF membranes with a thickness of 520 nm after cutting (a) and during bending (b). (c) photograph of SNF membrane with thickness of 520 nm immersed in water for 1 day at room temperature. (d) Linear relationship between the volume of SNF solution (0.1 wt %) and membrane thickness.

In this Example, SNF solution was prepared as described above by partially dissolving degummed silk fibers in HFIP solution. The dispersion was transparent (FIG. 4, panel a) and was stable over several months. SEM images revealed that the extracted SNFs had a diameter of 20±5 nm and a contour length in the range of 300-500 nm (FIG. 4, panel a), similar to the diameter of single SNFs found in silk fibers. After vacuum filtration process, the resultant membranes with thickness of about 520 nm could be removed from the supporting substrate and appeared homogeneous and transparent with structural color on the surface (FIG. 4, panel b). These free-standing membranes were also robust and flexible and could be cut and bent without damage (FIG. 5, panels a-b). Compared with other ultrathin membranes that lack flexibility, such as inorganic nanofibers, nanowires, and nanosheet based membranes, the mechanical superiority of these SNF membranes permit use in pressure-driven filtration operations, even at high applied pressures. Different from cast silk fibroin membranes which will dissolve in water if not treated with alcohol or by water annealing to generate β-sheet secondary structures, these SNF membranes were stable in water without dissolution (FIG. 5, panel c). This property, as a critical role in filtration ensures the stability of membrane without collapse in the filtration process. FTIR was utilized to assess structural details of the SNF membrane (FIG. 4, panel c). The amide I band showed a similar shape to degummed silk fibers: a sharp peak at 1620 $cm^{-1}$ and a shoulder at 1695 $cm^{-1}$, which are assigned to β-sheets and β-turns of the hairpin-folded antiparallel β-sheet structure, respectively, indicating that the SNFs were mainly composed of β-sheet. Such structure not only gives the membranes mechanical robustness but also contributes the excellent stability in water, as with native silk fibers.

SEM images further reveals the mesoscopic structure of the membranes. A free-standing membrane with a thickness of 520 nm revealed a uniform fibrous structure (FIG. 4, panel d). The related surface (FIG. 4, panel e) and cross-section SEM images (FIG. 4, panel f) showed a uniform pore size distribution with diameters of 6±2 nm with interconnected pores that were uniform without cracks or pinholes. The thickness of membrane was controllable by adjusting the concentration and volume of the SNFs dispersed during vacuum filtration. In a typical procedure, 5 mL of dispersion with a concentration of 0.1 wt % generated a membrane of about 1000 nm thick using a casting mold of 3.5 cm in diameter, and the volume of the SNF dispersion was linearly correlated to the membrane thickness (FIG. 5, panel d).

Figure 6:
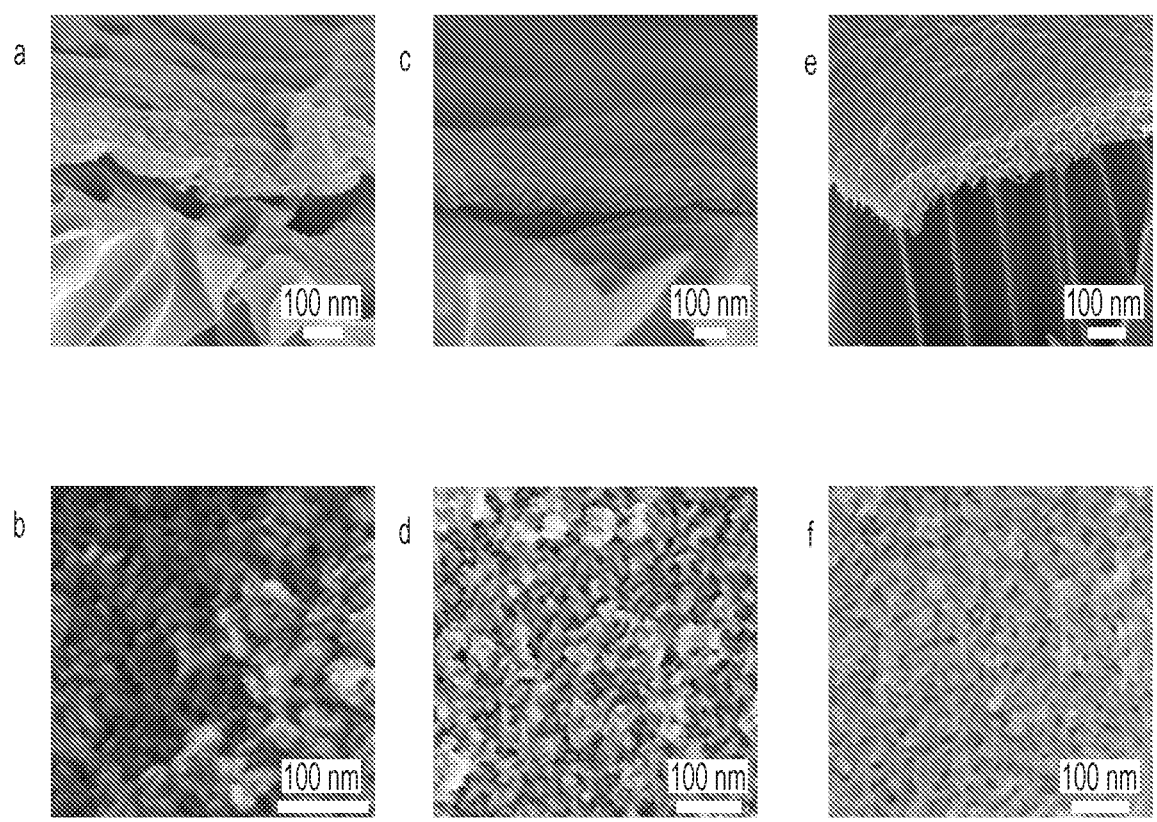
FIG. 6 shows SEM images of exemplary ultrathin SNF membranes. (a, b) SNF membranes prepared by 0.25 ml SNF dispersion with a concentration of 0.1 wt %. (c, d) SNF membranes prepared by 0.5 ml SNF dispersion with a concentration of 0.1 wt %. (e, f) SNF membranes prepared by 1 ml SNFs dispersion with a concentration of 0.1 wt %. (a, c, e) cross-section images of the membranes. (b, d, f) surface image of the membranes.
Figure 7:
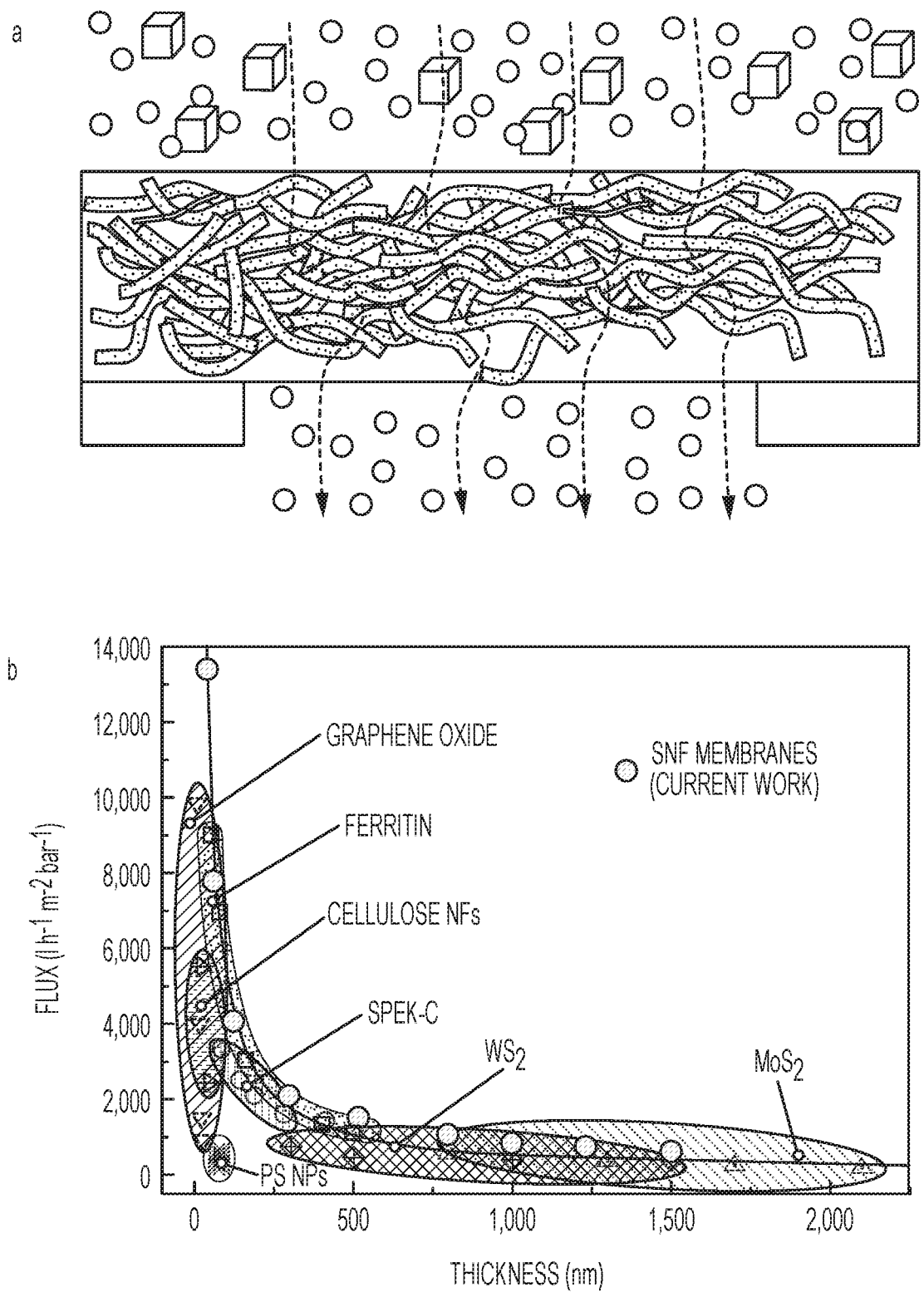
FIG. 7 shows a schematic of an exemplary filtration process and exemplary data regarding the filtration through SNF membranes. (a) Schematic showing how SNF membranes reject large molecules while allowing small molecules to pass through. (b) Thickness-dependent changes in permeability to pure water. The red circles are fluxes determined by using polycarbonate membranes with an effective surface area of $0.962$ $cm^2$ (porosity, 10%). The red solid line is a fitted curve using the Hagen-Poiseuille equation. The comparison of pure water flux of SNF membranes with other materials used in ultrathin filtration membranes is presented.

Additionally, pore size could be tuned to some extent by choosing the appropriate filtration volume and concentration of SNF dispersion. For instance, the average pore size varied from 12 to 8 nm (FIG. 4, panel g) with the SNF membrane thickness increased from 40 nm (0.25 mL 0.1 wt % SNF solution, FIG. 6, panels a, b) to 60 nm (0.5 mL 0.1 wt % SNF solution, FIG. 6, panels c, d). The pore size distribution could also be narrowed through control of membrane thickness. For example, the 120 nm thick membrane had the narrowest pore size distribution when compared to the 40 and 60 nm thick membranes (FIG. 4, panel g and FIG. 6). These results suggest utility for these types of membranes related to the separation of colloidal particles and molecules of varying sizes (FIG. 7, panel a).

To evaluate the permeation performance of these SNF membranes, pure water fluxes were assessed through membranes with different thicknesses from 40 to 1500 nm. Surprisingly, the flux of 40 nm thick SNF membrane was up to 13000 L h$^{-1}$ m$^{-2}$ bar$^{-1}$, more than 1000 times higher than fluxes of commercial filtration membranes and better than fluxes of most advanced recently reported ultrathin membranes (FIG. 7, panel b). By increasing the thickness of the membrane, the water flux sharply declined, consistent with the Hagen-Poiseuille theoretical models (red plot in FIG. 7, panel b) and other experimental reports (FIG. 7, panel b). However, the water flux was larger than 600 L h$^{-1}$ m$^{-2}$ bar$^{-1}$, even with the thickness increased to 1500 nm, this flux was also faster than that of most commercial materials.

Figure 8:
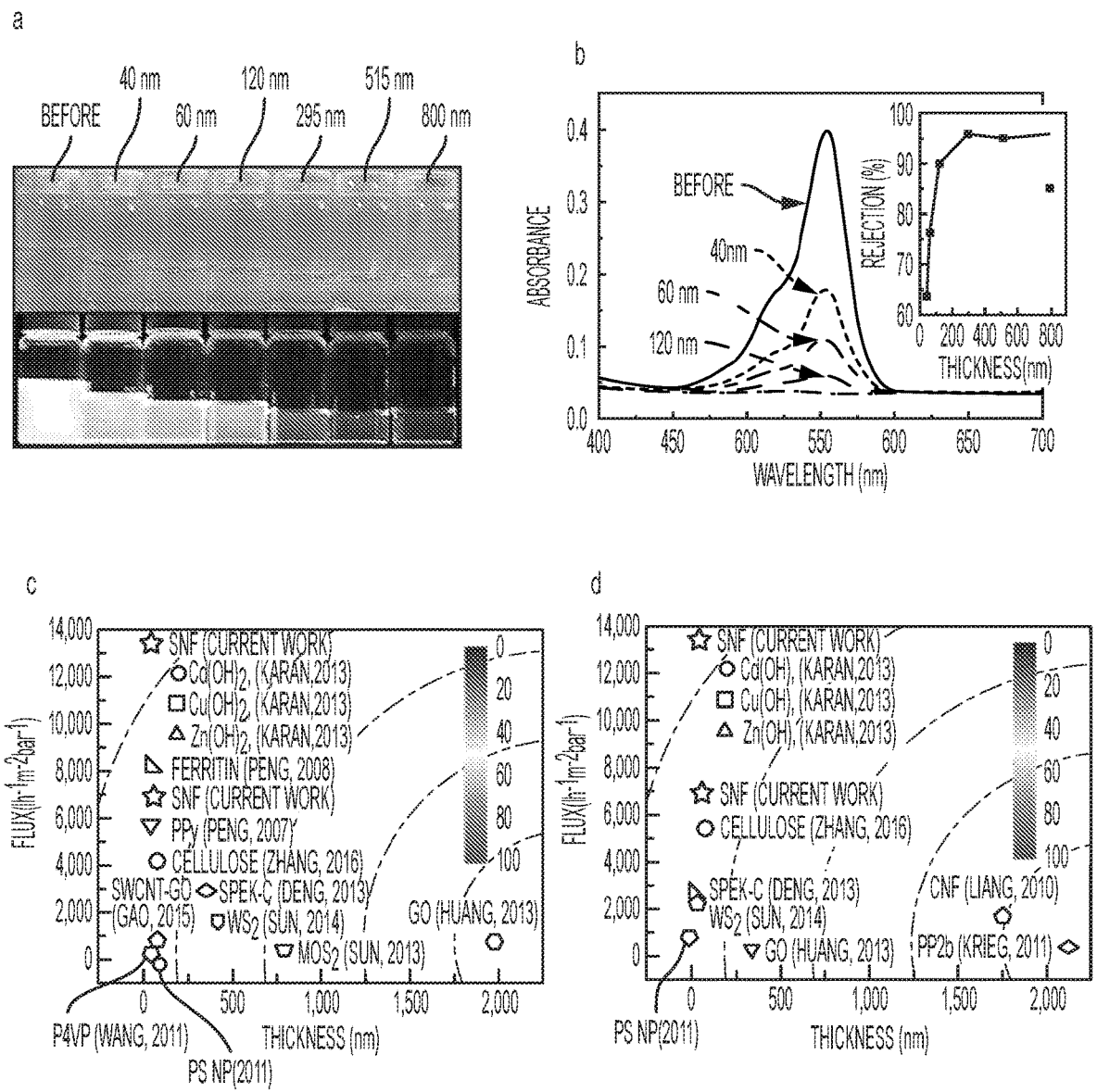
FIG. 8 shows exemplary data regarding separation performance of SNF membranes. (a) The pictures before and after filtering Rhodamine B aqueous solutions using SNF membranes with different thicknesses. The top and bottom images are under visual and UV light, respectively. (b) UV-vis absorption changes of an aqueous solution of Rhodamine B after filtration with SNF membranes with different thicknesses. The insert plot shows the rejection of Rhodamine B aqueous solution with different thicknesses of the SNF membranes. (c, d) Comparison of separation performance of SNF membranes for cytochrome c (c) and 5 nm gold nanoparticle dispersion (d) with other ultrathin filtration membrane materials. The rejection is represented by the color of the pattern. The blue and red are 0% and 100% rejection, respectively. The hollow five-pointed star pattern is the separation performance of the SNF membranes. In these two figures, the separation performance of the SNF membranes with 40 and 60 nm thicknesses is listed for comparison.

The separation performance of the SNF membranes was measured through pressure-driven filtration. First, Rhodamine B was used to study the influence of membrane thickness on separation performance (FIG. 8, panel a). By increasing the membrane thickness, both visual and fluorescence color of the permeated solution became lighter and transparent, and no fluorescence was observed when the thickness reached 295 nm. The UV-vis spectra (FIG. 8, panel b) confirmed the visual results with an absorption at 554 nm that dropped gradually with no peak appearing for the 295 nm thick membrane. The calculation demonstrated that rejection reached equilibrium with a value of 96% with a thickness of 295 nm (insert plot in FIG. 8, panel b). Next, protein molecules (cytochrome c, Cyt. c; bull serum albumin, BSA), colloids (gold nanoparticles, 5 nm diameter; CdSeS/ZnS quantum dots, 6 nm diam.), small molecules (L-tryptophan, 1.1×0.5 nm) and ions (Cu$^{2+}$), were selected to assess size-selectivity. Small Cu$^{2+}$ ions (rejection: 3±3%) and L-tryptophan (rejection: 10±2%) freely passed through the channels (Table 1). Cyt. c, BSA, gold nanoparticles and CdSeS/ZnS quantum dots, as larger size objects, had a rejection of 99±1, 100±0, 99±2, and 100±1%, respectively. These results validated that pore size was a crucial factor for separations with the SNF membranes.

Figure 9:
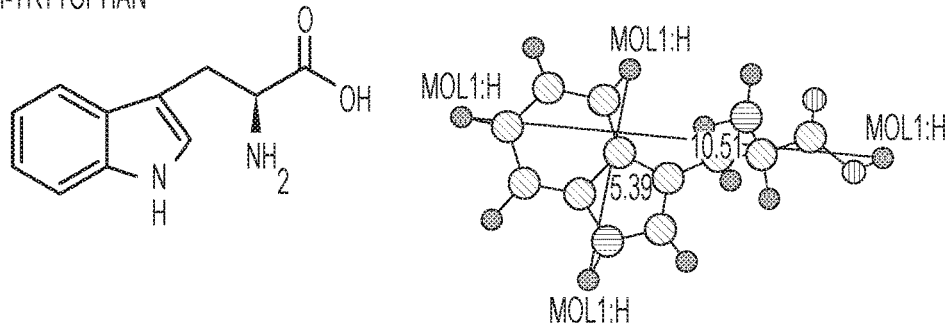
FIG. 9 shows chemical formulas and molecular size of exemplary dyes. The molecular sizes were calculated using Materials studio 7.0. The unit of molecular size showing in the images is angstroms (Å).
Figure 9:
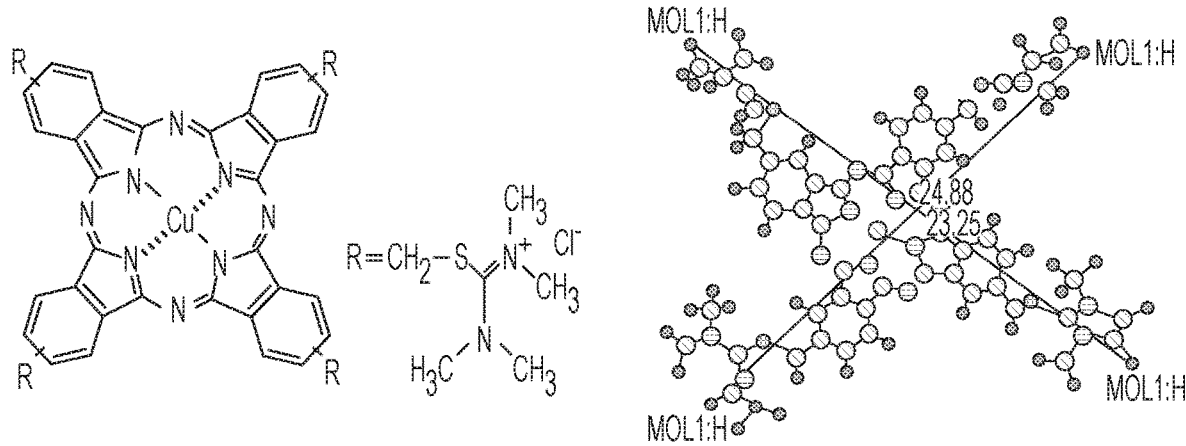
Figure 9:
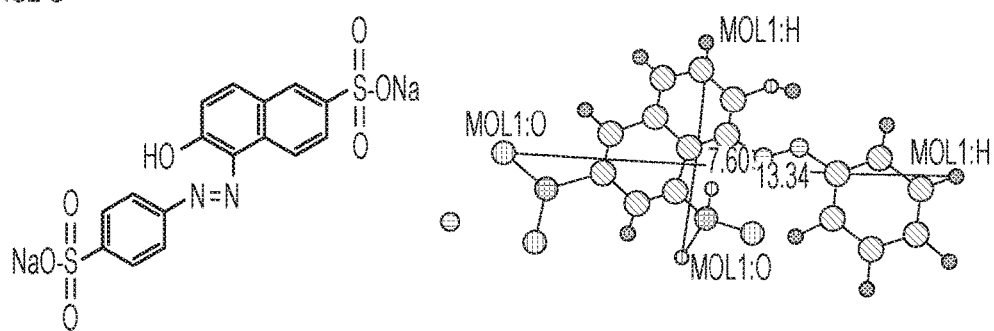
Figure 9:
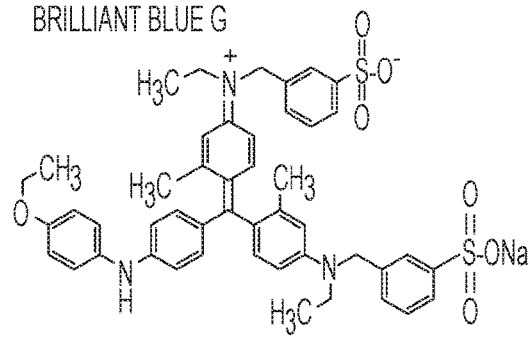
Figure 9:
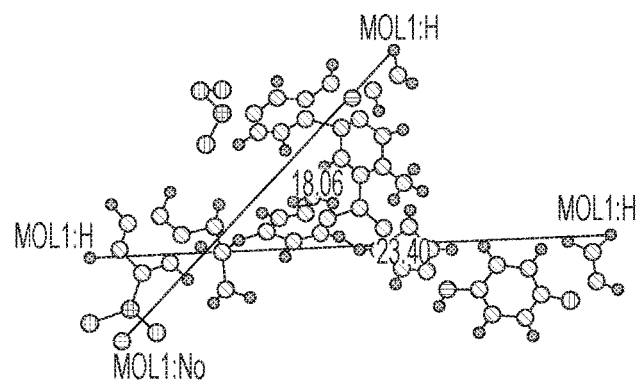
Figure 9:
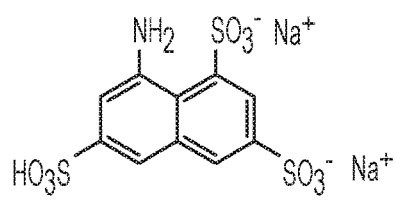
Figure 9:
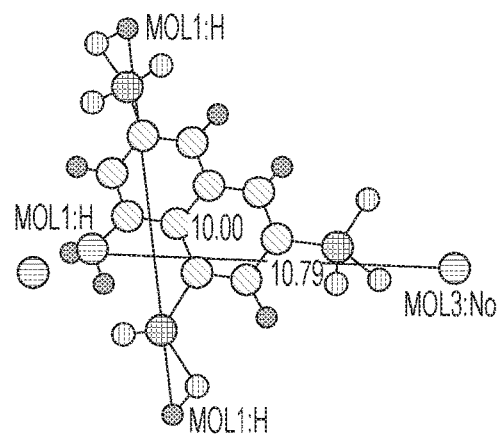
Figure 9:
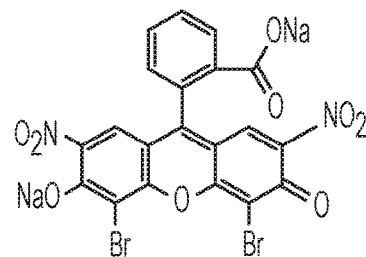
Figure 9:
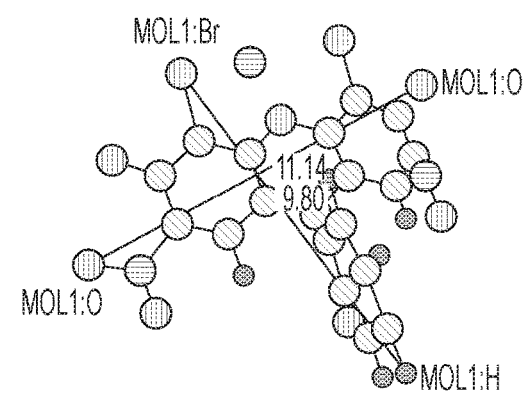
Figure 9:
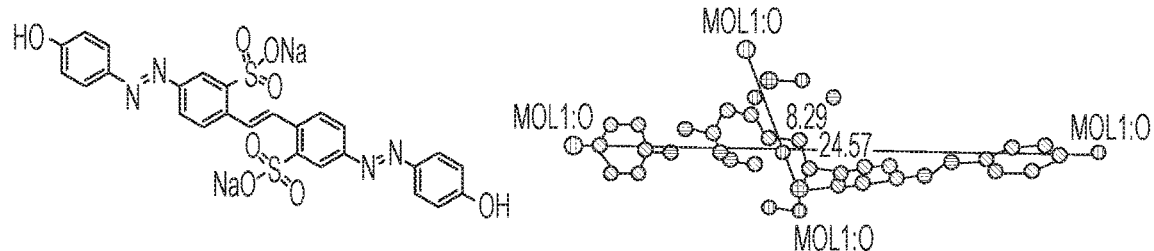
Figure 9:
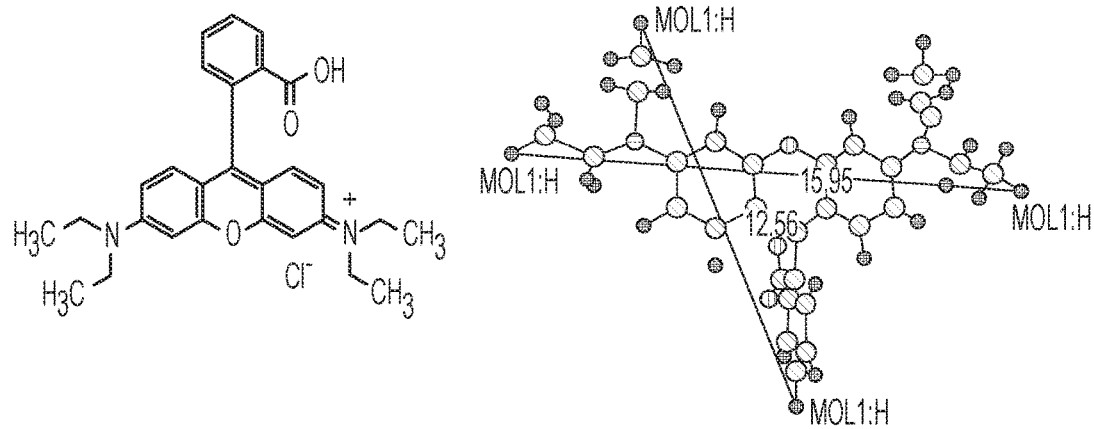
Figure 9:
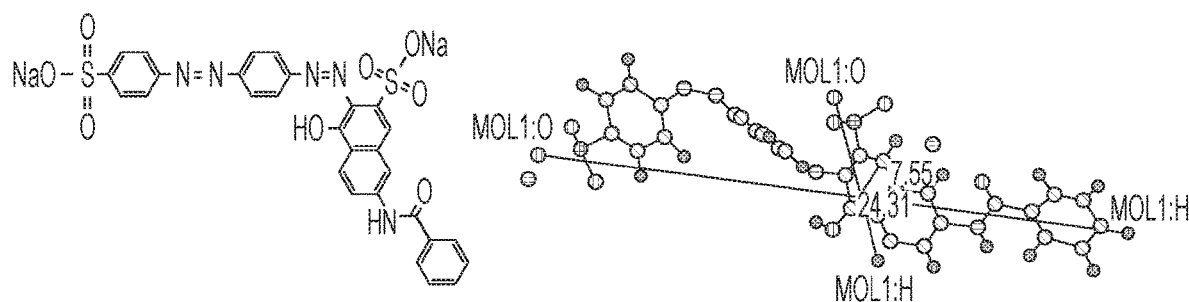
Figure 9:
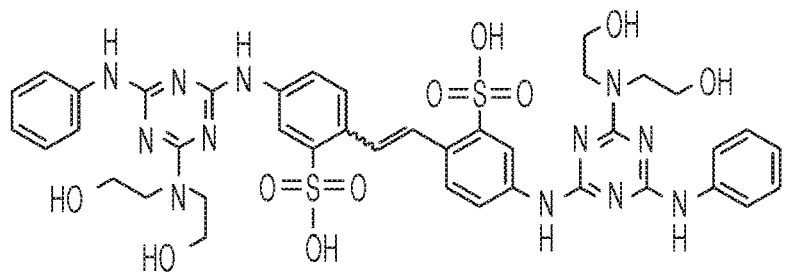
Figure 9:
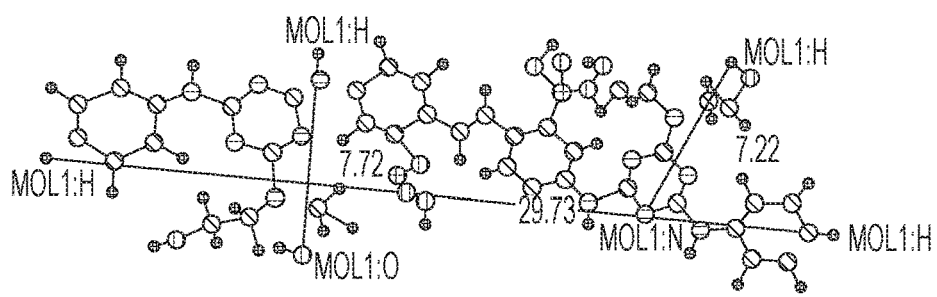
Figure 9:
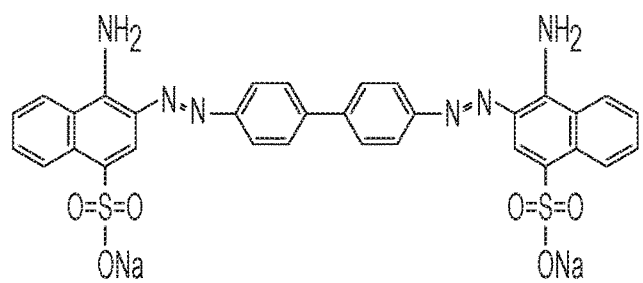
Figure 9:
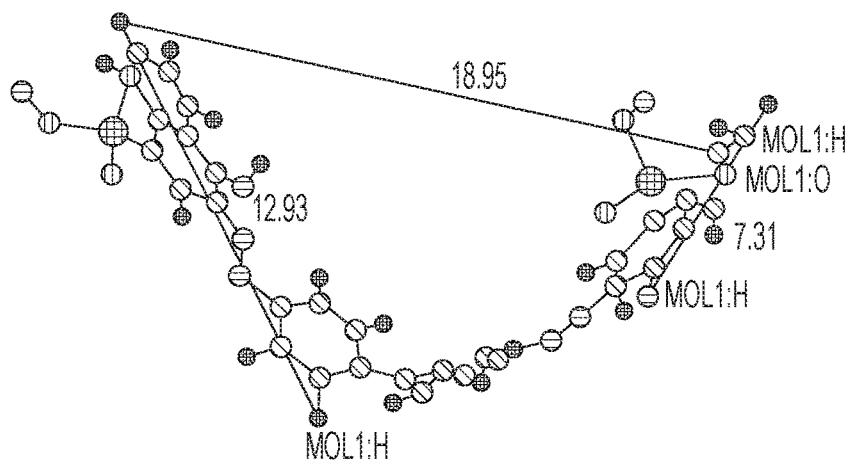

The separation were further monitored with different dyes, which are usually unsatisfactory in terms of separation with most ultrathin filtration membranes. Their separation performance is summarized in Table 1. Size, shape, and charge of the molecules were key factors for rejection. For example, large size molecules, such as Alcian Blue 8GX (2.5×2.3 nm) and Brilliant Blue G (2.3×1.8 nm) had a 100±0% rejection, versus small molecules, such as 77±2% rejection for sulfonated naphthalene (ANTS) (1.1×1.0 nm), 82±2% for Orange G (1.3×0.8 nm), and 84±1% for Eosin B (1.1×1.0 nm). Linear molecules even with large molecule length (e.g., Brilliant Yellow with size of 2.4×0.8 nm; Direct Red 81 with size of 2.4×0.8 nm; Fluorescent Brightener 28 with size of 3.0×0.8 nm) could partially permeate the membrane with rejection rates of 64±3, 80±1, and 85±2%, respectively. In addition, because SNFs are negatively charged at neutral pH (the isoelectric point of silk fibroin is 4.53), more positively charged molecules can be taken up by the membranes via electrostatic interactions. The positively charged molecules (e.g., Rhodamine B and Alcian Blue 8GX) showed higher rejection than negatively charged molecules with similar sizes (e.g., Congo Red with rejection of 86±2%). Besides the factors discussed above, hydrophobic interactions of SNFs and dye molecules also contributed to the high separation performance of the SNF membranes because most of the dye molecules have benzene rings (FIG. 9), which act with the hydrophobic domain to interact with the silk fibroin chains, (i.e., GAGAGS peptides that form β-sheets). Hydrophobic interactions also relate to the mechanism by which carbon nanotubes and graphene oxide based filtration membranes can separate Rhodamine B from solution, whereas polymer-based filtration membranes with similar pore sizes cannot reject the dyes.

TABLE 1

Separation Performance of 120 nm Thick SNF Membranes for Dyes, Protein, and Nanoparticles

|  | Mw (g mol$^{-1}$) | size (nm) | concentration | analyte charge | rejection (%) |
| --- | --- | --- | --- | --- | --- |
| Cu$^{2+}$ | 134.45 |  | 1 mM | + | 3 ± 3 |
| L-tryptophan | 204.23 | 1.1 × 0.5 | 979 μM | − | 10 ± 2 |
| cytochrome c | 12400 | 2.5 × 2.5 × 3.7 | 2.0 mg mL$^{-1}$ | − | 99 ± 1 |
| Bull serum albumin | ~66 kDa | 14 × 4 × 4 | 2.0 mg mL$^{-1}$ | − | 100 ± 0 |
| Gold nanoparticles |  | 5 nm | 5.5 × 10$^{13}$ unit per mL | − | 99 ± 2 |
| CdSeS/ZnS quantum dots |  | 6 nm | 1 mg mL$^{-1}$ | − | 100 ± 1 |
| Alcian Blue 8GX | 1298.88 | 2.5 × 2.3 | 185 μM | + | 100 ± 0 |
| Brilliant Blue G | 854.02 | 2.3 × 1.8 | 398 μM | − | 100 ± 0 |
| ANTS | 427.33 | 1.1 × 1.0 | 548 μM | − | 77 ± 2 |
| Orange G | 452.4 | 1.3 × 0.8 | 601 μM | − | 82 ± 2 |

TABLE 1-continued

Separation Performance of 120 nm Thick SNF Membranes for Dyes, Protein, and Nanoparticles

| | Mw (g mol $^{-1}$) | size (nm) | concentration | analyte charge | rejection (%) |
|---|---|---|---|---|---|
| Eosin B | 624.06 | 1.1 × 1.0 | 320 μM | − | 84 ± 1 |
| Brilliant Yellow | 624.5 | 2.4 × 0 8 | 76 μM | − | 64 ± 3 |
| Direct Red 81 | 675.60 | 2.4 × 0.8 | 414 μM | − | 80 ± 1 |
| Fluorescent Brightener 28 | 916.98 | 3.0 × 0.8 | 124 μM | − | 85 ± 3 |
| Rhodamine B | 479.01 | 1.6 × 1.3 | 5 μM | + | 91 ± 1 |
| Congo Red | 696.66 | 1.9 × 1.3 | 17 μM | − | 86 ± 2 |

ANTS = 8-aminonaphthalene-1,3,6-trisulfonate

FIG. 8, panels c-d summarizes the separation performance of the SNF membranes for Cyt. c (FIG. 8, panel c) and 5 nm gold nanoparticles (FIG. 8, panel d) compared with other ultrathin filtration materials from the literatures. The SNF membranes exhibit a better balance of thickness, flux, and separation performance. The thicknesses of membranes were in the range of 40-60 nm, comparable with most ultrathin membranes. The flux was 1.2-6.2 times higher than that of most inorganic and polymer membranes and comparable with ferritin and inorganic nanowires. In terms of separation performance, the rejection of protein and gold nanoparticles was higher than that of membranes with similar thickness.

Example 2—Method for Preparations and Characterizations of Regenerated Silk Fibers Materials and Methods The Example offers, among other things, data regarding the use of certain embodiments for the production of regenerated silk fibers (RSFs). Provided methods in this Example were able to facilitate and support the preparation and characterization of RSFs. Unless otherwise stated, the methods and processes used in this Example were as follows:

Preparation of Silk Microfibril Solution

Silk Microfibril (SMF) solution was obtained by dissolving degummed silk fibers in HFIP solution. B. mori silkworm cocoon silk fibers were degummed by boiling in two 30 min changes of 0.5% (w/w) NaHCO$_3$ (Sigma-Aldrich, US) solution. The degummed silk fibers were washed with distilled water and allowed to air dry at room temperature. The degummed B. mori silk fibers were then immersed in HFIP solution with a weight ratio of 1:20, and sufficient oscillation was applied so that all fibers were immersed. Then, the silk fiber/HFIP mixture were sealed in airtight containers and were incubated at 60° C. for 7-15 days. Herein, the extended incubation time increased the concentration and viscosity of the SMF solution. After incubation, the resultant silk fiber/HFIP mixture presented as a uniform viscous solution with nematic liquid-crystal-like texture. The resultant silk fibers were partially dissolved in HFIP to microfibrils with diameter of 5-10 μm and longer contour lengths of several hundreds to thousands of micrometers. The degummed silk fibers was characterized by FTIR (Jasco FTIR-6200, Jasco Instruments, Easton, Md.). The texture of the SMF solution was assessed by polarizing optical microscope (Olympus BX51-P, Japan).

Preparation of Regenerated Silk Fibers

Figure 10:
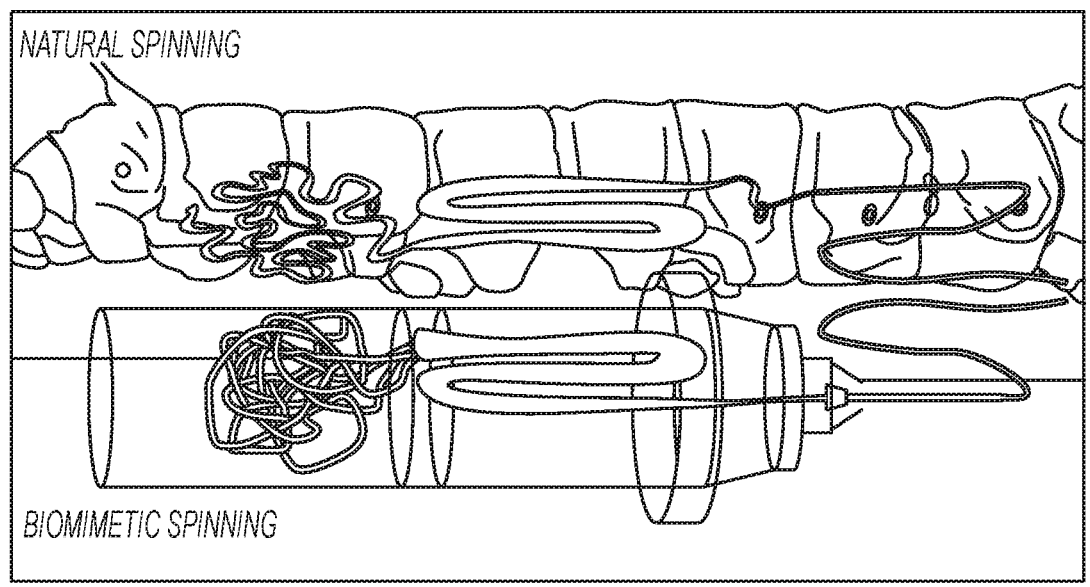
FIG. 10 shows an exemplary schematic of natural and biomimetic spinning process.

Regenerated silk fibers (RSFs) were fabricated by biomimetic spinning process using SMF solution. The SMF solution was transferred to a syringe with a needle inner diameter of 0.6 mm, then the dope directly spun from the syringe needle at room temperature. (see FIG. 10-FIG. 12, panels a-b) During the spinning process two approaches can be used to apply the shear force to the spinning dope. First is pushing the plunger with a slight force by hand or an injection pump. Second is using a winding device to reel the dope from the syringe needle; akin to the natural spinning process. All steps should be conducted in a chemical fume hood with the necessary precautions.

Characterization of Regenerated Silk Fibers

The structure, morphology, and the mechanical properties of RSFs were further characterized. The structure of RSFs were assessed by polarizing optical microscope (Olympus BX51-P, Japan) and FTIR (Jasco FTIR-6200, Jasco Instruments, Easton, Md.). FTIR characterization reveals that the RSFs are mainly composed of β-sheet (crystalline) structures. For each FTIR measurement, 64 interferograms were co-added and Fourier-transformed employed a Genzel-Happ apodization function to yield spectra with a nominal resolution of 4 cm$^{-1}$. Deconvolution of amide I bands was carried out using PeakFit 4.12. The numbers and positions of peaks were defined from the results of second derivative spectra and fixed during the deconvolution process. A Gaussian model was selected for the band shape and the bandwidth which was automatically adjusted by the software. It should be noted that each spectrum shown was from a single experiment, but the data obtained from the spectra (e.g., β-sheet content) were the average of five separate deconvolutions from different samples.

The morphology of RSFs was characterized by SEM (Ultra 55 field emission scanning electron microscope, Carl Zeiss AG, Harvard University Center for Nanoscale Systems) at an acceleration voltage of 5 kV. To prevent electrical charging, all specimens were coated with a 5-nm-thick Pd/Pt layer before observation. The mechanical properties of fibers were tested by using an Instron 3366 machine (Instron, Norwood, US) in tensile mode at 25° C. and 50% relative humidity with a tensile speed of 0.5 mm min$^{-1}$.

Preparation of Cell Cultures

Human Dermal Fibroblasts (HDFs) were cultured on RSF to study the biocompatibility and the effect of the structural hierarchy on the growth of HDFs. HDFs were cultured in Dulbecco's Modified Eagle Medium (DMEM, Invitrogen) supplemented with 10% fetal bovine serum (FBS, Sigma-Aldrich), and 100 U/mL penicillin, 100 streptomycin (Invitrogen). Silk fibers were sterilized in 70% ethanol and thoroughly rinsed in sterile distilled water. The fibers were incubated in growth medium with the aforementioned compositions for 24 hours before cell seeding. Cells were seeded on fibers by incubating fibers in a cell suspension of $0.5 \times 10^6$ cells/mL. Then, the fibers were transferred to fresh medium after 4 hours. Cell medium was changed every two days. The viability of the HDFs on silk fibers was assessed by live/dead assay (Molecular Probes). The cells were incubated in medium containing 2 μM calcein-AM and 4 μM EthD-1 at 37° C. for 15 min. The stained RSF/cell constructs were then observed with a Keyence BZX710 fluorescence microscope (Keyence).

Simulations

RSFs were modeled by a coarse-grained elastic network model composed of nonlinear elastic springs and mass beads. FCC lattice structure was used with a lattice constant of 0.01 mm to define the coordinate of each mass bead. The interaction between the two nearest neighboring mass beads was modeled by a nonlinear elastic spring with the bond energy (E) given by a Morse potential as $$E = D[1 - e^{-\alpha(r-r_0)}]^2 \quad (1)$$

where D is the bond energy, α is the parameter control the stiffness of the bond, $r_0 = 0.0071$ mm is the equilibrium bond length as the nearest neighboring distance of two beads and r is the bond length that is changing in the simulation. By adjusting the numerical values of the parameters (D, α), different force-extension curves of the pristine silk fiber were generated. Referring to the former test on the nature silk fiber, the numerical values of $D = 5.7 \times 10^{-9}$ J and $\alpha = 9 \times 10^5$ m$^{-1}$ are generated that give the force-strain curve with the strength of 132 MPa corresponding to the extension of 17%. The number of defects (N) randomly distributed on the silk surface is given by $$N = Int[5R/(2 \times 10^{-5})] \quad (2)$$

where Int is the function to take the integral number and R is the radius of the silk fiber. For the smallest fiber of 0.02 mm in radius, there are 5 defects randomly distributed for the simulation model.

Fabrication and Measurement of RSF-Based Sensors

Carbon nanotube (CNT)-coated RSFs were fabricated by dip-coating the RSFs into the carbon-nanotube solutions. The carbon-nanotube solution was made by dispersing 100 mg multi-wall carbon nanotubes (MWCNT, Sigma-Aldrich, US) into a mixture of 1 g $CaCl_2$ (Sigma-Aldrich, US) and 20 g formic acid (Sigma-Aldrich, US), followed by ultrasonication for 1 hour at room temperature. Then 1 g degummed silk fiber was added in solution with intense shaking to obtain the conductive silk/MWCNT solution. After drying the solution at room temperature to eliminate the formic acid, the RSFs was coated with MWCNT/silk/$Ca^{2+}$ ink.

The conductivities of conductive RSF-based materials were assessed using a Fluke 87 V Digital multimeter. Before the tests, the conductive RSF ends were firmly fixed to multimeter test leads. The conductive RSF length between two leads was fixed to 10 cm for all of the tests. To record the resistances of conductive RSFs at different RH, a conductive RSF was gradually incubated at various relative humidity levels controlled by specific saturated salt solutions with known relative humidity: $K_2CO_3$ (43%); NaBr (59%); KI (70%); NaCl (75%) and KCl (85%). In terms of finger-touching and breathing measurements, the conductive RSFs with the length of ~15 cm were woven into clothes and masks, and their ends firmly fixed to multimeter test leads. The whole processes of time-response measurements were recorded by video camera, the related time and resistance values were directly extracted from each frame of recorded video with a time resolution of ~0.3 s.

Results

Figure 11:
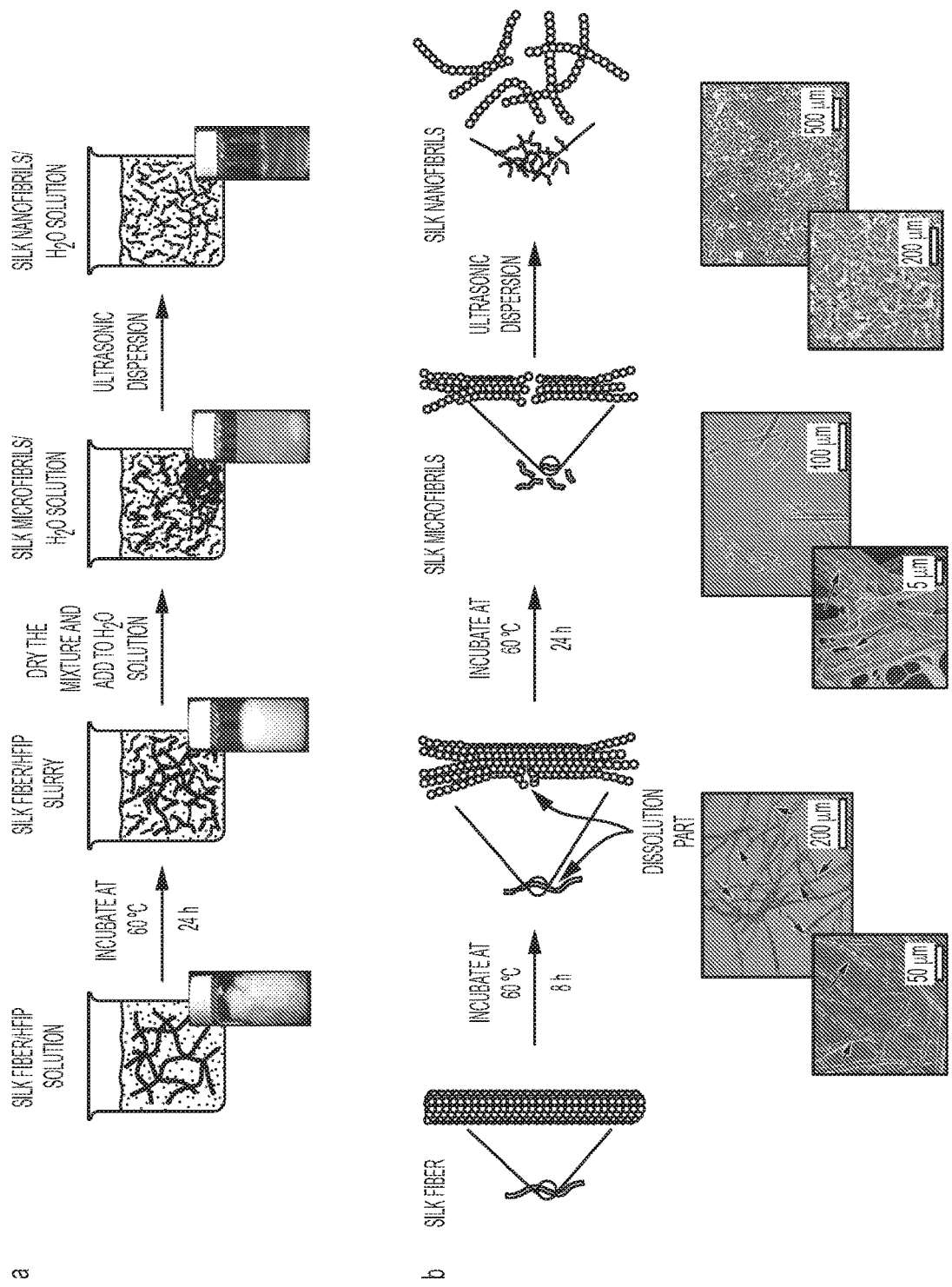
FIG. 11 shows (a) a flow chart depicting an exemplary provided process, and (b) a flow diagram with exemplary photographs depicting the structure of certain provided embodiments as the material progresses through an exemplary provided process from native silk fibers to exfoliated silk nanofibrils.
Figure 12:
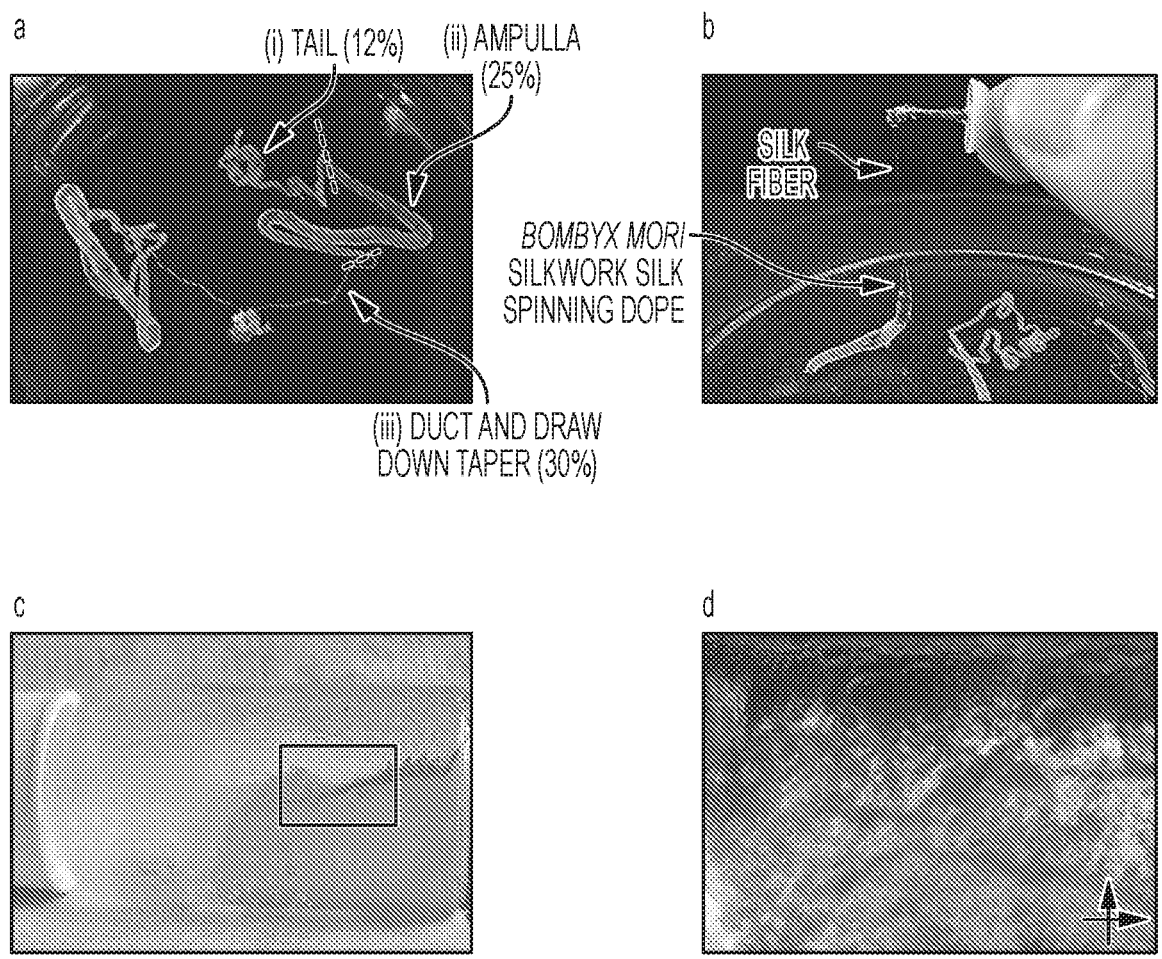
FIG. 12 shows exemplary images of B. mori silkworm gland and silk fiber/HFIP mixture. (a) B. mori silkworm gland. (b) silk spinning dope. The pictures show that silk fibers can be directly formed by drawing the spinning dope. (c, d) the silk microfibril/hexafluoroisopropanol (SMF/HFIP) solution under visual (c) and polarized light (d).
Figure 13:
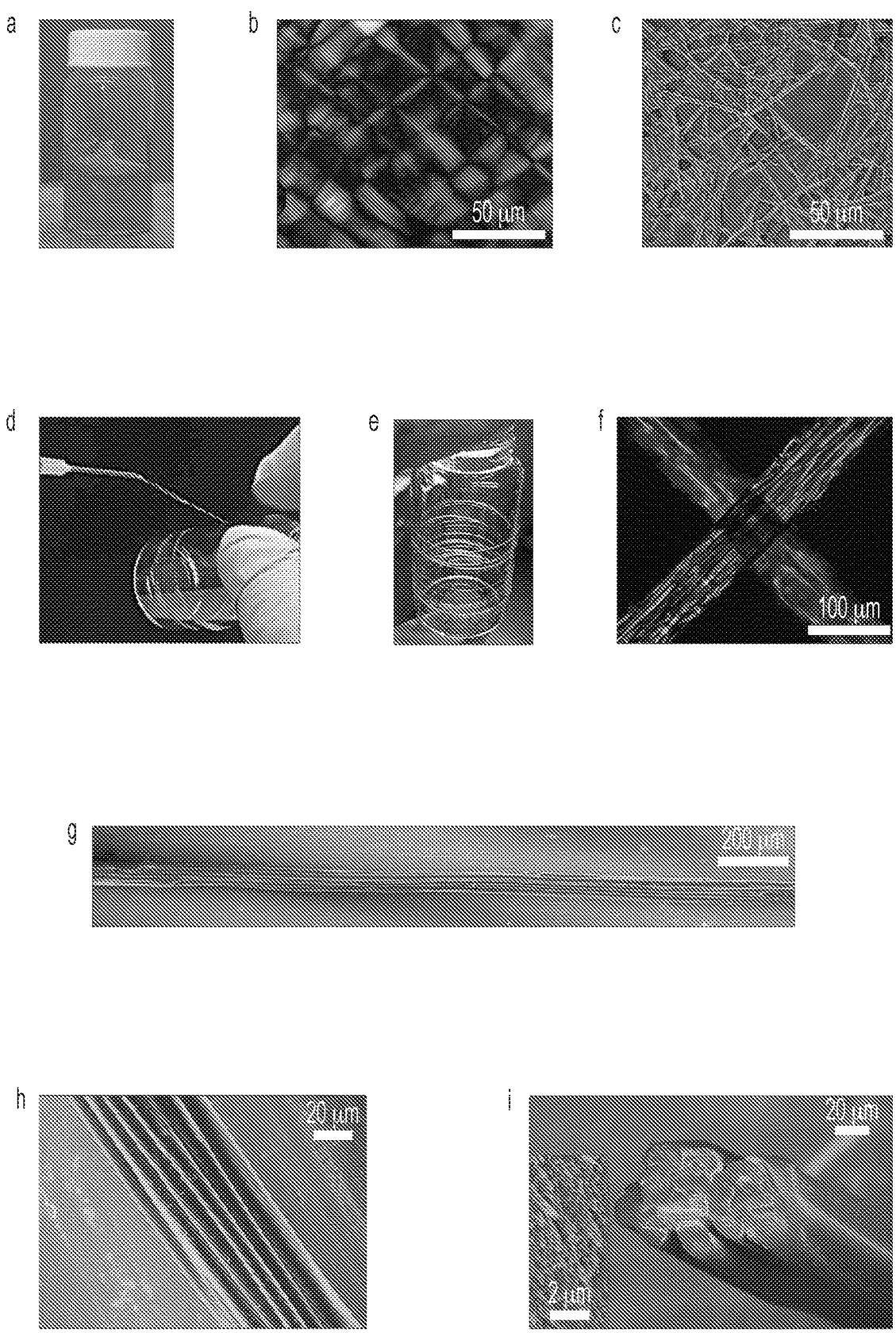
FIG. 13 shows visual appearance and structural characterization of exemplary provided regenerated silk spinning dope and resultant RSFs. (a-c) Visual appearance (a), polarized light microscopy image (b) and SEM image (c) of B. mori silk fiber/HFIP mixture with a weight ratio of 1:20 after incubation at 60° C. for 15 days. After 15 days the silk fiber partial dissolved to microfibers with diameters of 5-10 μm and contour lengths of several hundreds to thousands of micrometers. The resultant silk fiber/HFIP mixture was a uniform, highly viscous solution with nematic liquid-crystal-like texture. (d) The photograph to show the facile biomimetic spinning process. The nematic SMF/HFIP solution can be directly reeled to form RSFs. (e, f) Visual appearance (e) and polarized light microscopy image (g) of as-spun RSFs. (g-i) SEM images of as-spun RSFs. The images (h) and (i) are a top view and cross-sectional SEM images of RSF, respectively. The RSF is constituted by highly oriented and bound SMFs. The insert of the image (i) is high-resolution SEM image of a cross-section of RSF. Well-organized silk nanofibrils are observed.
Figure 14:
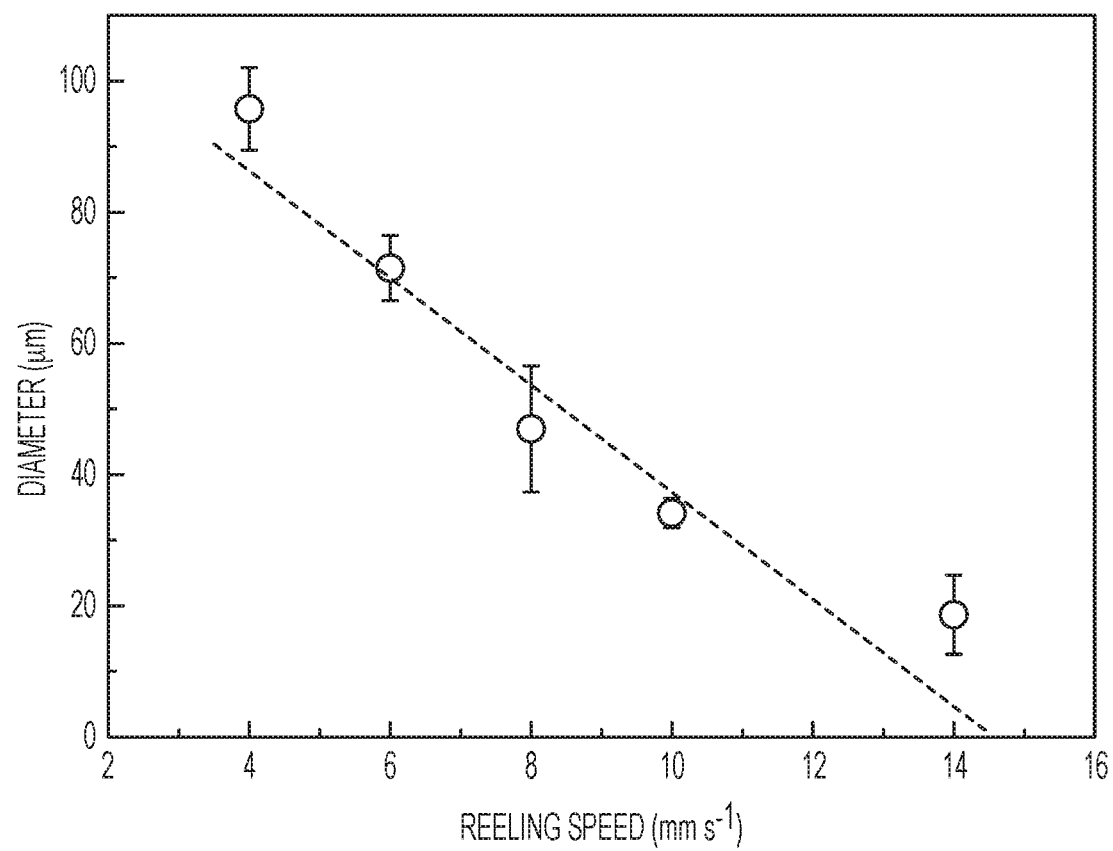
FIG. 14 shows exemplary results on the relationship between reeling speed and diameter of the certain provided RSFs.
Figure 15:
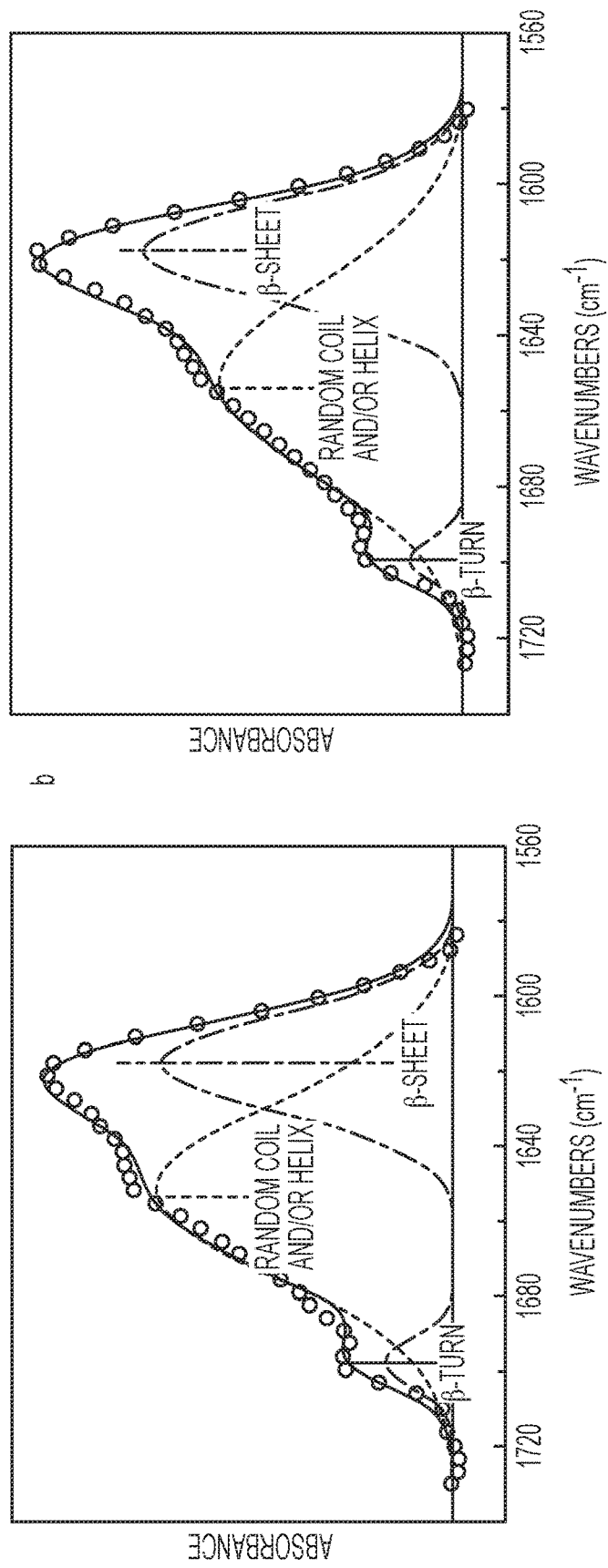
FIG. 15 shows deconvolution of the FTIR amide I band of RSFs (a) and degummed silk fibers (b). The FTIR spectra used for deconvolution were recorded by random aligned RSF and degummed silk fiber samples.

In this Example, SMF solution were prepared as previously described by dissolving degummed silk fibers in HFIP solution. By increasing the weight ratio of silk fiber/HFIP to 1:20 and extending the incubation time to 7-15 days, concentration and viscosity of the SMF solution are enhanced, which is more suitable for generating a spinning dope. The resultant silk fiber/HFIP mixture presents as a uniform viscous solution (FIG. 12, panel c, FIG. 13, panel a) with nematic liquid-crystal-like texture (FIG. 12, panel d, FIG. 13, panel b). In the solution, the silk fibers are partially dissolved to form the microfibrils, with diameters ~5-10 μm and contour lengths about several hundreds to thousands of micrometers (FIG. 13, panel c). Specifically, analogous to the characteristic of nematic silk proteins in silk glands, these SMFs form a substance that flows as a liquid but maintains some of the orientational order characteristics of a crystal (FIG. 11, panel b, and FIG. 28, panel d). These liquid crystals allow the viscous SMFs to flow through the spinneret to form complex alignment patterns under minimum shear and stress. The result is an SMF solution that can be easily transformed into a hardened fiber with minimal external forces and relatively simple devices. For instance, highly oriented uniform fibers can be directly collected by continuous extrusion or forcibly reeling the SMF solution (see FIG. 13, panels d-g). FIG. 13, panels h and i present a typical surface and cross-section morphologies of the RSFs with tightly stacked SMFs (FIG. 13, panel h). The SMFs fuse together and align along the fiber axis without gaps or cracks among the SMFs in a cross-section direction (FIG. 13, panels f-i). Additionally, the diameters of RSFs are tunable by controlling the extrusion and reeling speed. The average diameter varies from 96±6 to 19±6 μm with reeling speeds from 4 to 14 mm s$^{-1}$, respectively (FIG. 14). Fourier transform infrared spectroscopy (FTIR) characterization reveals that the RSFs are mainly composed of β-sheet (crystalline) structures. The deconvolution of the amide I band provides an estimation of β-sheet structure in the RSFs of 34±5%, while that of the degummed native silk fibers is 38±4% (FIG. 15).

Figure 16:
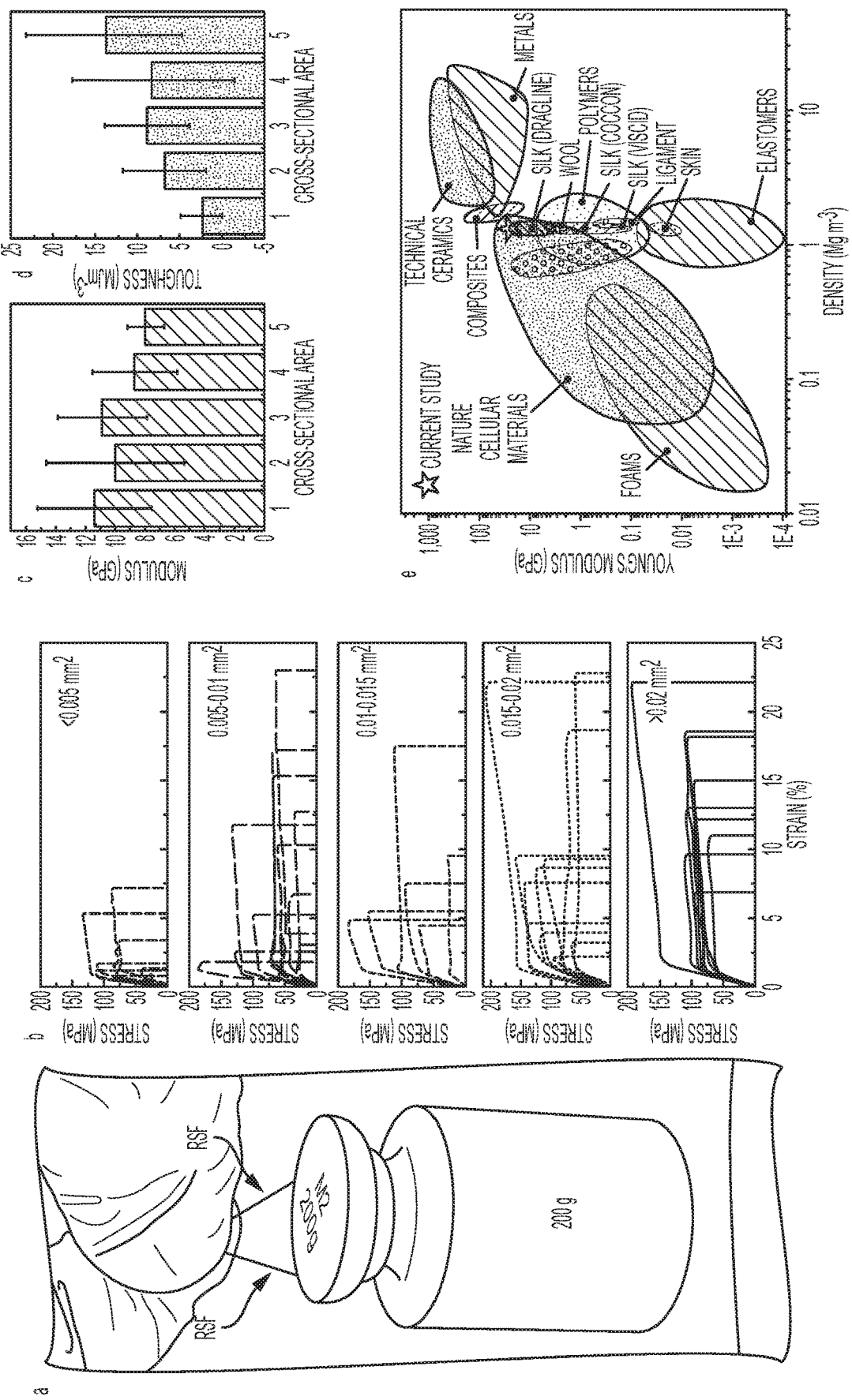
FIG. 16 shows the results of analyses on the mechanical properties of certain exemplary RSFs. (a-c) A photograph to show a single RSF (7 mg) can hold up a 200 mg weight without breaking. (b-d) Tensile stress-strain curves (b), modulus (c), and toughness (d) of RSFs. In order to evaluate the relationship between dimensions and mechanical properties, the mechanical properties of RSFs are divided into five categories according to their cross-sectional areas (CSA). Sort 1: CSA, <0.005 $mm^2$; Sort 2: CSA, 0.005-0.01 $mm^2$; Sort 3: CSA 0.01-0.015 $mm^2$; Sort 4: CSA, 0.015-0.02 $mm^2$; Sort 5: CSA, >0.02 $mm^2$. (f) Comparison of Young's modulus and densities of RSFs with other materials.

The RSFs exhibit excellent mechanical performance, since the RSFs retain the structural hierarchy and well-organized silk nanofibrils structures of native silks (see inset of FIG. 13, panel i), which is critical for enhanced strength, extensibility, and toughness of silk fibers. A single 7 mg RSF fiber, as an example, can hold a 200 mg weight without breaking (FIG. 16, panel a), which is 29 times its own weight. Tensile tests were carried out to measure the specific mechanical properties of the RSFs. To decode their relationship between dimensions and mechanical properties, the mechanical properties of RSFs are divided into five categories according to their cross-sectional areas (FIG. 16, panels b-d, Table 2). The minimum average modulus of RSFs is 8±1 GPa (5$^{th}$ sort, cross-sectional areas >0.2 mm$^2$) (FIG. 16, panel c), which is significantly higher than other reported as-spun RSFs (Table 3) and comparable with native silkworm silks. The maximum modulus of RSFs can reach up to 19 GPa, more than 2.7 times higher than *B. mori* cocoon silk (7 GPa), and higher than that of *Araneus* major ampullate gland silks (10 GPa) and most other natural biomaterials (FIG. 16, panel f).

TABLE 2

Mechanical properties of as-spun SNFs.

| Category NO. | Cross-sectional area (mm$^2$) | Stress (MPa) | Strain (%) | Modulus (MPa) | Toughness (MJ m$^{-3}$) |
|---|---|---|---|---|---|
| 1 | <10.005 | 93 ± 31 | 4.5 ± 3.8 | 11 ± 4 | 2.4 ± 2.4 |
| 2 | 0.005-0.01 | 98 ± 45 | 9.4 ± 7.6 | 10 ± 5 | 6.8 ± 4.9 |
| 3 | 0.01-0.015 | 133 ± 35 | 8.1 ± 5.3 | 11 ± 3 | 8.8 ± 5.0 |
| 4 | 0.015-0.02 | 106 ± 44 | 8.1 ± 7.2 | 9 ± 3 | 8.2 ± 9.5 |
| 5 | >0.02 | 109 ± 34 | 14.0 ± 4.9 | 8 ± 1 | 13.9 ± 9.2 |

TABLE 3

Comparison of mechanical properties of regenerated silk fibers.*

| Spinning dope$^b$ | Coagulation bath | Post-spin draw | Strength (GPa) | Extensibility (%) | Modulus (GPa) | Mechanical properties of as-spun fibers (stress; strain; modulus)$^c$ |
|---|---|---|---|---|---|---|
| RSF/CaCl$_2$/water, 15 wt % | (NH$_4$)$_2$SO$_4$ | 9 (water) | 0.31 | 37 | — | U.C. |
| RSF/water, 15% w/v | (NH$_4$)$_2$SO$_4$ | 4 (water) | 0.26 | 78.9 | | Very weak |
| RSF/water, 13-19% w/v | (NH$_4$)$_2$SO$_4$ | 6.0 (water) | 0.39 | 32.1 | 15.2 | U.C. |
| RSF/water, U.C. | (NH$_4$)$_2$SO$_4$ | No | 0.29 | 20-25 | U.C. | U.C. |
| RSF/water, U.C. | (NH$_4$)$_2$SO$_4$, Na$_2$SO$_4$ | No | 0.29 | 10.1 | U.C. | U.C. |
| RSF/LiBr·H$_2$O—EtOH—H$_2$O, 20 wt % | MeOH | 3.2 (61° C. water) | 0.12 | 11 | 6.2 | 0.078 GPa; 1.7%; 5.1 GPa |
| RSF/water, 20-30% w/v | MeOH | No | Very weak | 1.5 | U.C. | very weak |
| RSF/95% formic acid, 13% w/v | MeOH | 3 (MeOH) | 0.98 | 29.3 | 36.3 | 0.295 GPa, 2.54%, 30.4 GPa |
| RSF/TFA, 13% w/v | MeOH | 3 (MeOH) | 0.92 | 18.1 | 41.4 | 0.275 GPa, 1.33%, 28.1 GPa |
| RSF/98% formic acid, 19% w/v | MeOH | 5 (70° C. water) | 0.25 | 17 | U.C. | very weak |
| RSF/90% formic acid + 10% LiCl, 15 wt % | MeOH | 4 (MeOH) | 0.18 | 10 | 6.9 | 0.045 GPa, 1.2%, 4.0 GPa |
| RSF/98% formic acid, 15% w/v | MeOH | 4.5 (MeOH) | 0.27 | 14.1 | U.C. | U.C. |
| RSF/HFIP, 15 wt % | MeOH | 4 (MeOH) | 0.55 | 8.9 | 13.2 | U.C. |
| RSF/HFIP, 10 wt % | MeOH | 3 (water) + steam | 0.19 | 18 | 4.7 | U.C. |
| RSF/HFA·3H$_2$O, 10 wt % | MeOH | 3 (water) + steam | 0.18 | 16 | 4.2 | U.C. |
| RSF/NMMO—H$_2$O, 17 wt % | MeOH | 7.2 (water) | 0.32 | 6 | 12.2 | U.C. |
| RSF/NMMO—H$_2$O, 17 wt % | MeOH | 5.2 (water) | 0.35 | 7 | 14.2 | 0.046 GPa, 0.75%, 6.6 GPa |
| RSF/EMIMCl, 10 wt % | MeOH | 2 (MeOH) | Brittle | U.C. | U.C. | U.C. |
| RSF/NMMO·H$_2$O, 20 wt % | MeOH | 3.6 (MeOH) | 0.40 | U.C. | U.C. | U.C. |
| RSF/HFIP, 16% w/v | MeOH | 3 (MeOH) | 0.422 | 15 | 9.3 | U.C. |
| RSF/HFA, 16% w/v | MeOH | 3 (MeOH) | 0.295 | 18 | 9.8 | U.C. |
| RSF/NMMO·H$_2$O, 13 wt % | EtOH | 2.7 (EtOH) | 0.12 | 35 | 8.7 | 0.043 GPa, 2.2%, 2.6 GPa |
| RSF/NMMO·H$_2$O, 17 wt % | EtOH | 2.8 (EtOH) | 0.13 | 14 | 7.2 | U.C. |
| RSF/NMMO·H$_2$O, U.C. | EtOH | 2.0 (EtOH) | 0.12 | 8.6 | 7.2 | 0.043 GPa, 1.1%, 3.8 GPa |
| RSF/NMMO·H$_2$O, U.C. | EtOH | 3.8 (EtOH) | 0.13 | 12 | 5.3 | 0.043 GPa, 1.1%, 3.8 GPa |
| RSF/water, 30% w/v | MeOH/CH$_3$COOH | 3 (MeOH/CH$_3$COOH) | 0.41 | 34 | U.C. | ~0.06 GPa, ~4%, U.C. |
| RSF/water, 39% w/v | air | No | 0.13 | 9.6 | 7.18 | Very brittle |
| RSF/CaCl$_2$/Water, 38-47 wt % | air | 4 (80 v/v% EtOH/water) | 0.49 | 12.7 | 10.5 | U.C. |
| SF/CaCl$_2$/formic acid, 25% w/v | air | 2 (EtOH) | 0.23 | 7.3 | — | 0.123 GPa, 12.3%, U.C. |

TABLE 3-continued

Comparison of mechanical properties of regenerated silk fibers.*

| Spinning dope[b] | Coagulation bath | Post-spin draw | Strength (GPa) | Extensibility (%) | Modulus (GPa) | Mechanical properties of as-spun fibers (stress; strain; modulus)[c] |
|---|---|---|---|---|---|---|
| RSF/CaCl$_2$/water, 50 wt % | microfluidic chip | 2 (80 v/v % EtOH/water) | 0.61 | 27 | 19 | very brittle |
| RSF/CaCl$_2$/water, U.C. | air | 2.0 (90% MeOH) | 0.16 | 14.6 | 5.3 | 0.030 GPa, 3.6%, 1.2 GPa |
| RSF/CaCl$_2$/water, U.C. | air | 2.0 (80% MeOH) | 0.20 | 55.4 | 6.8 | 0.030 GPa, 3.6%, 1.2 GPa |
| RSF/CaCl$_2$/water, U.C. | air | 2.0 (90% isopropanol aqueous solution) | 0.19 | 4.4 | 4.8 | 0.030 GPa, 3.6%, 1.2 GPa |
| RSF/CaCl$_2$/water, U.C. | air | 2.0 (Saturated (NH$_4$)$_2$SO$_4$ solution) | 0.05 | 2.6 | 3.0 | 0.030 GPa, 3.6%, 1.2 GPa |
| RSF/CaCl$_2$/water, 20 wt % | air | EtOH | 0.36 | 55 | U.C. | 0.063 GPa, ~5%, U.C. |
| RSF/CaCl$_2$/water, 40-60 wt % | air | 4 (80 vol % EtOH) | 0.36 | 34 | U.C. | 0.079 GPa, 10.6%, U.C. |
| Regenerated N. edulis spidroin/water, 0.08 wt % | air | No | 0.11-0.14 | 10-27 | 6.0 | All data are as-spun fibers |
| N. clavipes spidroin/HFIP, 2.5 wt % | Acetone | 3.5 (acetone) | 0.32 | 4-8 | 8.0 | very weak |
| N. clavipes spodroin/HFIP, 289.4 kDa, 20% w/v | 90% MeOH | 5 (U.C.) | 0.508 | 15 | 21 | U.C. |
| N. clavipes spidroin 1 (DP-1)/HFIP, U.C.,20% | isopropanol | 2 (150° C. isopropanol) | 0.14 | 103 | 4.6 | U.C. |
| A. diadematus ADF-3/water, 60 kDa, 10-28% w/v | MeOH-water | 5 | 0.26 | 43 | 12.7 | U.C. |
| N. clavipes Flag, MaSp like fusion proteins/HFIP, 58 kDa, 25-30% w/v | 90% isopropyl alcohol | U.C. | 0.05 | 34 | 1.1 | U.C. |
| N. clavipes MaSp1/HFIP, 46 kDa, 30% w/v | 100% isopropanol | 3 (75% isopropanol/water) | 0.016 | 1.5 | 3.11 | 0.016 GPa, 1.46%, 1.06 GPa |
| N. clavipes MaSp1/HFIP, 70 kDa, 30% w/v | 100% isopropanol | 3 (75% isopropanol/water) | 0.036 | 3.1 | 5.7 | 0.035 GPa, 3.13%, 2.78 GPa |
| A. aurantia MaSp2/HFIP, 63 kDa, 10-12 wt % | isopropanol | No | 0.006 | 1.5 | 0.005 | All data are as-spun fibers |
| A. aurantia MaSp2/HFIP, 67 kDa, 10-12 wt % | isopropanol | No | 0.002 | 19.0 | 0.00004 | All data are as-spun fibers |
| A. aurantia MaSp2/HFIP, 71 kDa, 10-12 wt % | Isopropanol | No | 0.05 | 3.6 | 0.04 | All data are as-spun fibers |
| A. diadematus eADF3/water, 60 kDa, 10-15% w/v | Water/ isopropanol | 6 (Water/ isopropanol) | 0.383 | 95 | 3 | 0.054 GPa, 7%, 2 GPa |
| N. clavipes MaSp1, MaSp2 inspired protein/HFIP, 50 kDa, U.C. | Isopropanol | 5 (heat treatment in steam) | 0.35 | 42 | 6.3 | U.C. |

TABLE 3-continued

Comparison of mechanical properties of regenerated silk fibers.*

| Spinning dope[b] | Coagulation bath | Post-spin draw | Strength (GPa) | Extensibility (%) | Modulus (GPa) | Mechanical properties of as-spun fibers (stress; strain; modulus)[c] |
|---|---|---|---|---|---|---|
| *N. clavipes* MaSp2, Flag/HFIP, 58 kDa, 26-27% w/v | 90% isopropyl alcohol/10% water coagulation bath | 2-2.5 (90% v/v isopropyl alcohol) | 0.123 | 17.2 | 5.5 | 0.023 GPa, 46.9%, 0.5 GPa |

*=The blue (rows 1-26) and red regions (rows 27-36) are mechanical properties of regenerated silkworm silk fibers, the blue and red region are spun by wet-spinning and dry-spinning method, respectively. The green region (rows 37-50) is mechanical properties of regenerated and recombinant spider silk fibers.
[b]Spinning dope is expressed as "solute/solvent, concentration",
[c]The mechanical properties of as-spun fibers (without any post-treatments) are expressed as: stress (GPa), strain(%), modulus (GPa).
RSF = regenerated silk fibroin;
ADF-3 = Araneus diadematus (MaSp2) fibroin 3;
eADF-3 = engineered variants of Araneus diadematus (MaSp2) fibroin 3;
TFA = ;
HFIP = ;
NMMO = ;
HFA = ;
EMIMCl = ;
U.C. = unclear.

Figure 17:
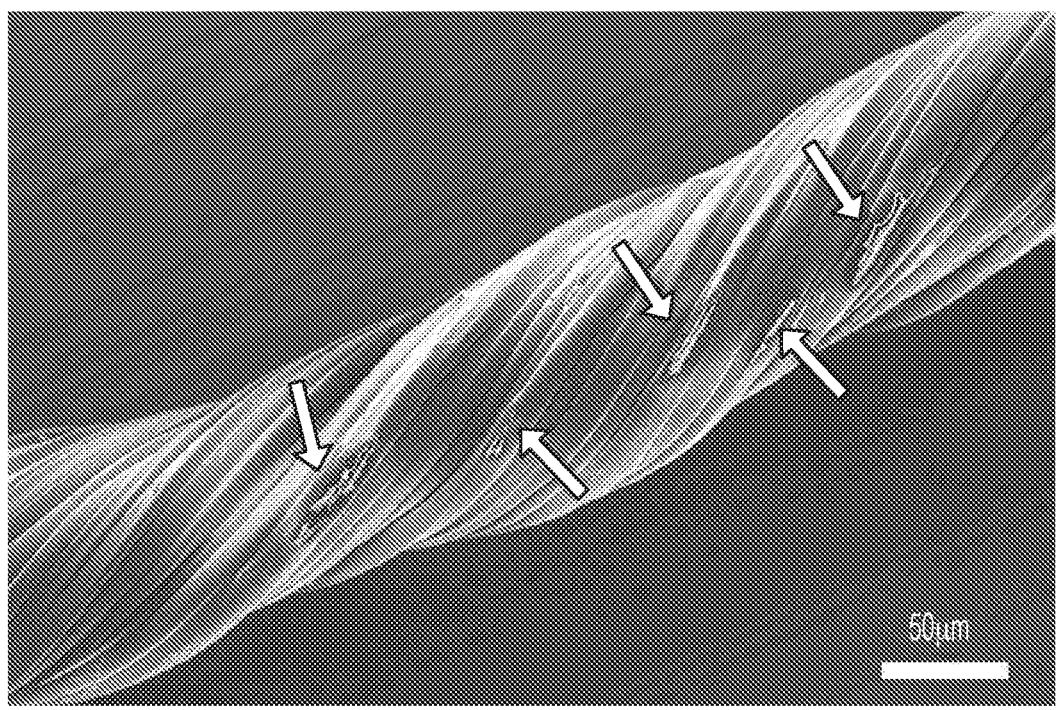
FIG. 17 shows the defects of an exemplary RSF, highlighted by black arrows.

By progressively increasing the cross-sectional area from <0.005 (1$^{st}$ sort) to >0.2 mm2 (5$^{th}$ sort), the tensile modulus of RSFs decreased from 11±4 to 8±1 GPa (FIG. 16, panel c), while the toughness increased from 2±2 and 14±9 MJ m$^{-3}$ (FIG. 16, panel d). Interestingly, this trend is different from the relationship between dimensions and mechanical properties of native silks. For native silks, the elastic modulus and ultimate tensile strength decrease with increase in silk diameter, while strain and toughness do not change in relation to the fiber diameter. Careful observation of RSFs reveals that the surface of RSF has a few defects (FIG. 17). Defects are a critical factor that influences the mechanical behavior of materials, thus, the unique diameter-toughness relationship of RSFs originates from the defects. Our previous studies have shown that the diameter of the spider silk fiber plays a crucial role in affecting the fracture mode and toughness modulus of the fiber at the small size, because of the interplay of β-sheet nanocrystals and semi-amorphous protein domains. However, comparing to the critical thickness value (H*) of 22 nm, our thinnest RSF with the diameter (H) of 19±6 μm is far from the scale region that will be affected by this nanoscale size-effect ($\sqrt{H^*/H}<<0.5$). Therefore, the size effect as discovered in the experiment in the current study is likely caused by mechanisms at the larger-scale level, and a computational model different from the former works is needed to study the mechanics of the silk fiber.

Figure 18:
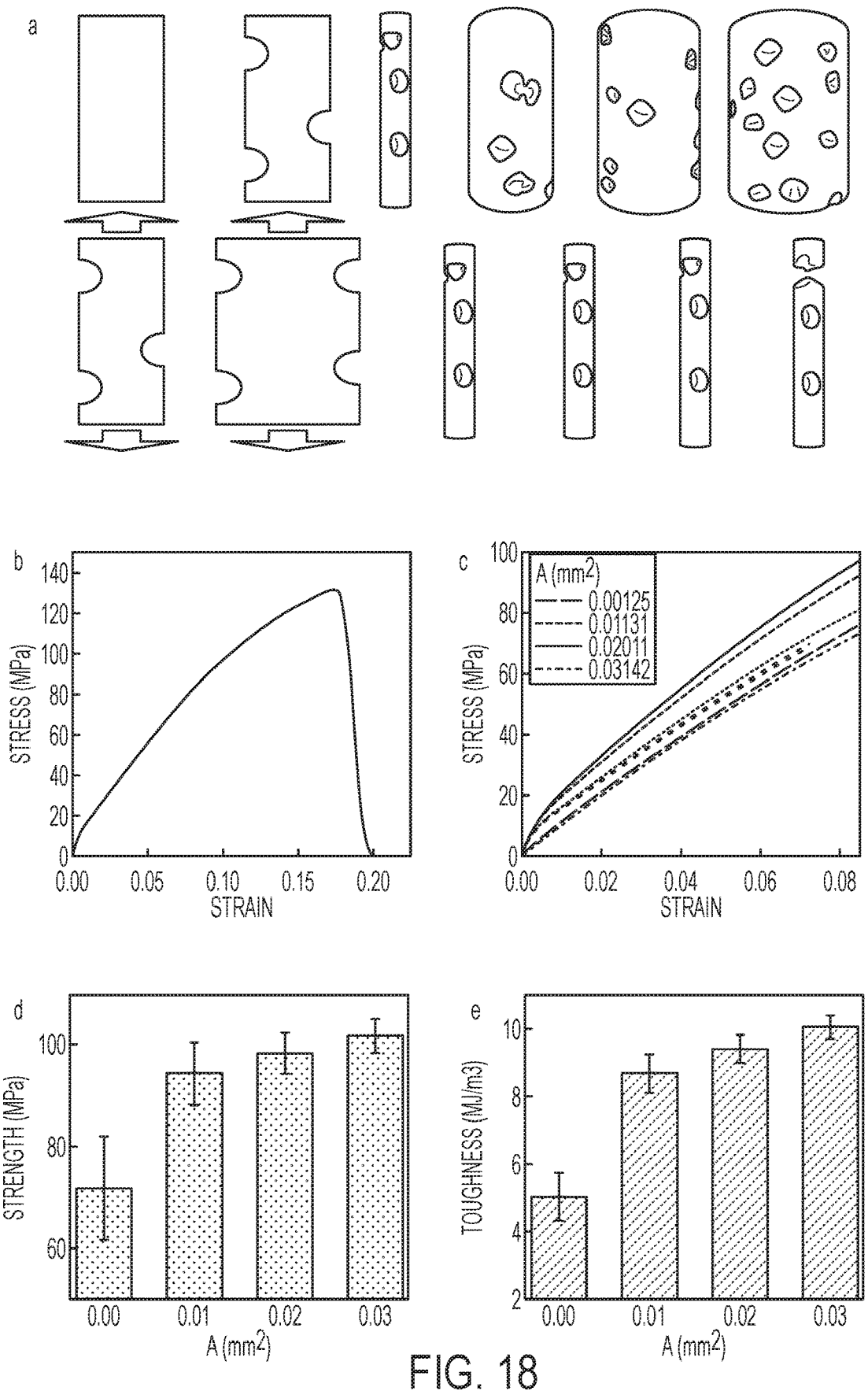
FIG. 18 shows computational modeling of an exemplary silk fiber with defects and the simulation results of the mechanical response under tensile loading. (a) Schematics and snapshots (above) of simulation models of silk fibers of different diameter (A=0.00125, 0.01131, 0.02011, 0.03142 mm² from left to right) but the same defect rate on the outmost surface and schematics and snapshots (below) of simulation trajectory of the silk fiber (A=0.00125 mm²) under tensile loading from equilibrium up to failure. (b) The stress-strain curve of a pristine silk fiber under tension (c) The stress-strain curve of defected silk fibers under tension (10 models and corresponding tests for each fiber cross section area) (d-e) The statistical results of the strength and toughness of the silk fibers of different radii.

A computational model based on elastic network features is therefore used to quantify and explain how silk fiber toughness increase with diameter. The computational models, (FIG. 18, panel a) are solid cylinders of different diameters with defects. Considering the observations that defects and irregular structures generally take place on the outmost surface of the fiber (FIG. 17), we model each defect as a hemisphere vacancy of 0.02 mm in diameter on the fiber surface. The number of defects is proportional to the outmost surface of the fiber and they are randomly distributed on the fiber surface (FIG. 18, panel a). By applying uniaxial tension force to the computational model, we are able to deform the material up to mechanical failure. The stress-strain curves are recorded for each of the pristine fibers (FIG. 18, panel b) and defect samples (10 different models with random defect distributions for each tested diameter, FIG. 18, panel c) and statistically summarize the strength as peak stress and material toughness as the integration of area below the stress-strain curve (FIG. 18, panels d-e), respectively. The existence of defects on the RSF surface has a more significant negative effect on the strength and toughness of silk fibers with small diameters, as the strength and toughness increase from 71.9±10.0 MPa and 5±0.7 MJ/m$^3$ for RSF of 0.00125 mm$^2$ to 101.8±3.3 MPa and 10.1±0.3 MJ/m$^3$ for RSF of 0.03 mm$^2$ in cross section area, respectively.

There are many unique advantages of RSFs. As in natural spinning, a unique advantage of our biomimetic spinning system is the 3D printing-like spinning process, to directly build 1-3 dimensional structures (FIG. 19, panels a-f) during spinning without additional processes. Therefore, this biomimetic spinning approach provides a new approach to utilize silks to generate polymorphic hierarchical RSFs with useful structures beyond native fiber construction. For instance, a yarn-like spiral fiber can be produced by rotating the collector in a plane direction perpendicular to the fiber axis (FIG. 19, panel a and FIG. 20, panels a-h); a free-standing Towel Gourd tendril-like helix fibers are generated by extruding the spinning solution onto a cylindrical collector (FIG. 19, panel b, FIG. 21, panels a-b). In addition, the silk protein in the spinning solution has the ability to absorb different types of dyes, thus suitable for generating colored fibers, which have shown promising applications in fashion, optical devices and biomedicine. FIG. 19, panels c and d give examples of two specimens in which multicolored luminescent RSFs with parallel- and cross-double helical construction were built by adding Rhodamine B and Rhodamine 123, respectively. More complicated 2D and 3D structures can also be generated, such as robust webs and grids (FIG. 19, panels e-f, FIG. 21, panels c-d).

To assess the use of the RSFs for biomedical applications, human dermal fibroblasts were seeded on yarn-like and as-spun RSFs. Cell viability on the RSFs was assessed by live/dead staining. As shown in FIG. 19, panels g-h, cells grow well on the fibers and adapt to the fiber surface topography and align along the fiber axes. 3D cell patterns following the contour of the RSF templates are generated on RSFs of different hierarchical structures (FIG. 19, panels i-j). In contrast, cells do not form defined cellular patterns on randomly arranged silk fibers (FIG. 22). Such macroscopically aligned constructs may be a suitable template to generate highly aligned tissues, such as in muscle fibers, spinal cord and tendons. Many organ and tissues, such as blood vessels, intestine and esophagus, are characterized by hierarchically arranged curved morphologies. To reconstruct these types of tissues in vitro, tubular structures are able to generate from RSFs to guide cell and matrix alignment and assembly.

Structural hierarchy endows natural silks with fascinating physical properties. A typical example is the ultra-low temperature toughness of silks; silk fibers exhibit ductile failure even at the temperature of liquid nitrogen (−196° C.), and breaking elongation does not differ from the behavior seen at room temperature. Another example is the unique fracture mode and tensile behavior of notched silks; crack direction derives from the notch can be deflected to fiber longitudinal direction due to the longitudinally arranged silk nanofibrils in silks. The RSFs reserve the structural hierarchy of natural silks, so we further evaluate the fracture behavior and ultra-low temperature mechanical performance of RSFs. To estimate the flexibility of RSFs in ultra-low temperature, a helical fiber was immersed in liquid nitrogen and then stretched to uncoil the helical structures (FIG. 19, panel k). The fiber is resilient (recoiled) immediately after being taken out of the liquid nitrogen. In contrast, other materials that are flexible at room temperature, such as cellulose paper and nitrile rubber, loose elasticity or break during immersing in liquid nitrogen (FIG. 23, panels a-d). The same fracture mode with natural silks is also observed in RSFs (FIG. 19, panels l-n). In these experiments, an artificial notch was introduced in RSF, and the mechanical properties were tested to compare with that of the adjacent intact (un-notched) fiber (FIG. 24, panels a-b). The notched RSF exhibits the same load-strain curve as the un-notched RSF (FIG. 19, panel l); only the strain is reduced. This mechanical feature is the typical ductile fracture behavior of natural silks. Cross-sectional SEM image (FIG. 19, panel m) of notched RSFs after tensile fracture confirms the ductile fracture behavior. Three distinct fracture regions are shown (i-iii, as shown in insert scheme of FIG. 19, panel m): the notched area (region i), the crack stable growth area (region ii), and the crack unstable growth area (region iii). The locally amplified SEM image (FIG. 19, panel n) in the crack stable growth area reveals that the silk nanofibrils pulled out along the tensile direction after fracture. As with native silks, the crack growth direction is deflected from the fiber cross-section direction to the longitudinal direction.

The utility of these RSFs can be expanded by incorporating inorganic functional components. For example, the RSFs are able to construct towards wearable humidity and temperature sensors via a three step dip-coating method, which is selected to build core-shell-based conductive fibers is because it is easy to implement and maintains the excellent mechanical properties of RSF (see FIG. 25). Briefly, multi-wall carbon nanotubes (MWCNT) were dispersed in formic acid/$Ca^{2+}$ with 1 h sonication, followed by dissolving the degummed silk fibers in this solution with intense shaking. Then, the WMCNT/silk/$Ca^{2+}$ ink was coated onto RSFs and dried at room temperature to eliminate the formic acid (FIG. 25, panel a). The conductive coating layer closely bonds with the RSFs (FIG. 25, panels c-e, FIG. 26) since the formic acid/$Ca^{2+}$ solvent system dissolve the surface of RSFs. More significantly, the $Ca^{2+}$ ions in the coating layer capture water from the environment through coordination complexes; a $Ca^{2+}$ ion can coordinate 6-8 water molecules via the oxygen atoms. As shown in FIG. 25, panel f, the higher relative humidity (RH) in the environment, the more water that can be captured in the coating layer. Therefore, the coating layer gradually swells and the distance between WMCNTs widens progressively with the increase of RH. These processes are reversible. Once the RH is reduced to the initial value, the coating layer dimension and WMCNT distances could recover to their starting states. As a result, the resistance of WMCNT/silk/$Ca^{2+}$ coatings is very sensitive to humidity changes (FIG. 25, panels g-j).

FIG. 25, panel g reveals the relationship between RH and resistance. When the RH increases from 43% to 85%, the resistance increase gradually from 58.4±0.1 to 83.2±0.1 kΩ. After four cycles, the resistances are similar at the repeated same RH, demonstrating the reversibility of the process. A time-resolved resistance vs RH experiment (FIG. 25, panel h and FIG. 27) was designed to evaluate the response rate related to the change in RH. A conductive RSF was fixed on the top of a 2 L glass bottle, then, the ~50 mL 50° C. water was added to the bottom of the bottle. The temperature of RSF position was kept at 24-25° C. and no changes were detected during the test process. We find that the resistance of the RSF increases after 4 seconds by adding the water to the bottle (FIG. 25, panel i). Considering the diffusion rate of water vapor, the resistance is synchronous in ascending with the increase of RH, and more rapidly than a commercial hygrometer (15 sec). Significantly, the resistance of conductive RSF varies in this time-resolved process, and is more sensitive to RH changes than a commercial hygrometer, which offers a step-wise response. The conductive RSF also quickly responds to changing temperature (FIG. 25, panel j); the resistance of RSF decreases with increased temperature. After standardization of the resistance to initial temperature, the plot coincides with recordings from a commercial thermometer. These rapid responses to humidity suggest that these conductive RSFs could be utilized in clothes and masks toward smart fabrics to sense and monitor touching and breathing. As presented in FIG. 25, panels k and l, the resistances respond real-timely upon touching the cloth with a finger (FIG. 25, panel k) or breathing (FIG. 25, panel l), and rapidly recover to the original state once the stimulus was removed. The utility of wearable devices depends on performance and also affordability. Most advanced wearable devices include carbon nanotubes, graphene, and noble metal nanomaterials, and most preparations are sophisticated with significant costs. However, the cost of conductive RSFs was approximate $0.022 per centimeter (Table 4). These RH and temperature sensitive wearable SNFs may find applications in wearable sensors, considering the biocompatible nature of the composites, even in medical implants.

TABLE 4

The estimated total cost for preparing 1 meter of conductive RSF on the basis of the information available.

| Composites | Used materials and chemicals | Amount used | Unit cost US $* | Cost US$ | Total chemical and material cost (US $ per meter of fiber) | Other costs increasing factors or remarks |
|---|---|---|---|---|---|---|
| RSF (Length: 1 m; Diameter: 200 μm; Density: 1.3 g/cm3) | Silk fiber | 0.04 g | 0.015/g | 0.0006 | 2.1046 | Degumming and heating |
|  | HFIP | 0.8 g | 2.63/g | 2.104 |  |  |
| SF/WMCNT/Ca$^{2+}$ coating (Length: 1 m; Thickness: 20 μm; WMCNT:SF = 80:20 w/w; Density: 1.1 g/cm3) | Silk fiber | 0.012 g | 0.015/g | 0.0006 | 0.1102 |  |
|  | WMCNT | 0.003 g | 7.88/g | 0.0236 |  |  |
|  | CaCl2 | 0.015 g | 0.343/g | 0.05 |  |  |
|  | Formic acid | 0.3 mL | 0.12/mL | 0.036 |  |  |
| Conductive RSF |  |  |  |  | $2.2 per meter[b] |  |

*The prices of chemical reagents, carbon nanotubes were obtained from Sigma-Aldrich website (www.sigmaaldrich.com/united-states.html). The price of cocoons was obtained from Alibaba website (www.1688.com/). The price of cocoons has differences, depending on the place of purchase and the type of cocoons. Here a median price was selected for the calculations. The cost of RSF can be further reduced if using industrial waste silk as raw materials.
[b]One centimeter conductive RSF can make a sensor.

Example 3—Application of Certain Embodiments to Electrical and/or Optical Devices Materials and Methods The Example offers, among other things, examples of how provided methods and compositions may be used to provide or enhance electrical and/or optical devices. Unless otherwise stated, the methods and processes used in this Example were as follows:

Preparation of Degummed Silk Fibers

Bombyx mori (B. mori) silkworm cocoon silk fibers were degummed by boiling in two 30 min changes of 0.5% (w/w) NaHCO$_3$ (Sigma-Aldrich) solution. Then the degummed silk fibers were washed with distilled water and allowed to air dry at room temperature.

Liquid Exfoliation of Silk Nanofibrils (SNFs)

The degummed B. mori silk fibers were immersed in HFIP solution with a weight ratio of 1:30, and sufficient oscillation was applied so that all fibers were immersed. Airtight containers with the silk fiber/HFIP mixture were incubated at 60° C. After 24 hours, the resultant SMF pulps were dried in a fume hood to evaporate the HFIP. After total drying (about 4 hours), the SMFs were put into water with a weight ratio of 1:200 with continuously stirring or oscillation, followed by the removal of the undissolved silk precipitates. Finally, the silk/water mixture was sonicated at 120 μm amplitude and 20 kHz frequency, with intervals of 10 sec (Branson Digital Sonifier 450, Branson, USA; output powder: 400 Watts). After 1 h, the exfoliated SNFs dispersion was harvested by centrifugation at 10,000 rpm for 20 min. Because the HFIP is a toxic solvent, all of these steps should be operated in a chemical hood, and necessary precautions used.

Synthesis of Gold Nanoplatelets

A 100 mL of SNF dispersion (0.1 wt %) was mixed with 1 mol/L HCl solution with vigorous stirring to adjust the solution to pH 1. Then the solution was mixed with 100 mL of 10 mmol/L chloroauric acid with vortexing to give a final mixture with a chloroauric acid concentration of 5 mmol/L. Single gold nanoplatelets were obtain by incubating the resulting solution at 80° C. for 24 h. To prepare SNF/gold hybrid membranes, the SNF/gold nanoplatelet solution was centrifuged at 5000 r/min for 10 min to remove the SNFs, and then a desired amount of fresh SNF solution was added to gold nanoplatelet precipitate under intense stirring. The resultant dispersion was vacuum filtered.

The Preparation of SNF Membranes

All of the SNF membranes were fabricated by vacuum-filtrating the SNF dispersions through a Sigma-Aldrich vacuum filtration assembly and nylon filtration membranes (pore size, 0.2 μm; diameter 47 mm; Sigma-Aldrich). The fluorescent membranes were prepared via masked vacuum-filtrating by adding Rhodamine B (Sigma-Aldrich), Rhodamine 123 (Sigma-Aldrich) and CdSeS/ZnS quantum dots (Sigma-Aldrich) solution.

Coarse-Grained Dissipative Particle Dynamics (DPD)

The DPD method was employed to study the dynamics of silk peptide chains under ultrasonic exfoliation. An introduction of the DPD model and the procedure of calculating all the interaction parameters are based on a prior report. The characteristic length, energy and mass scale were set to be the interaction cut-off radius $R_c$, $k_BT$ and the mass of one bead, respectively, and thus, $Rc=k_BT=m=1$. The intrinsic time unit of the model was $$\tau = R_C\sqrt{\frac{m}{k_BT}} )$$

and the timestep of the present simulation was 0.01τ. By mapping the model to the real system, the physical values of these parameters are, $R_{c, physical}$=9.321 Å, $k_B T_{physical}$=4.14× 10−21 J, m=2.692×10−25 kg and $\tau_{physical}$=0.75 ns. The dimensions of the simulation box were set to 30×30×30 $R_c^3$ and the total number beads in the system was 81,000, with the bead number density $\rho=3/R_c^3$, which is usually used in DPD models. In the original model, the non-bond interaction between hydrophilic beads was purely repulsive and they were easily dispersed among the water beads. In order to compensate for the lack of attractive interactions between hydrophilic beads, a Lennard-Jones potential was introduced to replace the repulsive potential.

$$U = 4\epsilon\left[\left(\frac{\sigma}{r}\right)^{12} - \left(\frac{\sigma}{r}\right)^{6}\right]$$

where the length parameter $\sigma$=0.693 $R_c$ was used to retain the equilibrium bead distance at 0.778 $R_c$, which is a result of the number density $\sigma=3/R_c3$. The energy parameter was set at $\epsilon$=0.5 $k_B T$, which was sufficient to hold the chains together when ultrasonication was not applied. This energy level was much smaller than the hydrogen bond energy in the hydrophobic beads. The interactions between hydrophobic beads were the same as in the original model.

After an equilibration of the system, the simulation box was deformed sinusoidally with a maximum bulk strain of 0.1 and period of 5τ. According to the equation of state of the DPD model, the generated pressure scales approximately linearly with the bulk strain within this range of deformation and thus, a sinusoidal pressure perturbation is generated. The amplitude of the pressure perturbation is $$5\frac{k_B T_{physical}}{R_{C,physical}^3} \approx 25 \text{ MPa}$$

and the frequency is $$\frac{1}{-5\tau_{physical}} \approx 0.27 \text{ GHz.}$$

Both parameters are much higher than the experiment conditions. The disruption of hydrophilic chains block happens in shorter time with faster and higher pressure perturbation. The parameters here are chosen in order to observe the phenomenon within the simulation time scale, and they are not expected to change the underlying mechanism.

Human Dermal Fibroblast (HDF) Responses to Silk Membranes

HDFs were cultured in Dulbecco's Modified Eagle Medium (DMEM, Invitrogen) supplemented with 10% fetal bovine serum (FBS, Sigma-aldrich), and antibiotics/antimycotics (Invitrogen). Silk membranes were cut into pieces fitting into the wells of a 48-well plate with an 8 mm biopsy punch. The membranes were sterilized by immersion in 70% ethanol for 30 min, followed by rinsing in sterile $H_2O$. HDFs were seeded at a density of $10^4$ cells/cm$^2$ on silk membranes and cultured at 37° C. in a humidified atmosphere with 5% $CO_2$. The relative number of metabolically active cells was determined by the AlamarBlue assay (Invitrogen) according to the manufacturer's instructions. Briefly, scaffolds with cells were incubated in medium supplemented with 10% (v/v) alamar blue dye for 3 h. Duplicate 100 µl aliquots of culture medium were taken from each sample and fluorescence was measured at excitation of 560 nm and emission of 590 nm with a SpectraMax M2 microplate reader (Molecular Devices). The viability of the HDFs on silk membranes was assessed by live/dead assay (Molecular Probes). The silk membranes with cells were incubated in medium containing 2 µM calcein AM and 4 µM EthD-1 at 37° C. for 15 min. The stained cells were then observed with a Keyence BZ-X710 fluorescent microscope (Keyence).

Characterization

The morphology of SNF and SNF membranes were characterized by SEM (Ultra 55 filed emission scanning electron microscope, Harvard University Center for Nanoscale Systems) at an acceleration voltage of 5 kV. To prevent electrical charging, all the specimens were deposited with a 2-nm-thick Pd/Pt layer before observation. The structure of the membranes was characterized by FTIR (Jasco FTIR-6200, Jasco Instruments, Easton, Md.). For each measurement, 64 interferograms were co-added and Fourier-transformed employed a Genzel-Happ apodization function to yield spectra with a nominal resolution of 4 cm$^{-1}$. Deconvolution of amide I bands was carried out using PeakFit 4.12. The numbers and positions of peaks were defined from the results of second derivative spectra and fixed during the deconvolution process. A Gaussian model was selected for the band shape and the band width which was automatically adjusted by the software. It should be noted that each spectrum shown was from a single experiment, but the data obtained from the spectra (e.g., β-sheet content) were the average of five separate deconvolutions from different samples. The mechanical properties of membranes were tested by using an Instron 3366 machine (vendor) in tensile mode at 25° C. and 50% relative humidity. The transmittance of the membrane was characterized by AVIV model 14 UV-Vis Spectrophotometer (vendor info). The conductivities of SNF based electronic devices were assessed using HMS-3000 Hall (vendor) Measurement System with four-point probes.

Results

FIG. 11, panel a summarizes the three-step top-down route to exfoliate natural silk fibers. First, the degummed *Bombyx mori* (*B. mori*) silkworm cocoon silk fibers were immersed in HFIP solution with weight ratio of 1:30, and were incubated in an airtight container as a silk fiber/HFIP mixture at 60° C. for 24 hours. During the incubation, the HFIP gradually permeated into the silk fibers and partially dissolved the silk from defects and ends (FIG. 11, panel b and FIG. 30, panels a-e). After 24 h, the silk fiber/HFIP mixture formed a pulp blend (FIG. 11, panel a) and was split to microfibrils with diameters of 5-50 µm and contour length of 50-500 µm (FIG. 11, panel b). SEM images revealed that these SMFs were also split off to sub-microfibrils at their ends (FIG. 11, panel b). The dried SMFs were moved into water with a weight ratio of 1:200. The undissolved silk fibers and large SMFs (contour length larger than 1 mm) twisted together and settled to the bottom after 1 min stirring or shaking (FIG. 11, panel a). Most of the SMFs remained in water during one hour. In the third step, the settled silk fibers were removed, and ultrasonication was applied to exfoliate the SMFs into SNFs. After 1 hour of ultrasonic dispersion at 120 µm amplitude, 20 kHz frequency and 20 min centrifugation at 10,000 rad to remove the precipitates, the transparent well-dispersed SNFs were obtained and were stable over several months (FIG. 11, panel a). The extracted SNFs had a diameter of 20±5 nm and a contour length in the range of 300-500 nm (FIG. 11, panel b and FIG. 31), the same as the diameters of single SNFs found in native silk fibers. Typically, 1 g of degummed silk fibers produced 100 mL SNFs aqueous solution with concentration of ~0.1 wt % after 1 hour of ultrasonic dispersion at 120 μm amplitude and 20 kHz frequency, giving a yield around 10%. The settled silk fibers and SMFs could be dissolved and dispersed again to generate higher yields of SNFs. The more detailed discussion of optimum conditions for this liquid exfoliation method can be found in FIG. 32. Notably, this liquid exfoliation method is not only suitable for *B. mori* silk fibers, but also works for the formation of other biological nanofibrils from bulk materials. For example, by using the same method, we have successfully extracted *Antheraea pernyi* (*A. pernyi*) SNFs and chitin nanofibrils from *A. pernyi* silkworm silk fibers and crab shell α-chitin powder, respectively (FIG. 33).

To help understand the mechanism involved in the liquid exfoliation of silk fibers, a coarse-grained dissipative particle dynamics (DPD) simulation was applied to the process (FIG. 34). According to the classic micelle model of silk assembly (FIG. 34, panel a), the crystalline regions (repetitive GAGAGS motifs) of silk form cores of fibroin micelles due to strong hydrophobic interactions and amorphous peptide chains (nonrepetitive motifs) which extend out from the core domains to form outer adhesion regions between fibroins. These micelles can assemble to SNFs and then to silk fibers during spinning by elongational flow and/or physical shear (FIG. 34, panel a). Without wishing to be held to a particular theory, it is contemplated that the outer amorphous (hydrophilic) regions have much weaker interactions in comparison to the strongly bound crystalline cores (hydrophobic), thus the exfoliation of the silk fibers was proposed occurring at these outer adhesion regions composed of the more hydrophilic peptide chains.

To verify this hypothesis, a molecular model was built to study the dynamics of silk chains under ultrasonic liquid exfoliation. All the simulations were performed using the large-scale atomic/molecular massively parallel simulator (LAMMPS). Decapeptide chains, each composed of 30 amorphous beads, were constructed to represent the interglobule amorphous regions in the silk fibers, which were immersed in a simulation box filled with water beads. After equilibration of the system, the simulation box was deformed sinusoidally to generate a pressure perturbation in order to mimic the ultrasonication condition. The pressure perturbation and frequency in the simulations were much higher than those in the experimental conditions, but were utilized to provide a qualitative understanding of the molecular scale ultrasonication dynamics. The recording of the radius of gyration (Rg) and snapshots of the simulation (FIG. 34, panel b) showed the evolution of the peptide chains from a condensed assembly to separate chains. During this process, the periodic deformation pumped the water beads into the structure to collide with silk beads and squeeze into spaces between the amorphous chains to result in their separation. After the disruption, the peptide chains were dispersed in the liquid. The same procedure was performed on the hydrophobic chains (FIG. 34, panel c). Because of the strong attractive interactions (hydrogen bonds formed in the crystalline β-sheet) between the hydrophobic beads and the unfavorable interactions with the water beads, the hydrophobic chains did not disperse under the same condition in which the hydrophilic regions of the assemblies were separated. Therefore, ultrasonic exfoliation disrupted the amorphous regions that linked SNFs together. Our recent simulation work also indicated that the spinning process in producing silk fibers enhanced the connections along the fiber direction, while weaker entanglements were formed in the lateral directions. Considering the weaker connections between fibroin micelles in the lateral direction, we propose that the ultrasonication exfoliate the silk fibers bundles along the fiber direction (FIG. 11 and FIG. 29).

In order to fabricate macroscopic materials a vacuum filtration process was utilized as reported previously. Since SNFs have long contour lengths and strong mechanical properties, they can withstand vacuum-filtration drying and form homogeneous membranes (FIG. 35, panel a). After complete drying, the membranes (thickness≈5 μm) appeared homogeneous, freestanding, transparent (FIG. 35, panel b), and were characterized by strong birefringence in cross-polarized light (FIG. 35, panel c), indicating the ordered nematic phase in aqueous suspensions of SNFs (FIG. 31, panel d) were maintained during the film formation process. Similar results were observed for other β-sheet based nanofibril membranes. The FTIR spectrum of SNF membrane (FIG. 36) confirmed that HFIP was totally removed from the SNF membranes.

Structural insights into the mesoscopic structure of the membranes from surface and cross-sections were obtained via SEM. A uniform fibrous and connected porous structure were evident with pore sizes of 5-20 nm (FIG. 35, panels d-f). Traditionally, as cast silk fibroin (SF) membranes dissolve in water if not be treated with alcohol or by water annealing (FIG. 37, panel a). Yet, these SNFs membranes could be immersed in water and did not undergo dissolution for more than 1 week (FIG. 37, panel b). To examine the structural details, the FTIR spectrum of SNF membrane was deconvoluted according to previous reports (FIG. 38). The deconvolution of the amide I band provided an estimation of β-sheet (crystalline) structure in the SNF membranes at 53±2%, while that of the degummed silk fibers was 38±4%. Therefore, the SNF membranes had a higher content of β-sheet, acting as crosslink points to form interlocking protein chains to keep the SF molecules stable in solvent. These results also suggest that the HFIP exfoliation process mainly impacted the random coil structures in the silk fibers, which is consistent with our suggested liquid exfoliation mechanism.

Tensile tests were carried out to measure the mechanical properties of the materials (FIG. 39). Membranes with a thickness of 200±25 μm had a modulus of 3.5±0.3 Gpa, higher than that of regenerated SNFs (2.5 GPa), silk fibroin membranes (1.5-2.7 GPa) and chitin fibrils (1.3-2.3 GPa), while comparable with other types of β-sheet based fibrils (2-5 GPa). As for toughness, the SNF membranes had values of $5\pm2\times10^5$ J/m$^3$, 5-100 times higher than that of regenerated SNFs and other types of β-sheet based fibrils ($4\times10^3$ to $9\times10^4$ J/m$^3$).

The cytocompatibility of SNF membranes was evaluated in vitro by seeding HDF. Ethanol-treated membranes were cast from aqueous SF solutions to serve as a positive control, as the cytocompatibility of aqueous-derived SF materials has been demonstrated in the past. Alamar blue assay was performed to determine the proliferation of cells cultured on both types of membranes. Cells showed a linear progression of proliferation up to day 7 followed by a plateau. In comparison to the SF membranes, no significant differences in cell proliferation were observed (FIG. 35, panel g). Cell viability on SNF membranes was assessed by live-dead staining (FIG. 35, panel h), wherein live cells stained green and the nuclei of dead cells stained red. Cells adhered and spread with healthy spindle-like morphology on both types of membranes without dead cells detected. In addition, cells reached confluence around day 7, which is consistent with the cell proliferation data.

The cytocompatibility of silk-based materials was affected by many processing-related factors. Residues from HFIP during SNF preparation could pose toxicity to cells. The in vitro cytocompatibility study with human dermal fibroblasts (HDFs) showed that the SNF membranes fabricated in this study were not toxic to fibroblasts, thus supporting the removal of all HFIP during processing of these new membranes. Benefiting from the connected nanoporous structure of these SNF membranes, advantages can be considered for applications in membrane-based biomedical devices. The connected nanoporous structure could facilitate moisture and nutrient transfer and provide nanoconfined volumes for housing bioactive molecules as well modulating material degradation over time.

To evaluate the transmittance of SNFs membranes, an approximately 200 μm thick membrane was characterized via UV-vis spectrophotometer (FIG. 40, panels a, b). The membrane was optically transparent (above 70% transmission) throughout the visible region (300-800 nm), and up to 88% at 800 nm (FIG. 40, panels a, b). These transmission values were higher than the as cast (73% at 800 nm) and ethanol-treated (60% at 800 nm) SF membrane (insert of FIG. 40, panel a, FIG. 40, panel b) with similar thickness, and comparable with transparent polymeric membranes prepared from polycarbonate (89%) and poly(methyl methacrylate) (92%).

In addition, silk fibroin, as an amphiphilic polymer, constituted by chains containing alternating hydrophobic and hydrophilic domains (FIG. 34, panel a), can absorb different types of dye, to generate membranes with different colors. Colored luminescent SNF membranes, with "M" and "T" letter patterns were colored by rhodamine B and rhodamine 123, respectively (FIG. 40, panel c). To verify the luminescent properties of silk fibroin with ultralow dye concentrations, the colored letter "M" was prepared with Rhodamine B (1 nM) at a concentration 1000 times lower than that of Rhodamine 123 (1 μM). The letter "M" was transparent under visible light, but showed bright red luminescence under UV light.

Additionally, the SNF membranes were able to take up different kinds of quantum dots to develop transparent optical nano-devices. CdSeS/ZnS quantum dots were patterned on the SNF membranes through masked vacuum filtration (FIG. 40, panel d). The membranes were also transparent with no icon observed under visual light, while the bright green icon appeared once the membrane was illuminated under UV light. These approaches to functionalize silks provide options towards bio-optic, packaging and anti-counterfeiting devices.

Besides the application in optical devices, the SNFs can also be constructed to flexible electronic devices. The steps of fabricating SNFs-based electric devices are illustrated in FIG. 41, panel a. The approach is different from routine methods, such as transfer printing and atomic deposition, which require complicated design and preparation processes. Instead, vacuum-assisted filtration was used to fabricate patterned SNFs electronic devices. First, large single gold crystal platelets, for conduction, were synthesized on the exfoliated SNFs at pH 1. Chloroauric acid was used as the source of gold and the SNFs were the reductant. The synthesized gold nanoplatelets are also suitable for biological applications. FIG. 41, panel b presents gold colloidal suspensions formed basing on 0.05 wt % SNFs and 0.1 wt % gold nanoplatelets (based on 100% reduction yield). The suspension possesses a characteristic golden color with a shining surface due to the reflection of light. The SEM image (FIG. 41, panel c) revealed that the synthetic gold nanoplatelets were hexagonal, triangular, and polyhedral with lateral sizes up to 10 μm. Next, the gold nanoplatelet suspensions were added to a patterned mold, which was supported by a vacuum filtration membrane. After the gold nanoplatelet suspension was dried, the mold was removed, and the SNF dispersion was added to the filtration bottle. The patterned conductive SNFs electronic devices could be obtained after drying (FIG. 41, panels d-e).

The moss green solid line in FIG. 41, panel f presents the non-linear relationship between weight and volume composition of gold platelets in the membranes arose from the large density mismatch between gold and protein (gold has a density about 14 times higher than the protein). At low gold content, the volume fraction weakly depends on the weight fraction of gold. By increasing the gold content, this dependence becomes stronger. Accordingly, the electric conductivity of these SNFs/gold nanoplatelet membranes were tunable by changing the weight (or volume) ratio of gold nanoplatelets and SNFs used in the process. The membranes generated insulating-like in-plane conductivities for gold contents ≤74 wt % (or 15.3 vol %) (conductivity <$10^{-8}$ S $cm^{-1}$, the white region in FIG. 41, panel f), while metallic conductivities were about $10^3$ S $cm^{-1}$ with the threshold composition of 74 wt % (or 15.3 vol %) gold nanoplatelets (the shadow region in FIG. 41, panel f). These results were similar to amyloid/gold hybrids (the threshold composition of 87 wt %), but with a lower threshold value. The conductivities increased with more gold content and reached $10^4$ S $cm^{-1}$ with weight fraction of gold up to 92 wt % (44.8 vol %).

More remarkably, the gold conducting layers had strong adhesion with the SNF membranes due to the compatibility with the SNFs in the gold conducting layer. The conducting pattern, with 74 wt % gold nanoplatelets as an example, demonstrated that there are strong binding forces between gold conducting layers and the SNF substrate to withstand the tearing of the tape (Top image in FIG. 41, panel g). The transfer printing pattern was damaged by adhesive tape (Bottom image in FIG. 41, panel g). The SEM image (FIG. 41, panel h) confirmed no gap was present between the gold conducting layer and the SNF membrane layer. In addition, these SNF membranes with connected nonporous structures can easily trap and transmit water molecules, and hence can be adhered to gloves, skins (FIG. 41, panel i, FIG. 42) and deformed with skins under 85% relative humidity (FIG. 41, panel j, FIG. 42), suggesting utility for electronic skins, biosensors and micro-actuators.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A composition comprising a plurality of exfoliated silk microfibrils and/or silk nanofibrils, wherein the plurality of exfoliated silk microfibrils and/or silk nanofibrils are not made from regenerated silk fibroin, wherein the plurality of exfoliated silk microfibrils and/or silk nanofibrils comprise a hierarchical structure of native silk fibroin fibrils in an interior portion of the plurality of exfoliated silk microfibrils and/or silk nanofibrils, wherein the plurality of exfoliated silk microfibrils and/or silk nanofibrils have a modified surface chemistry by virtue of partial dissolution by a polar solvent, wherein the plurality of exfoliated silk microfibrils and/or silk nanofibrils can be dissolved or dispersed in an aqueous solution by virtue of the modified surface chemistry.

2. The composition of claim 1, further comprising a substrate.

3. The composition of claim 2, wherein the plurality of exfoliated silk microfibrils and/or silk nanofibrils comprise a coating.

4. The composition of claim 1, wherein the composition is or comprises a sensor or implant.

5. The composition of claim 1, further comprising at least one additive.

6. The composition of claim 5, wherein at least one additive is or comprises a dye, a growth factor, an anti-inflammatory agent, an anti-microbial agent, quantum dots, conductive polymers, or an inorganic material.

7. The composition of claim 5, wherein at least one additive is or comprises carbon nanotubes.

8. The composition of claim 1, wherein the composition is a solution.

9. The composition of claim 1, the composition comprising the plurality of exfoliated silk microfibrils.

10. The composition of claim 9, wherein the plurality of exfoliated silk microfibrils have a diameter between 5 and 50 µm, inclusive.

11. The composition of claim 9, wherein the plurality of exfoliated silk microfibrils have a length between 5 µm and 50 mm, inclusive.

12. The composition of claim 1, the composition comprising the plurality of silk nanofibrils.

13. The composition of claim 12, wherein the silk nanofibrils have a diameter between 2 and 200 nm, inclusive.

14. The composition of claim 12, wherein the silk nanofibrils have a length between 50 and 2 µm, inclusive.

15. The composition of claim 12, wherein the silk nanofibrils comprise a helical or spiral structure.

16. The composition of claim 1, further comprising a cell.

17. The composition of claim 16, wherein the cell is selected from the group consisting of fibroblasts, stem cells, immune cells, nervous system cells, adipose tissue-derived cells, and blood cells.

18. The composition of claim 1, wherein the plurality of exfoliated silk microfibrils and/or silk nanofibrils each individually have an elongation at break that is substantially the same as a native silk fiber.

19. The composition of claim 1, further comprising a metal or ceramic material.

20. An article comprising the composition of claim 1.

* * * * *